(12) United States Patent
Prince et al.

(10) Patent No.: US 11,844,708 B2
(45) Date of Patent: *Dec. 19, 2023

(54) PROSTHETIC KNEE WITH A RECTIFICATION HYDRAULIC SYSTEM

(71) Applicant: Proteor USA, LLC, Tempe, AZ (US)

(72) Inventors: Stephen W. Prince, Irvine, CA (US); Jonathan M. Byars, Orange, CA (US); Robert M. Glidden, IV, Irvine, CA (US); Hugo A. Quintero, Santa Ana, CA (US); Michael L. Palmer, Ladera Ranch, CA (US)

(73) Assignee: Proteor USA, LLC, Tempe, AZ (US)

(*) Notice: Subject to any disclaimer, the term of this patent is extended or adjusted under 35 U.S.C. 154(b) by 111 days.

This patent is subject to a terminal disclaimer.

(21) Appl. No.: 17/540,870

(22) Filed: Dec. 2, 2021

(65) Prior Publication Data

US 2022/0087835 A1 Mar. 24, 2022

Related U.S. Application Data

(63) Continuation of application No. 16/489,673, filed as application No. PCT/US2018/020748 on Mar. 2, 2018, now Pat. No. 11,213,407.

(60) Provisional application No. 62/466,305, filed on Mar. 2, 2017.

(51) Int. Cl.
*A61F 2/68* (2006.01)
*A61F 2/64* (2006.01)
(Continued)

(52) U.S. Cl.
CPC .......... *A61F 2/68* (2013.01); *A61F 2/64* (2013.01); *A61F 2/6607* (2013.01); *A61F 2/74* (2021.08);
(Continued)

(58) Field of Classification Search
CPC .. A61F 2/68; A61F 2/64; A61F 2/6607; A61F 2/748; A61F 2/74; A61F 2002/5006
See application file for complete search history.

(56) References Cited

U.S. PATENT DOCUMENTS 4,726,583 A * 2/1988 Olsen ............... A63B 21/00072
417/313
5,062,857 A * 11/1991 Berringer ............... A61F 2/64
623/25

(Continued)

FOREIGN PATENT DOCUMENTS

| CN | 101404959 A | 4/2009 |
| CN | 105748178 A | 7/2016 |

(Continued)

*Primary Examiner* — Paul B Prebilic
(74) *Attorney, Agent, or Firm* — Noblitt & Newson, PLLC

(57) ABSTRACT

Described here are prosthetic systems, devices, and methods of use therefor. Generally, a prosthesis may be configured to set a resistance to rotation of a prosthetic joint based on a phase of gait. The prosthesis may include a first cylinder, a first piston slidable within the first cylinder, a fluid sump, and a fluid circuit. The fluid circuit may include a plurality of interconnected fluid channels having a unidirectional variable-resistance valve and a set of check valves that are configured to provide unidirectional flow through the valve during piston compression and extension.

38 Claims, 31 Drawing Sheets

(51) Int. Cl.
  *A61F 2/66* (2006.01)
  *A61F 2/50* (2006.01)
  *A61F 2/70* (2006.01)
  *A61F 2/76* (2006.01)
  *A61F 2/74* (2006.01)
(52) U.S. Cl.
  CPC ............... *A61F 2/741* (2021.08); *A61F 2/748* (2021.08); *A61F 2002/5006* (2013.01); *A61F 2002/704* (2013.01); *A61F 2002/764* (2013.01); *A61F 2002/7635* (2013.01); *A61F 2002/7645* (2013.01); *A61F 2002/7655* (2013.01); *A61F 2002/7665* (2013.01)

(56) References Cited

U.S. PATENT DOCUMENTS

| | | | |
|---|---|---|---|
| 5,064,193 A * | 11/1991 | Sainte | A63B 21/0083 482/113 |
| 6,113,642 A | 9/2000 | Petrofsky et al. | |
| 7,655,050 B2 | 2/2010 | Palmer et al. | |
| 9,028,557 B2 | 5/2015 | Steele et al. | |
| 2007/0027555 A1 | 2/2007 | Palmer et al. | |
| 2008/0262635 A1 | 10/2008 | Moser et al. | |
| 2009/0068012 A1 | 3/2009 | Bertolotti | |
| 2009/0192625 A1 | 7/2009 | Bolten | |
| 2013/0150980 A1 * | 6/2013 | Swift | A61F 2/70 623/24 |
| 2013/0268091 A1 | 10/2013 | Shen | |
| 2014/0277581 A1 | 9/2014 | Steele et al. | |
| 2016/0235558 A1 | 8/2016 | Boender et al. | |

FOREIGN PATENT DOCUMENTS

| | | | |
|---|---|---|---|
| CN | 106255477 A | 12/2016 | |
| CN | 106344221 A | 1/2017 | |
| DE | 19621034 A1 * | 12/1996 | ............ A61F 2/644 |
| SU | 1416106 A1 | 8/1988 | |
| WO | WO-2007095933 A2 * | 8/2007 | ............ A61F 2/605 |
| WO | WO-2010005473 A1 * | 1/2010 | ............ A61F 2/64 |
| WO | 2016142680 A1 | 9/2016 | |

* cited by examiner

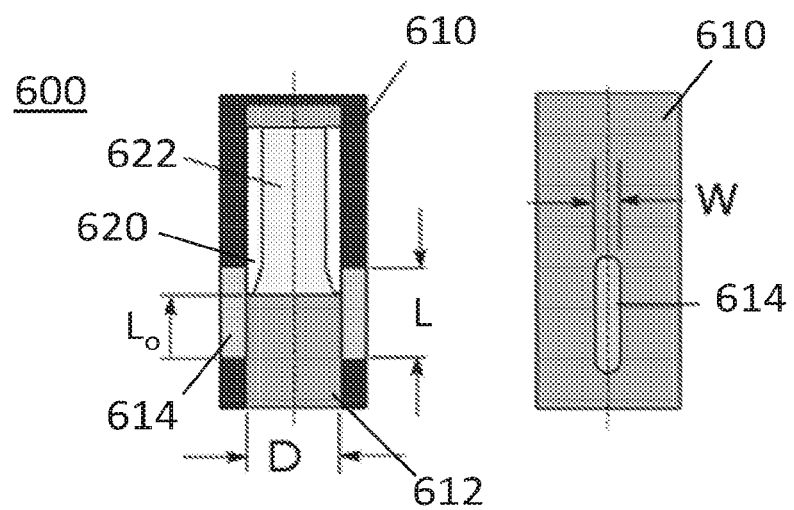
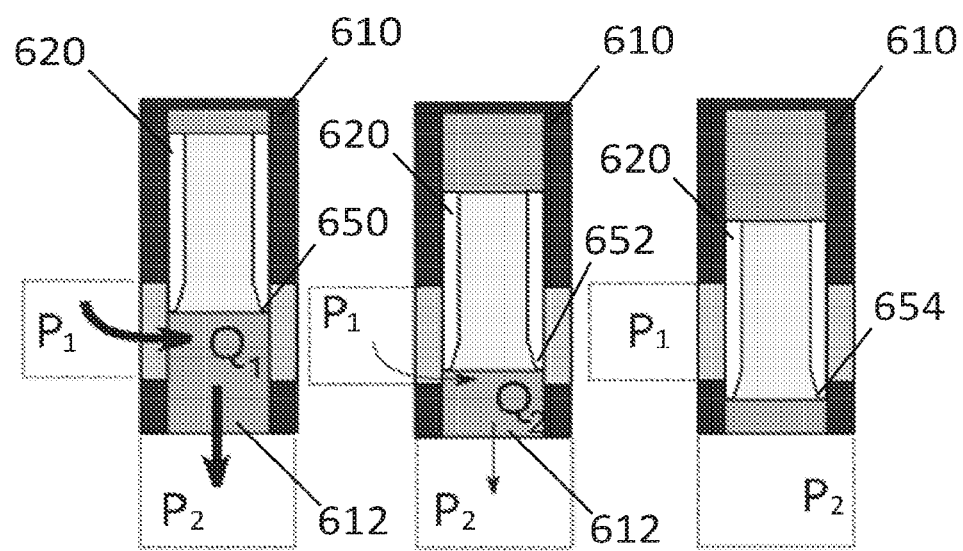
FIG. 6A  FIG. 6B
FIG. 6C  FIG. 6D  FIG. 6E

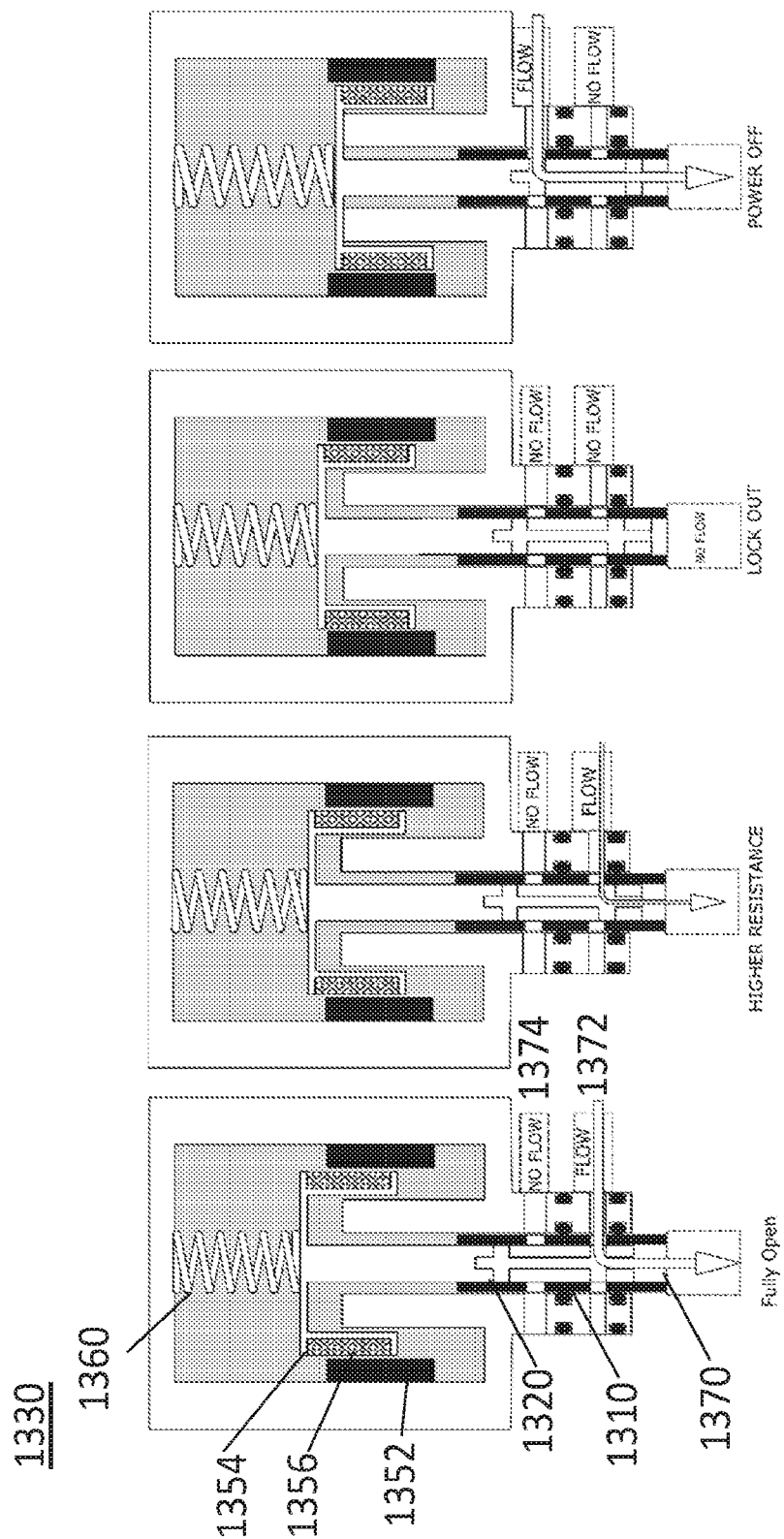

PROSTHETIC KNEE WITH A RECTIFICATION HYDRAULIC SYSTEM

CROSS-REFERENCE TO RELATED APPLICATIONS

This application in a continuation of U.S. patent application Ser. No. 16/489,673, filed Aug. 28, 2019, entitled "PROSTHETIC KNEE WITH A RECTIFICATION HYDRAULIC SYSTEM", now U.S. Pat. No. 11,213,407, which claims priority to PCT/US18/20748, filed Mar. 2, 2018, which claims priority to U.S. Provisional Application Ser. No. 62/466,305, filed on Mar. 2, 2017, the contents of each are hereby incorporated by reference in their entirety.

FIELD

Systems and methods herein relate to prosthetics with a hydraulic damping system, including but not limited to prosthetic knees and ankles.

BACKGROUND

Prosthetic limbs are designed to substitute for a body part that may be missing due to trauma, disease, or congenital conditions. The development of prosthetics such as a prosthetic knee with a more natural gait or function is an ongoing endeavor. Some prosthetic knees include a hydraulic system to control rotation of a rotor coupled to a shank about a knee joint. Some hydraulic systems include a hydraulic cylinder, piston, hydraulic fluid, and a hydraulic circuit having hydraulic fluid channels and valves for controlling a resistance of the hydraulic fluid flowing through the hydraulic system. A range of motion of the prosthetic joint may thus be controlled to mimic natural gait. However, hydraulic systems need to be capable of fast response times in order to transition the prosthetic joint to different levels of resistance when transitioning between stance phase and swing phase movement. The size and complexity of the hydraulic systems also affects the performance and cost of the prosthetics. Therefore, additional prosthetic devices may be desirable.

SUMMARY

Described herein are prosthetic joint systems and methods. A lower limb prosthesis such as a prosthetic knee may be coupled to a hydraulic damping system and be configured to set a resistance of the prosthetic knee joint based on a phase of gait. In order to increase user safety, the hydraulic systems should function in a predictable manner under conditions such as an unexpected loss of power. The prosthesis may include a first cylinder, a first piston slidable within the first cylinder, a fluid sump, and a fluid circuit. The fluid circuit may include a plurality of intersecting or interconnected fluid channels or paths having a unidirectional variable-resistance valve and a set of check valves that may be configured to permit unidirectional flow through the valve during piston compression and extension, or during flexion and extension of the prosthesis.

In one example, a prosthesis is provided, comprising a first cylinder with a first cylinder port and a second cylinder port, a first piston slidable within the first cylinder, a fluid sump comprising a sump port, and a fluid circuit. The fluid circuit may comprise a first fluid channel comprising a first channel inlet, a first channel outlet, and a unidirectional variable-resistance valve configured to set a variable resistance to flow through the first fluid channel, a second fluid channel comprising a second channel inlet, a second channel outlet, and a second channel check valve. A third fluid channel may comprise a third channel inlet, a third channel outlet and a third channel check valve. A fourth fluid channel may comprise a fourth channel inlet, a fourth channel outlet, and a fourth channel check valve. A fifth fluid channel may comprise a fifth channel inlet, a fifth channel outlet and a fifth channel check valve. A first intersection (e.g., interconnection) may comprise the first channel inlet, the second channel outlet, and the fifth channel outlet. A second intersection may comprise the first cylinder port, the second channel inlet and the third channel outlet. A. third intersection may comprise the sump port, the third channel inlet and the fourth channel inlet. A fourth intersection may comprise the second cylinder port, the fourth channel outlet and the fifth channel inlet. A hydraulic assembly comprising the above components may also be provided for use with a limb prosthesis, orthotic, assistive device, or robotic linkage.

The prosthesis or hydraulic assembly may further comprise a flexion state during cylinder compression wherein the fluid circuit may be configured to permit fluid flow along a first fluid path sequentially through the second cylinder port, the fifth channel check valve, the variable-resistance valve, the third channel check valve, and to the first cylinder port. The flexion state may also be further configured to permit fluid flow in a second fluid path from the variable-resistance valve and to the sump port, and optionally to resist fluid flow through the second channel check valve and the fourth channel check valve. The flexion state may be configured to permit fluid flow simultaneously in the first and second fluid paths. The prosthesis may further comprise an extension state during cylinder extension wherein the fluid circuit is configured to permit fluid flow along a third fluid path sequentially through the first cylinder port, the second channel check valve, the variable-resistance valve, the fourth channel check valve, and to the second cylinder port. The extension state may be further configured to permit fluid flow along a fourth fluid path sequentially from the sump port and to the fourth channel check valve, and may be further configured to resist fluid flow through the second channel check valve and the fourth channel check valve, and/or configured to permit fluid flow simultaneously in the third and fourth fluid paths. The prosthesis may include a mechanical sensor, wherein a resistance of the variable-resistance valve may be determined based upon input from the mechanical sensor. The variable-resistance valve may be selected from the group consisting of a solenoid valve, a spool valve, and a voice coil valve.

The fluid circuit may further comprise a three-way valve, which may comprise a first valve port connected to the fluid sump at a second sump port, a second valve port connected to the second intersection, and a third valve port connected to the fourth intersection. The prosthesis or fluid circuit may further comprise a variable resistor located between the third valve port and the fourth intersection along a sixth fluid channel. The sixth fluid channel may comprise a sixth channel inlet at the fourth intersection and a sixth channel outlet connected to the third valve port. The variable resistor may be user adjustable, with a dynamic or static setting. The variable resistor may be a unidirectional variable resistor configured to permit flow from the fourth intersection to the third valve port.

The three-way valve may be a normally open three-way valve, and in some further examples, may be configured to permit fluid passage between the first, second, and third valve ports when open, and to block fluid passage between the first, second, and third valve ports when closed. The variable resistor may be configured to block fluid flow from the third valve port to the fourth intersection regardless of whether the three-way valve is open or closed. The prosthesis may further comprise a power-off flexion state during cylinder compression wherein the fluid circuit is configured to permit fluid flow along a fifth fluid path sequentially through the second cylinder port, the variable resistor, the third valve port, the second valve port, and to the first cylinder port. The fluid circuit of the power-off flexion state may be further configured to permit a fluid flow along a sixth fluid path from the first valve port to the fluid sump. The prosthesis may further comprise a power-off extension state wherein the fluid circuit may be configured to permit fluid flow along a seventh fluid path sequentially through the first cylinder port, the second valve port, the first valve port, the first sump port, the fourth fluid channel, and to the second cylinder port. In some further examples, the variable resistance valve in the first fluid channel may be a three-way spool valve and further comprise a secondary channel inlet.

The fluid circuit may also further comprise a seventh fluid channel comprising a seventh channel inlet, a seventh channel outlet, and a seventh channel check valve, wherein the seventh channel inlet may be connected to the first cylinder port or the second intersection. An eighth fluid channel may comprise an eighth channel inlet, an eighth channel outlet, and a variable resistor. A fifth intersection may comprise the seventh fluid channel outlet, the eighth channel outlet and the secondary inlet of the three-way spool valve, wherein the first intersection further comprises the eighth channel inlet. The prosthesis may also further comprise a power-off flexion state during cylinder compression wherein the fluid circuit may be configured to permit fluid flow along an eighth fluid path sequentially through the second cylinder port, the fifth fluid channel, the eighth fluid channel, the second inlet of the variable resistance valve, the third fluid channel, and to the first cylinder port. The fluid circuit of the power-off flexion state may be further configured to permit a fluid flow from the first channel outlet to the fluid sump.

The prosthesis or hydraulic assembly may also further comprise a power-off extension state during cylinder extension wherein the fluid circuit may be configured to permit fluid flow along a ninth fluid path sequentially through the first cylinder port, the seventh fluid channel, the first second inlet of the variable resistance valve, the fourth fluid channel, and to the second cylinder port. The power-off extension state may be further configured to permit a fluid flow from the fluid sump to the fourth fluid channel. The three-way spool valve may comprise a spring and may be configured to normally permit fluid communication between the secondary inlet and the first channel outlet when the three-way spool valve is not powered. The fluid sump may also comprise a spring-biased piston or a pneumatic piston. The prosthesis may also further comprise an upper joint member coupled to the first piston, and a lower joint member coupled to the upper joint member and the first cylinder. The prosthesis may be a prosthetic knee or a prosthetic ankle. The prosthesis may also further comprise a load cell disposed on at least one of the first cylinder and the first piston.

In still other examples, methods of using the hydraulic assembly or prosthesis above are provided, comprising transmitting hydraulic fluid in the fluid circuit as indicated during the flexion state during prosthesis flexion and when the prosthesis variable resistance valve is powered, and transmitting hydraulic fluid in the fluid circuit as indicated during the extension state during prosthesis extension and when the prosthesis variable resistance valve is powered. Another method of using the hydraulic assembly or prosthesis may comprise transmitting hydraulic fluid in the fluid circuit as indicated during the flexion state during prosthesis flexion and when the prosthesis variable resistance valve is powered, transmitting hydraulic fluid in the fluid circuit as indicated during the extension state during prosthesis extension and when the prosthesis variable resistance valve is powered, and transmitting hydraulic fluid in the fluid circuit as indicated during the power-off flexion state during prosthesis flexion and when the prosthesis variable resistance valve is not powered. Still another method of using the hydraulic assembly or prosthesis may comprise transmitting hydraulic fluid in the fluid circuit as indicated during the flexion state during prosthesis flexion and when the prosthesis variable resistance valve is powered, transmitting hydraulic fluid in the fluid circuit as indicated during the extension state during prosthesis extension and when the prosthesis variable resistance valve is powered, transmitting hydraulic fluid in the fluid circuit as indicated during the power-off flexion state during prosthesis flexion and when the prosthesis variable resistance valve is not powered, and transmitting hydraulic fluid in the fluid circuit as indicated during the power-off extension state during prosthesis extension and when the prosthesis variable resistance valve is not powered.

In another example, a fluid circuit is provided, comprising a first fluid channel comprising a first channel inlet, a first channel outlet, and a unidirectional variable-resistance valve configured to set a variable resistance to flow through the first fluid channel. A second fluid channel may comprise a second channel inlet, a second channel outlet, and a second channel check valve. A third fluid channel may comprise a third channel inlet, a third channel outlet and a third channel check valve. A fourth fluid channel may comprise a fourth channel inlet, a fourth channel outlet, and a fourth channel check valve. A fifth fluid channel may comprise a fifth channel inlet, a fifth channel outlet, and a fifth channel check valve. A first intersection (e.g., interconnection) may comprise the first channel inlet, the second channel outlet, and the fifth channel outlet. A second intersection may comprise a first bi-directional channel, the second channel inlet, and the third channel outlet. A third intersection may comprise a second bi-directional channel, the third channel inlet, and the fourth channel inlet. A fourth intersection may comprise a third bi-directional channel, the fourth channel outlet and the fifth channel outlet. The fluid circuit may further comprise a first state wherein the fluid circuit is configured to permit fluid flow along a first fluid path sequentially through the third bidirectional channel, the fifth channel check valve, the variable-resistance valve, the third channel check valve, and to the first directional channel. The first state may be further configured to permit fluid flow in a second fluid path from the variable-resistance valve and to the second bi-directional channel, and may be further configured to resist fluid flow through the second channel check valve and the fourth channel check valve. The first state may be configured to permit fluid flow simultaneously along the first and second fluid paths.

The fluid circuit may further comprise a second state wherein the fluid circuit may be configured to permit fluid flow along a third fluid path sequentially through the first bidirectional channel, the second channel check valve, the variable-resistance valve, the fourth channel check valve, and to the third bi-directional channel. The second state may be further configured to permit fluid flow along a fourth fluid path sequentially from the second bidirectional channel and to the fourth channel check valve. The second state may be further configured to resist fluid flow through the second channel check valve and the fourth channel check valve. The second state may be configured to permit fluid flow simultaneously in the third and fourth fluid paths. The fluid circuit may further comprise a mechanical sensor and a resistance of the variable-resistance valve may be determined based upon input from the mechanical sensor. The variable-resistance valve may be selected from the group consisting of a solenoid valve, a spool valve and a voice coil valve. The fluid circuit may further comprise a three-way valve, comprising a first valve port connected to the second bi-directional channel, a second valve port connected to the second intersection, and a third valve port connected to the fourth intersection. The fluid circuit may further comprise a variable resistor located between the third valve port and the fourth intersection along a sixth fluid channel, the sixth fluid channel may comprise a sixth channel inlet at the fourth intersection and a sixth channel outlet connected to the third valve port. The variable resistor is a unidirectional variable resistor configured to permit flow from the fourth intersection to the third valve port. The variable resistor may be user adjustable, with a dynamic or static setting. The three-way valve may be a normally open three-way valve. The three-way valve may be configured to permit fluid passage between the first, second, and third valve ports when open, and to block fluid passage between the first, second, and third valve ports when closed. The variable resistor may be configured to block fluid flow from the third valve port to the fourth intersection regardless of whether the three-way valve is open or closed.

The fluid circuit may further comprise a third state wherein the fluid circuit may be configured to permit fluid flow along a fifth fluid path sequentially through the third bidirectional channel, the variable resistor, the third valve port, the second valve port, and to the first bi-directional channel. The third state of the fluid circuit may be further configured to permit a fluid flow along a sixth fluid path from the first valve port to the second bi-directional channel. The fluid circuit may further comprise a power-off extension state wherein the fluid circuit may be configured to permit fluid flow along a seventh fluid path sequentially through the first cylinder port, the second valve port, the first valve port, the first sump port, the fourth fluid channel, and to the second cylinder port. The variable resistance valve may be a three-way spool valve and further comprise a secondary channel inlet. The fluid circuit may further comprise a seventh fluid channel comprising a seventh channel inlet, a seventh channel outlet, and a seventh channel check valve, wherein the seventh channel inlet is connected to the first bidirectional channel or the second intersection. An eighth fluid channel may comprise an eighth channel inlet, an eighth channel outlet, and a variable resistor, and a fifth intersection of the seventh fluid channel outlet, the eighth channel outlet and the secondary inlet of the three-way spool valve. The first intersection may further comprise the eighth channel inlet. The fluid circuit may further comprise a third state wherein the fluid circuit may be configured to permit fluid flow along an eighth fluid path sequentially through the third bi-directional channel, the fifth fluid channel, the eighth fluid channel, the secondary channel inlet of the variable resistance valve, the third fluid channel, and to the first bi-directional channel. The third state of the fluid circuit may be further configured to permit a fluid flow from the first channel outlet to the second bi-directional channel.

The fluid circuit may further comprise a fourth state wherein the fluid circuit may be configured to permit fluid flow along a ninth fluid path sequentially through the first bidirectional channel, the seventh fluid channel, the first second inlet of the variable resistance valve, the fourth fluid channel, and to the third bi-directional channel. The fourth state may be further configured to permit a fluid flow from the second bi-directional channel to the fourth fluid channel. The three-way spool valve may comprise a spring and may be configured to normally permit fluid communication between the secondary inlet and the first channel outlet when the three-way spool valve is not powered. The fluid circuit may further comprise a cylinder comprising a first variable volume chamber, a second variable volume chamber, and a slidable piston therebetween, wherein the first bi-directional channel coupled to the first variable volume chamber and the third bi-directional channel is coupled to the second variable volume chamber. The fluid circuit may also further comprise a fluid sump connected to the second bidirectional fluid channel.

In another example, a hydraulic assembly or prosthetic assembly is provided, comprising a first cylinder comprising a first variable volume cavity, a second variable volume cavity, a piston therebetween, a piston shaft coupled to the piston and slidably extending out of the first variable volume cavity, first cylinder port to the first variable volume cavity, and a second cylinder port to the second variable volume cavity. A fluid circuit may comprise a first unidirectional fluid path containing a proportional valve, a second unidirectional fluid path from the first cylinder port to the first unidirectional fluid path, a third unidirectional fluid path from the first unidirectional fluid path to the first cylinder port, a fourth unidirectional fluid path from the first unidirectional fluid path to the second cylinder port, and a fifth unidirectional fluid path from the second cylinder port to the first unidirectional fluid path. The hydraulic assembly or prosthetic assembly may further comprise a fluid sump coupled to the first unidirectional fluid path and the fourth unidirectional fluid path, and/or a three-way valve with a first valve port connected to the fluid sump, a second valve port connected to the first cylinder port, and a third valve port connected to the second cylinder port. The hydraulic assembly or prosthetic assembly may also further comprise a user-adjustable variable resistor between the third valve port and the second cylinder port. The three-way valve may be normally open. The proportional valve may be a three-way proportional valve and may comprise a secondary channel inlet. The fluid circuit may further comprise a sixth unidirectional fluid path from the fifth unidirectional fluid path to the secondary inlet of the proportional valve, and a seventh unidirectional fluid path from the first cylinder port to the secondary inlet of the proportional valve. The sixth unidirectional fluid path may include a user-adjustable variable resistor. The prosthetic assembly may also further comprise a sensor, and a controller connected to the sensor and to the proportional valve, wherein the controller may be configured to adjust the resistance through the proportional valve based upon the sensor.

The first cylinder may define a longitudinal axis. The fluid circuit may be parallel to the first cylinder and laterally offset from the longitudinal axis. The fluid sump may be parallel and in-line with the fluid circuit.

In another example, a hydraulic assembly or prosthetic is provided, comprising a first cylinder defining a longitudinal axis. The first cylinder may comprise a first cylinder port and a second cylinder port. A first piston may be slidable within the first cylinder. A fluid circuit may be parallel to the first cylinder and laterally offset from the longitudinal axis. The fluid circuit may comprise a set of fluid channels and a variable-resistance valve configured to set a variable resistance to flow through the set of fluid channels. A fluid sump may be parallel and in-line with the fluid circuit. The fluid sump may comprise a sump port. The fluid circuit and the fluid sump may be attached to the first cylinder along a length of the first cylinder.

BRIEF DESCRIPTION OF THE DRAWINGS

FIG. 2A is a side view, FIG. 2B is a perspective view. FIG. 2C is a rear view, and FIG. 2D is a front view.

FIG. 3A is a perspective view and FIG. 3B is a side view.

FIG. 5A illustrates the system architecture, FIG. 5B illustrates fluid flow for flexion, and FIG. 5C illustrates fluid flow for extension.

FIGS. 6A-6F are illustrative schematic views of a variation of a control valve. FIG. 6A is a cross-sectional side view of a sleeve and spool, FIG. 6B is a side view of the sleeve, and FIGS. 6C-6E are cross-sectional side views of fluid flow using the valve. FIG. 6F is a side view of the sleeve, spool, and orifices.

FIG. 7A illustrates the system architecture, FIG. 7B illustrates fluid flow for power ON flexion, and FIG. 7C illustrates fluid flow for power ON extension. FIG. 7D illustrates fluid flow for power OFF flexion and FIG. 7E illustrates fluid flow for power OFF extension.

FIG. 8A illustrates a cross-sectional side view of a proportional spool valve and FIG. 8B illustrates a cross-sectional side view of a power OFF valve. FIG. 8C illustrates a schematic diagram of the valve. FIG. 8D illustrates a schematic diagram of the valve for power OFF flexion. FIG. 8E illustrates a schematic diagram of the valve for power OFF extension.

FIG. 9A illustrates the system architecture. FIG. 9B illustrates fluid flow for power ON flexion and FIG. 9C illustrates fluid flow for power ON extension. FIG. 9D illustrates fluid flow for power OFF flexion and FIG. 9E illustrates fluid flow for power OFF extension.

FIG. 11A illustrates a cross-sectional side view of a three-port spool valve and FIG. 11B illustrates a schematic diagram of the valve. FIGS. 11C and 11D illustrate schematic diagrams of the valve for power ON fluid flow. FIG. 11E illustrates a schematic diagram of the valve for power OFF fluid flow.

FIG. 13B is a cross-sectional side view of a sleeve and spool, and FIGS. 13C-13E are side views of the sleeve, spool, and orifice. FIGS. 13F-13I illustrate schematic diagrams of the valve in a respective fully open state, high resistance state, lock out state, and power OFF state.

DETAILED DESCRIPTION

Described herein are hydraulic assemblies, prosthetic systems, and methods for controlling a hydraulic assembly or prosthesis. A prosthetic joint as described herein may be controlled using a microprocessor to adjust a resistance of the joint based on a phase of gait of the user. In variations where the prosthetic joint includes a hydraulic system including a hydraulic cylinder and piston, the microprocessor may be configured to adjust a hydraulic fluid control valve to set a resistance of hydraulic fluid through the hydraulic system for different phases of a gait cycle. In some variations, the hydraulic system may include components (e.g., valves, fluid channels) to set a resistance of hydraulic fluid through the hydraulic system during power loss for different phases of gait.

I. System

Prosthetic Knee

Described herein are prosthetics for use by an amputee. In some variations, the prosthetic joints shown herein may be configured as a prosthetic knee for use by an above-knee amputee. The prosthetic knee may include a hydraulic system including a hydraulic cylinder coupled to a hydraulic damper. A controller coupled to the hydraulic system may be configured to set a resistance to rotation of the knee joint according to a phase of gait, thus allowing a user to move with a more natural gait motion. As described in more detail, the prosthetic joint may be configured for use in other locations. For example, the prosthetic joint may be configured for use as a prosthetic ankle for a below-knee amputee or an above-knee amputee.

Figures 1A, 1B:
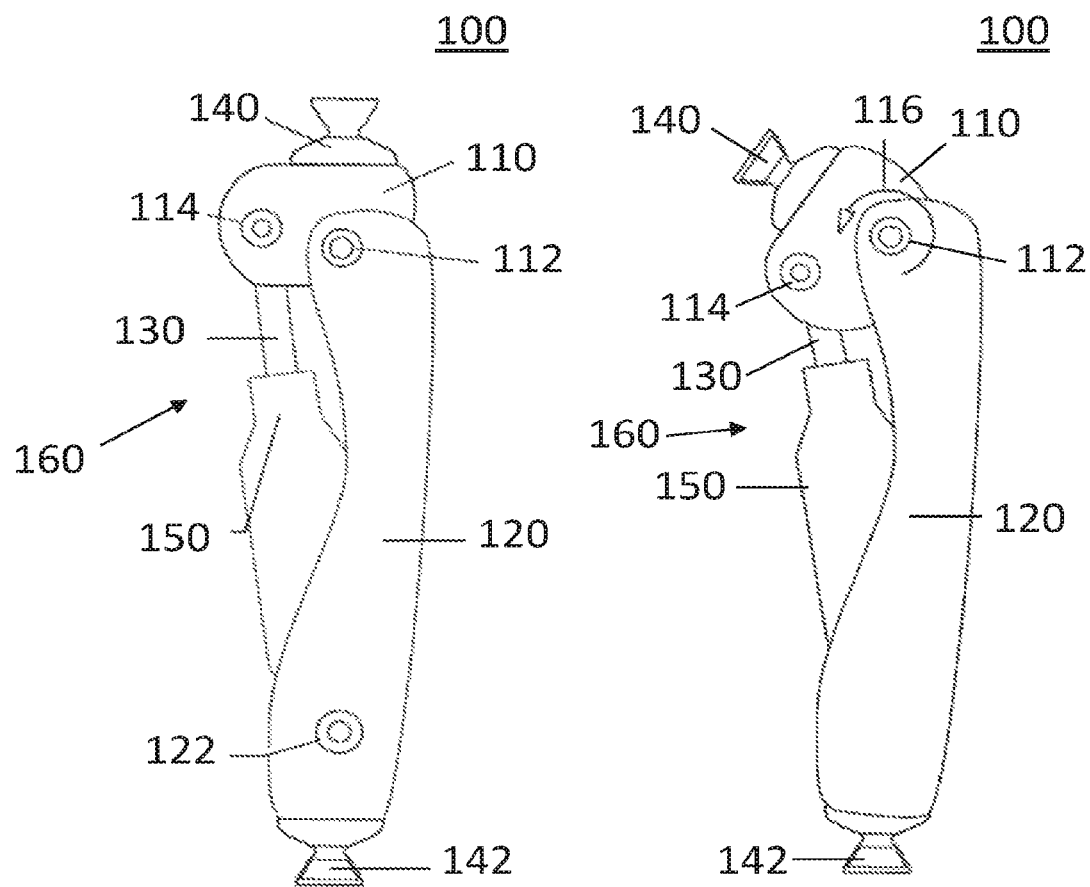
FIGS. 1A-1B are schematic side views of a variation of a prosthetic knee.
Figure 2A:
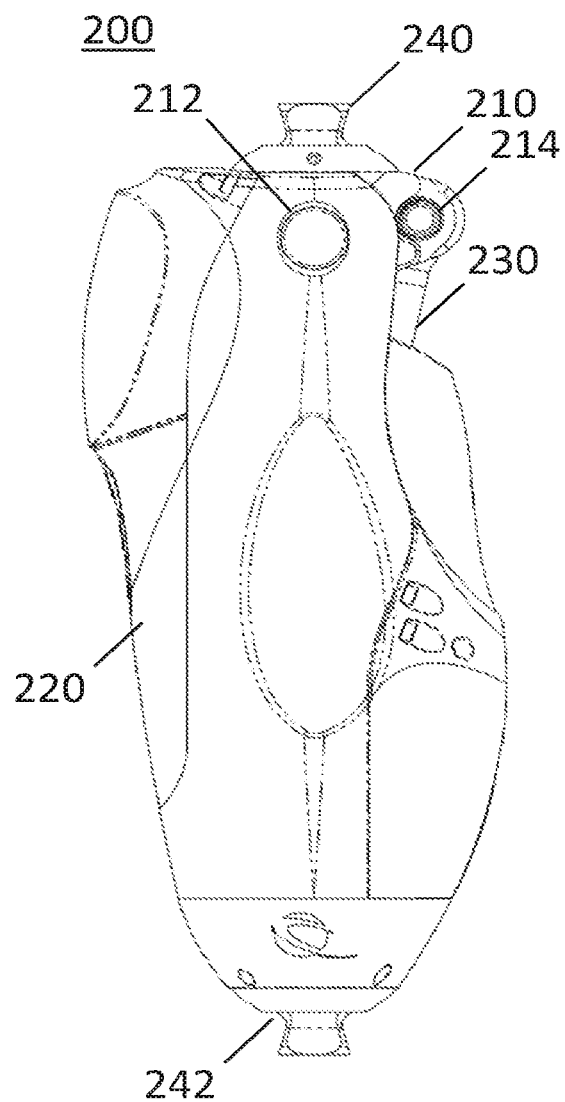
FIGS. 2A-2D are illustrative exterior views of an exemplary variation of a prosthetic knee.
Figure 2B:
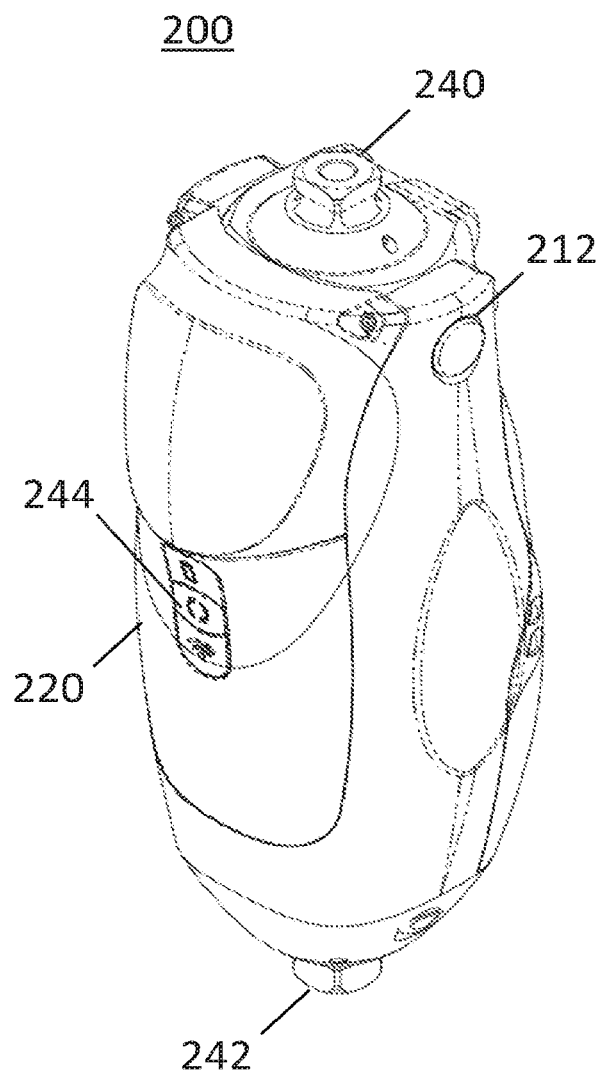
Figure 2C:
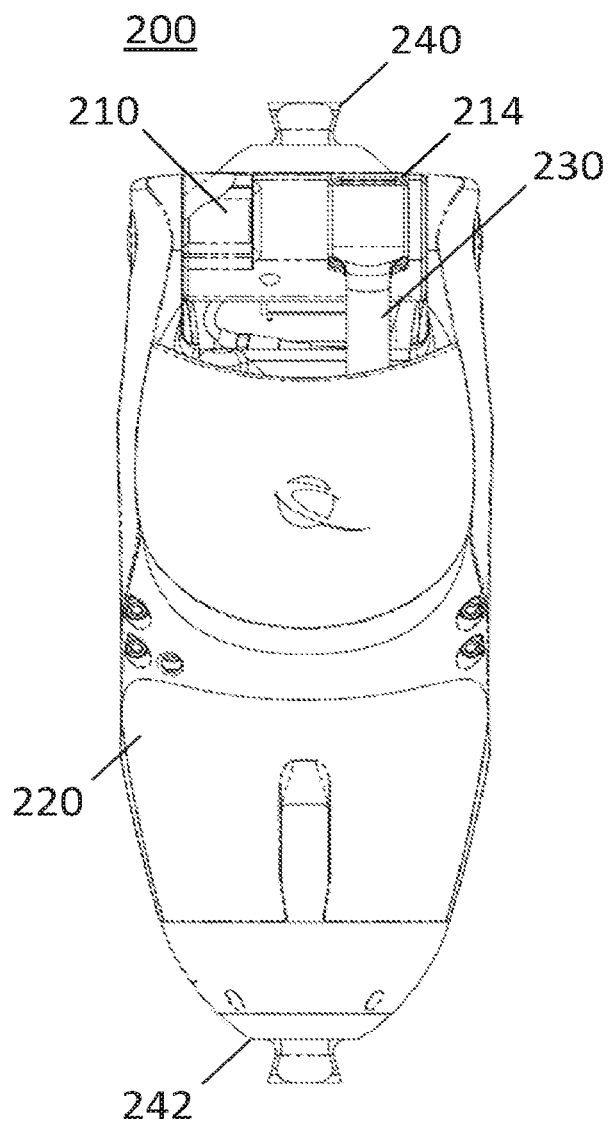
Figure 2D:
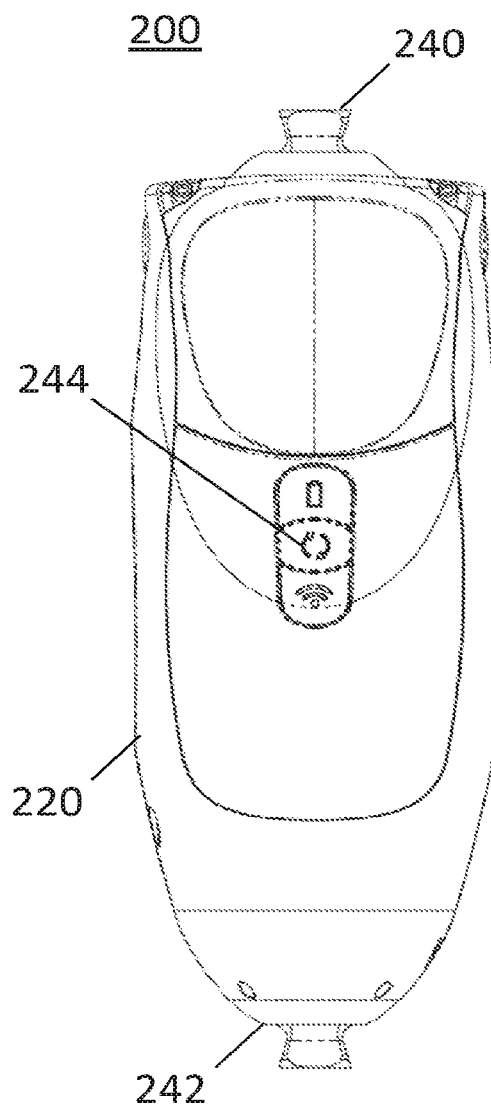

FIGS. 1A-1B illustrate schematic side views of a prosthetic knee (100). The prosthetic knee (100) may include an upper joint member (110) rotatably coupled to a lower joint member (120) about a first joint (112). In some variations, the upper joint member (110) may be a rotor, the lower joint member (120) may be a shank, and the first joint (112) may be a knee joint. The upper joint member (110) and the lower joint member (120) may move with respect to each other in flexion and extension. In variations where the prosthetic joint is a prosthetic ankle, an upper and lower joint member may move with respect to each other in dorsiflexion and plantar flexion. In some variations, the upper joint member (110) and lower joint member (120) may pivot about a single pivot, across a different joint such as a ball-and-socket joint, or across a plurality of points such as in a multi-bar linkage, or other type of linkage.

The upper joint member (110) and the lower joint member (120) may be coupled to a hydraulic system (160) that is configured to actuate and/or dampen rotation of the upper joint member (110) relative to the lower joint member (120). For example, the hydraulic system (160) may be configured to set a rotational resistance of the prosthetic knee (100). A hydraulic system (160) may comprise a piston assembly (130) slidably coupled to a hydraulic cylinder (150). The piston assembly (130) may include a piston (not shown) located within the cylinder (150) and a piston shaft coupled to the piston and extending out of the cylinder (150). Thus, the piston assembly (130) may alternately compress into or extend out of the cylinder (150). FIG. 1A illustrates extension of the piston assembly (130) while FIG. 1B illustrates compression of the piston assembly (130). The upper joint member (110) may rotate (116) relative to the lower joint member (120) absent the first joint (112). The piston assembly (130) may be a linear piston while the chamber of the hydraulic cylinder (150) may be cylindrical. The piston assembly (130) may be coupled to the upper joint member (110) at a first cylinder mount (114). The cylinder (150) may be coupled to the lower joint member (120) at a second cylinder mount (122).

In other examples, the piston assembly (130) may be a rotary piston (not shown) located in a rotary chamber of the cylinder (150), such that the piston assembly (130) may rotate relative to the upper joint member (110) about an axis of the first cylinder mount (114). The cylinder (150) may rotate relative to the lower joint member (120) about an axis of the second cylinder mount (122).

When torque is applied about the first joint (112), the upper joint member (110) may rotate (116) about the first joint (112) such that the piston assembly (130) either compresses into or extends out of the cylinder (150). As the upper joint member (110) and the lower joint member (120) rotate (116) about the joint (112), the piston assembly (130) may rotate about an axis of the first cylinder mount (114) relative to the upper joint member (110), and the cylinder (150) may rotate about an axis of the second cylinder mount (122) relative to the lower joint member (120). The piston assembly (130) may be configured such that an internal cavity of the cylinder (150) is separated into two variable-volume chambers. As the piston assembly (130) moves within the cylinder (150), hydraulic fluid within the cylinder (150) is displaced from one chamber into an opposing chamber. The two chambers may be fluidly connected by a hydraulic damper that may include one or more hydraulic fluid channels and a hydraulic fluid flow control system as described in more detail herein. For example, the hydraulic damper may be fluidly connected with the cylinder (150) through two or more cylinder ports. As described in more detail herein, the hydraulic fluid flow control system may include one or more valves, valve actuators, and fluid sumps.

A resistance to rotation of the joint members about the first joint (112) may be varied (e.g., set between a locked state and an open state) using a control valve (described in more detail herein) of the hydraulic circuit. As the piston assembly (130) moves within the cylinder (150) (e.g., compresses or extends), hydraulic fluid enters the control valve. A controller (e.g., microprocessor including memory) may be configured to control an area of a fluid opening in the control valve. A change in an area of the opening in the control valve may change a resistance to flow of the hydraulic fluid in the hydraulic system (160). A resistance to hydraulic fluid flow through the hydraulic system (160) may correspond to a resistance to rotation of the prosthetic joint and thus a phase of gait. In some variations, the control valve may include a spool slidably coupled to a sleeve.

The upper joint member (110) may be coupled to a first connector (140) and the lower joint member (120) may be coupled to a second connector (142) In some variations, the first connector (140) may be a proximal pyramid connector and the second connector (142) may be a distal pyramid connector.

FIGS. 2A-2D illustrates exterior views of an exemplary variation of a prosthetic knee (200). The prosthetic knee (200) may include a first upper joint member (210) (e.g., rotor) coupled to a lower joint member (220) (e.g., shank) about a first joint (212) (e.g., knee joint). The upper joint member (210) and the lower joint member (220) may move with respect to each other in flexion and extension. The upper joint member (210) may be coupled to a piston assembly (230) with a piston and piston shaft. The piston assembly (230) may be coupled to the upper joint member (210) at a cylinder mount (214). The piston assembly (230) may rotate relative to the upper joint member (210) about an axis of the cylinder mount (214). The upper joint member (210) may be coupled to a first connector (240) (e.g., proximal pyramid) and the lower joint member (220) may be coupled to a second connector (242) (e.g., distal pyramid). In some variations, the first connector (240) may be a proximal pyramid connector and the second connector (242) may be a distal pyramid connector. For example, the first connector (240) may be configured to attach to a socket (not shown), where the socket may be configured to attach to a remnant limb of the amputee. The second connector (242) may be configured to attach to a prosthetic foot and/or ankle (not shown). The prosthesis (200) may also include one or more buttons 244 or other controls to actuate the power, wireless connectivity, battery level display or other features of the prosthesis (200).

Figure 3A:
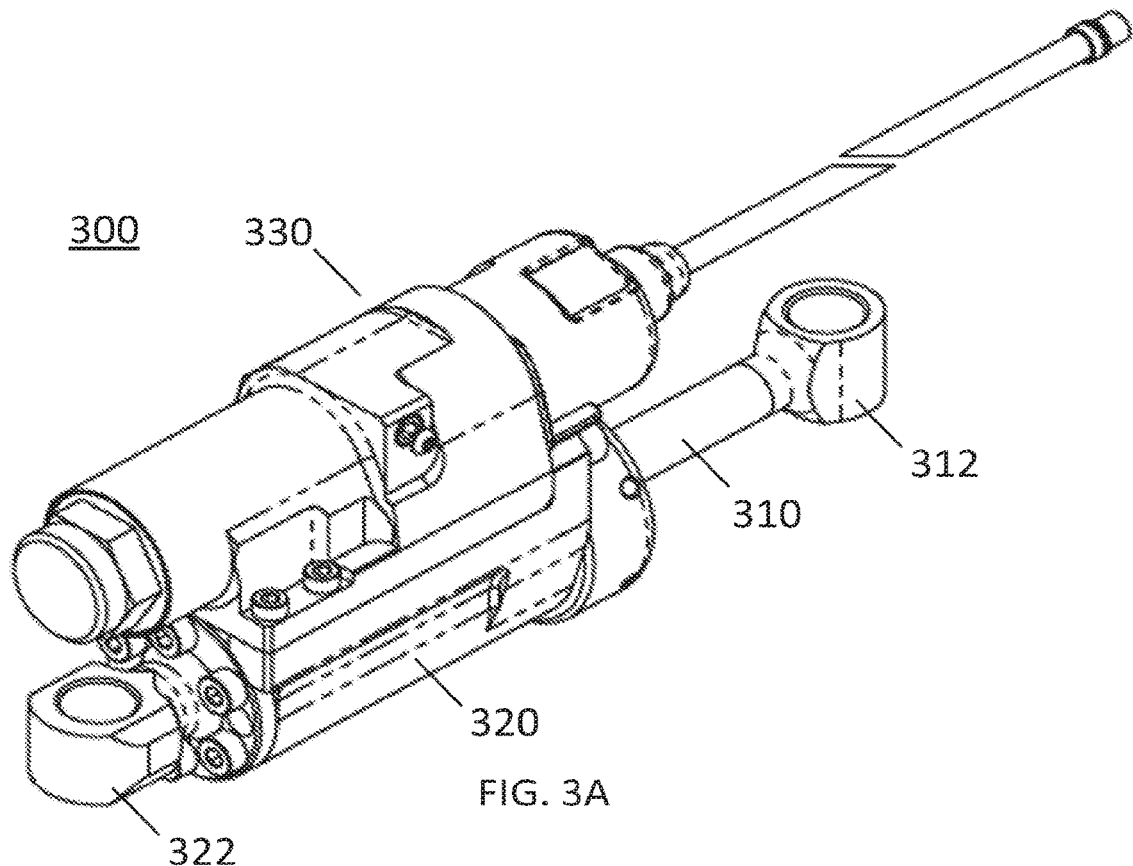
FIGS. 3A-3B are illustrative exterior views of an exemplary variation of a hydraulic system.
Figure 3B:
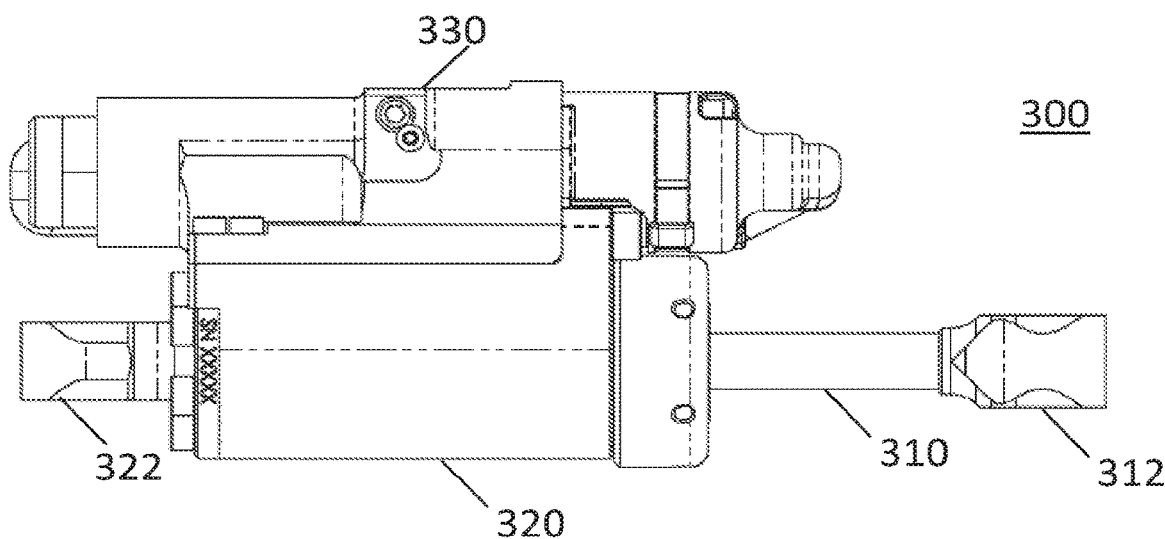
Figure 3C:
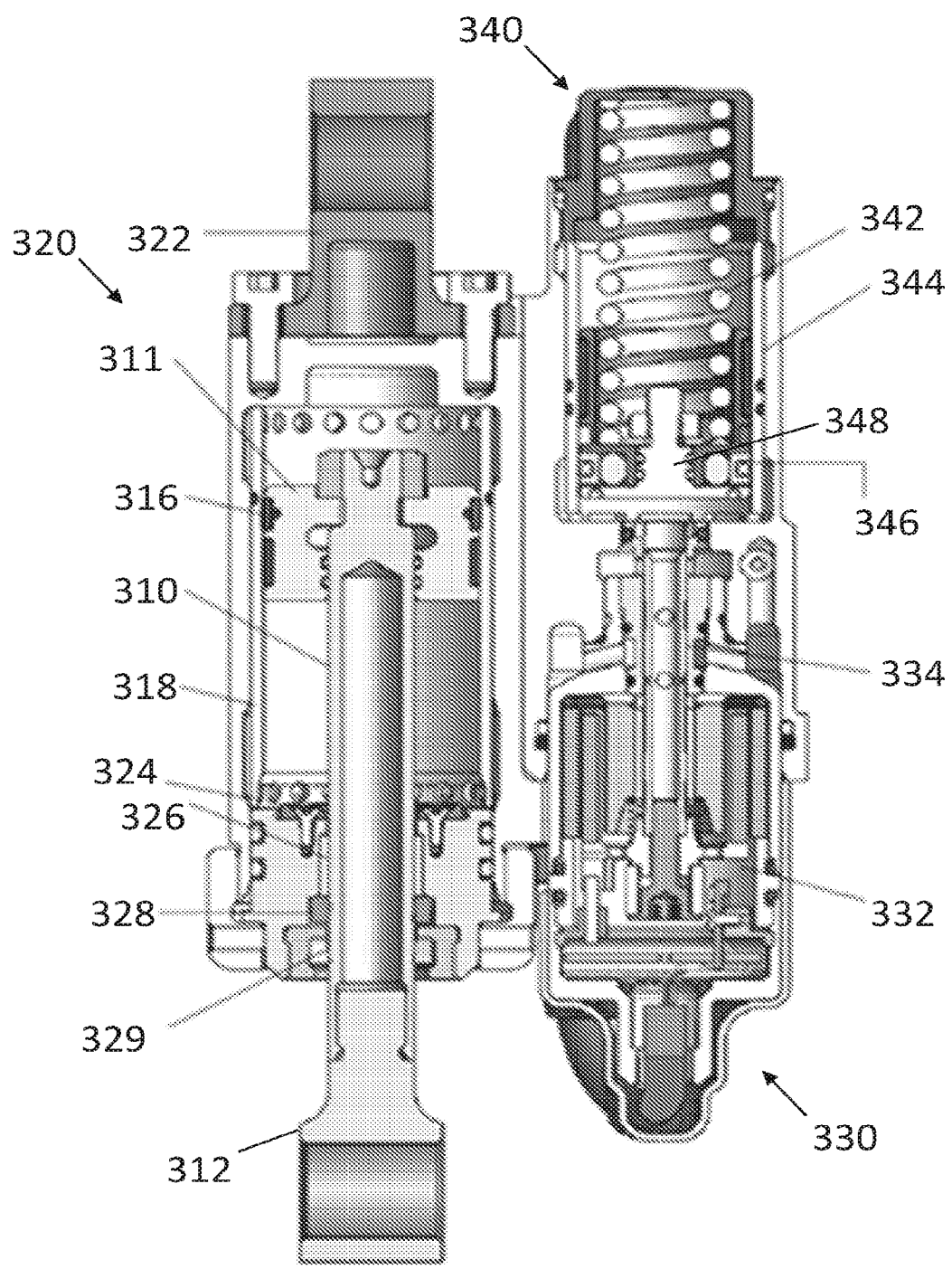
FIG. 3C is a cross-sectional side view of the hydraulic system in FIGS. 3A-3B.

FIGS. 3A-3C illustrate an exemplary variation of a hydraulic assembly (300) that may be used in the prosthetic knee (100, 200) depicted in FIGS. 1A-2D. The hydraulic system (300) may include a piston assembly (310) slidably coupled to a hydraulic cylinder (320), with a piston located in the cylinder (320) and piston shaft extending out of the cylinder (320). An end of the piston assembly (310) may include a first mount (312) and a piston (311). An end of the hydraulic cylinder (320) may include a second mount (322). In some variations, the first mount (310) may rotatably couple to a rotor and the second mount (322) may rotatably couple to a shank. As described in more detail herein, a hydraulic damper (330) may be coupled to the hydraulic cylinder (320) to control a resistance of hydraulic fluid flow through the cylinder (320). The hydraulic cylinder (320) may include a first variable volume chamber and a second variable volume chamber (not shown). The volume of each chamber changes as the piston assembly (310) slides within the hydraulic cylinder (320). The volume may be further dependent on the diameter of the piston assembly (310) and its travel length. In some variations, a volume of the hydraulic cylinder chamber (i.e., first and second variable volume chambers) may be between about 9 ml and about 30 ml. For example, the volume of the hydraulic cylinder chamber may be between about 15 ml and about 20 ml.

FIG. 3C is a cross-sectional side view of the hydraulic assembly (300) comprising the piston assembly (310), hydraulic cylinder (320), and hydraulic damper (330). As discussed in more detail herein, the fluid circuit may further comprise a set of fluid channels coupled to the valve (332) (e.g., a variable-resistance three-port valve) and be configured to set a variable resistance to flow through the set of fluid channels. The fluid sump (340) (e.g., accumulator) may be coupled in-line with the fluid circuit (e.g., arranged along the same longitudinal axis). The hydraulic damper (330) may be parallel and attached to a side of the hydraulic cylinder (320) (e.g., laterally offset from a longitudinal axis of the hydraulic cylinder (320)). The hydraulic damper (330) may be attached to the hydraulic cylinder (320) along a length of the cylinder (320). Accordingly, a length of the hydraulic assembly (300) may be shortened and/or made more compact (relative to a hydraulic assembly having a cylinder and damper arranged in-line with each other) such that a prosthesis using the hydraulic assembly (300) may accommodate a larger patient population.

In some variations, the piston assembly (310) may comprise a diameter of between about 20 mm and about 30 mm, and a length of between about 8 mm and about 30 mm. For example, the diameter may be between about 22 mm and about 27 mm and the length may be between about 10 mm and about 20 mm. The hydraulic damper (330) may comprise a fluid circuit including the valve (332), valve spool (334), and fluid sump (340). The fluid sump (340) (e.g., accumulator) may comprise a spring (342), sleeve (344), a fluid sump piston (348), a seal (346) coupled to the piston (348), and a fluid reservoir (not shown). Additionally or alternatively, the fluid sump (340) may comprise a pneumatic element (e.g., using nitrogen gas) to change a reservoir volume of the fluid sump (340). The fluid sump (340) may be used to receive fluid as a result of piston (310) compression and high temperatures.

In some variations, the fluid sump (340) may comprise a diameter of between about 8 mm and about 30 mm, a length of between about 2 mm and about 60 mm. In some variations, the spring (342) may have an uncompressed length of between about 5 mm and about 120 mm. For example, the spring (342) may have an uncompressed length of between about 30 mm and about 50 mm. In some variations, the spring (342) may have a spring rate of between about 0.2 N/mm and about 10 N/mm. For example, the spring (342) may have a spring rate of between about 0.3 N/mm and about 1 N/mm. In some variations, the fluid sump piston (348) may comprise a diameter of between about 8 mm and about 30 mm and a length of between about 5 mm and about 40 mm. For example, the fluid sump piston (348) may comprise a diameter of between about 15 mm and about 25 mm and a length of between about 15 mm and about 30 mm. In some variations, the fluid reservoir may comprise a volume of between about 1.0 ml and about 50.0 ml. For example, the fluid reservoir may comprise a volume of between about 1.0 ml and about 10.0 ml with a fluid volume of between about 1.0 ml and about 3 ml.

As shown in FIG. 3C, the hydraulic cylinder (320) may comprise a slidable piston assembly (310), a first mount (312) coupled to the piston assembly (310), a second mount (322) coupled to an end of the hydraulic cylinder (320) opposite the first mount (312), and a piston seal (316) coupled to a piston sleeve (318). The piston assembly (310) may comprise a bumper (324) and one or more bushings (326). For example, a first bushing (326) may be coupled to the piston assembly (310) within an internal volume of the hydraulic cylinder (320) and a second bushing (not shown) may be disposed on exterior portion of the hydraulic cylinder (320) and the piston assembly (310). A wiper (329) may be slidably coupled to the piston assembly (310) at an end portion of the hydraulic cylinder (320).

Figure 4:
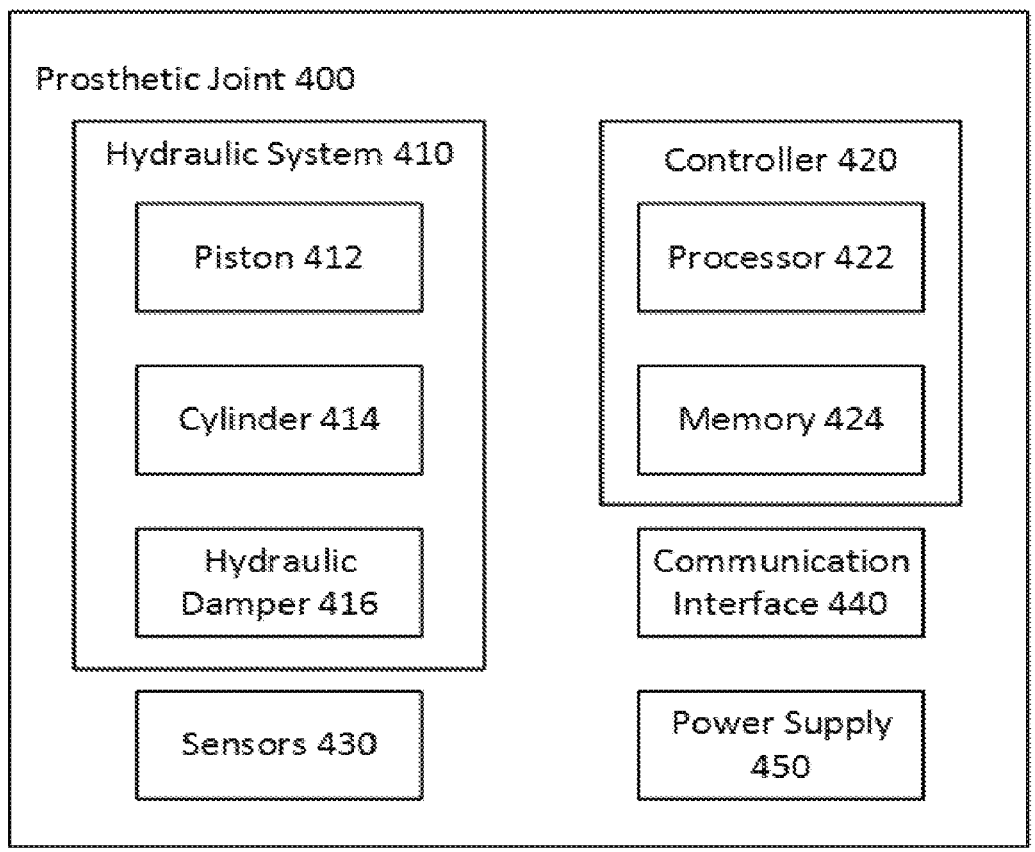
FIG. 4 is a block diagram of a variation of a prosthetic joint.

FIG. 4 is a block diagram of a variation of a prosthetic joint (400) having a control scheme to automate control of resistance to rotation of the prosthetic joint (400) and may be used in any of the prosthetic knees (100, 200) described herein. The prosthetic joint (400) may include a hydraulic system (410) used to set the resistance to rotation of the prosthetic joint (400). The hydraulic system (400) may function as a hydraulic actuator or damper and be configured to control the flow of hydraulic fluid, and thus the rotation of the prosthetic joint (400). The hydraulic system (410) may include a piston (412), a hydraulic cylinder (414), and a hydraulic damper (416) configured to permit, limit, and/or resist movement of hydraulic fluid within the hydraulic system (410), and thus permit, limit, and/or resist rotation of the prosthetic joint (400). In some variations, the hydraulic damper (416) may include a hydraulic actuator having a motor that generates hydraulic pressure to drive rotation of the joint (400). The hydraulic actuator may also be operated as a damper.

In some variations, the hydraulic system (410) may be controlled by a controller (420) using one or more sensors (430). The controller (420) may include one or more processors (422) and memory (424). The processor (422) may be any suitable processing device configured to run and/or execute a set of instructions or code and may include one or more data processors, image processors, graphics processing units, physics processing units, digital signal processors, and/or central processing units. The processor (422) may be, for example, a general purpose processor, Field Programmable Gate Array (FPGA), an Application Specific Integrated Circuit (ASIC), and/or the like. The processor (422) may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some variations, the memory (424) may include a database (not shown) and may be, for example, a random access memory (RAM), a memory buffer, a hard drive, an erasable programmable read-only memory (EPROM), an electrically erasable read-only memory (EEPROTv1), a read-only memory (ROM), Flash memory, etc. The memory (424) may store instructions to cause the processor (422) to execute modules, processes and/or functions associated with the system (400), such as hydraulic fluid control, gait determination, stumble recovery, sensor control, communication, and/or user settings.

The prosthetic joint (400) may include one or more sensors (430) including, but not limited, to an inertial measurement unit (IMU) (e.g., discrete integrated circuit), angle position sensor, differential pressure sensor, torque sensor, load sensor, and temperature sensor.

An IMU may be provided and may be configured to measure linear and angular accelerations along three axes. For example, absolute tilt may be measured and used to set a mode (e.g., walking, cycling) that the joint should be in. In some variations, an IMU may be disposed on and/or coupled to a rotor and/or shank of the prosthetic joint. The IMU may comprise an accelerometer and/or gyroscope. In some variations, an accelerometer of the IMU may have a resolution of at least about 4.8 cm/s$^2$, an accuracy of about ±39 cm/s$^2$, and a measurement range between about ±16 g. A gyroscope of the IMU may have a resolution of at least about 0.07 degrees/second, an accuracy between about ±3 deg/sec, and a measurement range between about ±2000 deg/sec.

An angle position sensor may be disposed on and/or coupled to a. rotor and/or shank. The angle position sensor may be configured to classify the orientation of the knee. The angle may be used to calculate a torque of the knee. In some variations, the angle position sensor may be a Hall sensor, an optical encoder, or other angle position sensor. In some variations, the angle sensor may have a resolution of at least about 0.025 degrees/count, and accuracy less than about 1 degree, and may measure flexion between about 0 degrees and about 135 degrees.

A differential pressure sensor may be configured to measure differential pressure in the hydraulic system. In some variations, a torque of the knee may be calculated using a differential pressure and knee angle. In some variations, the differential pressure sensor may be a strain gauge coupled to a piston and/or cylinder. In some variations, knee torque may be calculated using an external torque sensor disposed on the proximal connector, rotor, shank, or combined with a load sensor at the distal end of the prosthetic joint.

In some variations, a load transducer (e.g., a strain gauge) may be disposed on or in the piston shaft or the connecting elements of the piston shaft. A load sensor may be configured to measure a load of the prosthetic joint (400). For example, the load sensor may be configured to measure the deflection of a compliant element. In some variations, the load sensor may be a strain gauge disposed in a distal connector and/or rotor. Tn some variations, load and/or torque sensors may be used to determine toe-off thresholds and user loading of the knee. In some variations, the load sensor may have a resolution of at least about 0.31 N/count, an accuracy of less than about 4.5 N, and may measure a load between about 0 N and about 2000 N. In some variations, the torque sensor may have a resolution of at least about 0.025 Nm/count, an accuracy of less than about 0.125 Nm, and may measure a torque between about 0 N and about 101 Nm.

A temperature sensor may be disposed on or be adjacent to the hydraulic system (410) and/or electronic components of the system (e.g., controller (420), communication interface (440), power supply (450)) to ensure safe operation of the prosthetic joint (400).

Figure 12:
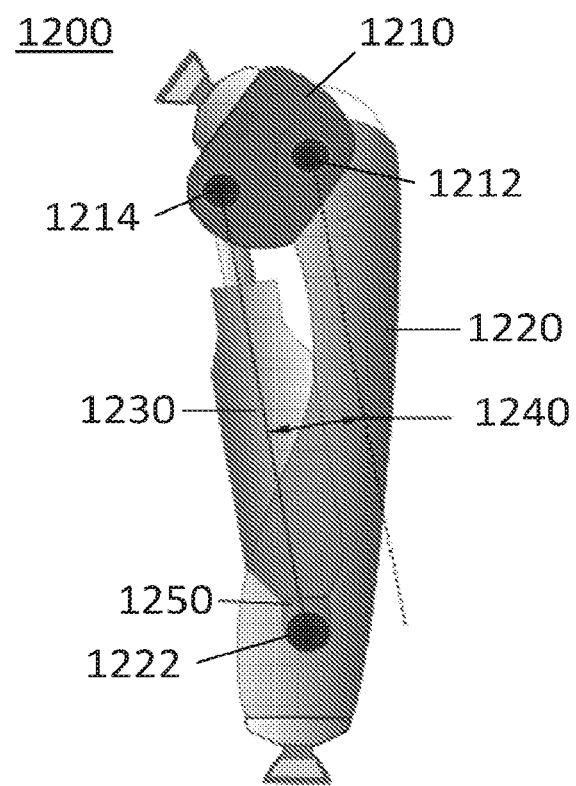
FIG. 12 is a schematic side view of another variation of a prosthetic knee.

FIG. 12 is a schematic side view of another variation of a prosthetic knee (1200). The prosthetic knee (1200) may include an upper joint member (1210) rotatably coupled to a lower joint member (1220) about a first pivot (1212). A hydraulic system (1230) may be pivotally coupled to the upper joint member (1210) at a first mount (1214) and coupled to the lower joint member (1220) at a second mount (1222). In some variations, the upper joint member (1210) may comprise a magnet, such as a samarium-cobalt magnet that may be configured to be diametrically polarized and provide temperature compensation. The prosthetic knee (1200) may comprise a load cell (1250) located in parallel with and at a distal end of the hydraulic system (1230). For example, the load cell (1250) may be located in one or more of the second mount (1222), piston shaft, and/or cylinder. In some variations, one or more pressure gauges or sensors located internally in, or in fluid communication with, the cylinder may be used to measure an absolute pressure(s) or the differential pressure in the cylinder between its chambers. The differential pressure may be used to calculate a load on the cylinder. Knee torque may be calculated using the measured load on the cylinder and a moment arm of the cylinder. A moment arm of the cylinder may be calculated from a knee angle measurement.

In variations where the prosthesis is a prosthetic ankle, one or more sensors may comprise a force or load sensor, torque sensor, angle sensor, accelerometer, and/or gyroscope. The sensors may be located on the prosthetic ankle and/or artificial foot. For example, a force or load sensor, a torque sensor, or both, may be located on a shank or a connector and configured to measure force, torque, or both applied by the user to the prosthetic ankle and/or artificial foot. As another example, an angle sensor may be located on an ankle shaft of the pivot between the shank and the artificial foot to measure a relative angle between the shank and the artificial foot. As another example, an accelerometer, a gyroscope, or both may be located on a foot coupler mount or the artificial foot and configured to sense or measure impact, orientation, etc. Similarly, locating an angle sensor between the shank and the artificial foot may allow relative orientation to be classified without having to classify a relative orientation of other structure, such as a pylon, and without having to locate sensors on a pylon. In some variations, the system may comprise one or more of the elements described in U.S. patent application Ser. No. 13/015,423, filed on Jan. 27, 2011, and titled "COMPACT AND ROBUST LOAD AND MOMENT SENSOR," the content of which is hereby incorporated by reference in its entirety.

Referring back to FIG. 4, in some variations, the prosthetic joint (400) may comprise a communication interface (440) including a transceiver (not shown). The controller (420) may use the communication interface (440) to wirelessly connect to an external computing device including, but not limited, to a tablet computer, a laptop computer, a desktop computer, a smart phone, or the like. Patient data from memory (424) may be received by communication interface (440) and output to the external device. As another example, the communication interface (440) may comprise one or more input devices on the prosthetic joint (400) including one or more buttons, knobs, dials, switches, or the like.

The prosthetic joint (400) may include a power supply (e.g., batteries). The hydraulic damper (416), controller (420), sensors (430), and communication interface (440) may be coupled to the power supply (450) to receive power. In some variations, the power supply (450) may be disposed within a housing of the prosthetic joint (400) and/or connected externally to the prosthetic joint (400) via, for example, a power cable. As another example, the power supply (450) may be disposed on a backside of the prosthetic joint (400) and coupled to the hydraulic system (410).

In some variations, the systems may comprise one or more elements described in U.S. patent application Ser. No. 14/707,957, filed on May 8, 2015, and titled "PROSTHETIC WITH VOICE COIL VALVE," and/or U.S. patent application Ser. No. 14/466,081, filed on Aug. 22, 2014, and titled "MICROPROCESSOR CONTROLLED PROSTHETIC ANKLE SYSTEM FOR FOOTWEAR AND TERRAIN ADAPTATION," each of which is hereby incorporated by reference in its entirety.

B. Hydraulic Circuit

In some variations, a hydraulic assembly or system may comprise a single-ended piston, a double-acting cylinder (e.g., providing variable resistance in both directions) coupled to a fluid circuit having a single unidirectional control valve. The single unidirectional control valve may set resistance to hydraulic fluid flow in both flexion (e.g., cylinder compressing) and extension (e.g., cylinder extending). The control valve may be unidirectional in that the fluid circuit ensures fluid flow in a single direction into the control valve for both compression and extension. The hydraulic assemblies described herein may be provided for use with a limb prosthesis, orthotic, assistive device, or robotic linkage.

Figure 5A:
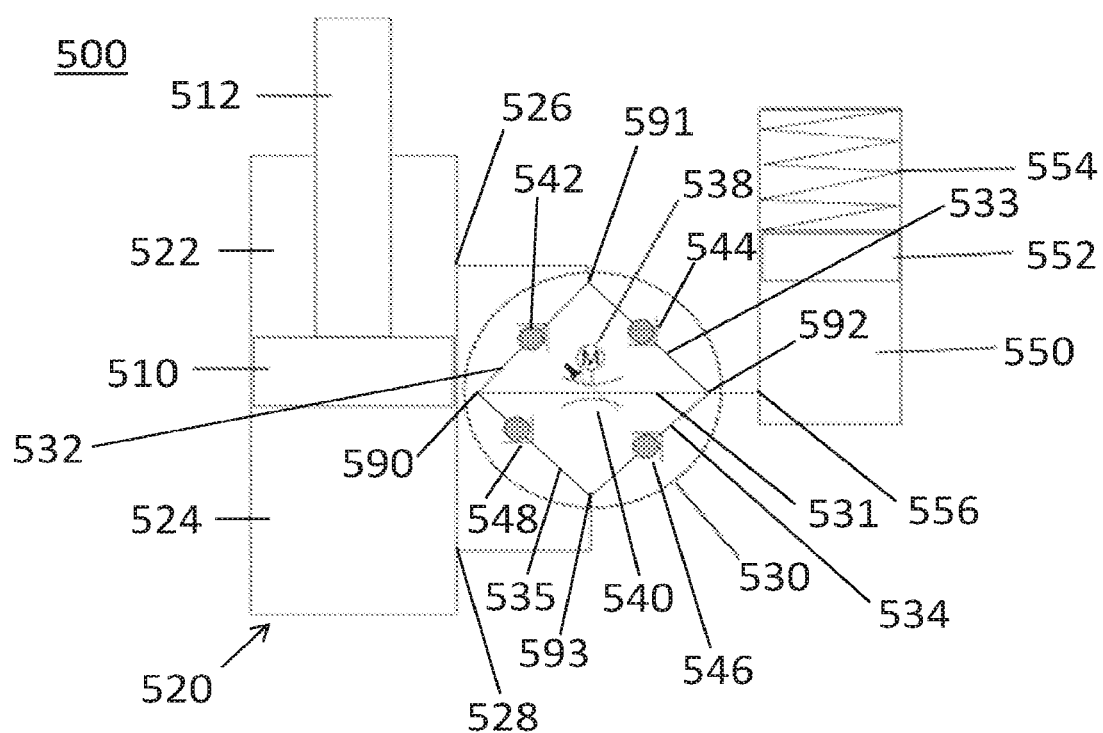
FIGS. 5A-5C are illustrative schematic diagrams of a variation of a hydraulic system.

FIG. 5A illustrates a hydraulic assembly (500) including a first piston (510), hydraulic cylinder (520), and a hydraulic fluid flow circuit (530). The piston (510) may be slidable within a hydraulic cylinder (520). A piston shaft (512) coupled to the piston (510) may compress or extend the piston (510) into and out of the cylinder (520). The piston (510) may structurally separate the cylinder (520) into a first chamber (522) and an opposing second chamber (524). The first chamber (522) may include a first cylinder port (526) and the second chamber (524) may include a second cylinder port (528). In some variations, the first and second cylinder ports (526, 528) may be located on a sidewall of the cylinder (520) on opposite sides of the piston (510). In some variations, the first cylinder port (526) may be located at a first end of the cylinder (520) while the second cylinder port (528) may be located at a second end of the cylinder (520) opposite the first end.

The fluid circuit (530) may be coupled to the hydraulic cylinder (520) through the first and second cylinder ports (526, 528) such that the fluid circuit (530) may be configured to control a resistance of hydraulic fluid through the hydraulic assembly (500). The fluid circuit (530) may include a plurality of hydraulic fluid channels configured to control hydraulic fluid flow between the first chamber (522), the second chamber (524), and a fluid sump (550). FIG. 5A illustrates the fluid circuit (530) comprising a plurality of hydraulic fluid channels. A first hydraulic fluid channel (531) may comprise a first channel inlet (580) (labeled in FIG. 5B), a first channel outlet (581), and a first channel valve (540) configured to set a variable resistance to flow through the first fluid channel (531). In some variations, the first channel valve (540) may be a unidirectional variable-resistance valve. A second fluid channel (532) may comprise a second channel inlet (582) (labeled in FIG. 5C), a second channel outlet (583), and a second channel valve (542). A third fluid channel (533) may comprise a third channel inlet (584) (labeled in FIG. 5B), a third channel outlet (585), and a third channel valve (544). A fourth fluid channel (534) may comprise a fourth channel inlet (586) (labeled in FIG. 5C), a fourth channel outlet (587), and a fourth channel valve (546). A fifth fluid channel (535) may comprise a fifth channel inlet (588) (labeled in FIG. 5B), a fifth channel outlet (589), and a fifth channel valve (548).

In some variations, a first interconnection (590) (e.g., intersection) may comprise the first channel inlet (580), the second channel outlet (583), and the fifth channel outlet (589). A second interconnection (591) may comprise the first cylinder port (526), the second channel inlet (582), and the third channel outlet (585). A third interconnection (592) may comprise a sump port (556), the third channel inlet (584), and the fourth channel inlet (586). A fourth interconnection (593) may comprise the second cylinder port (528), the fourth channel outlet (587), and the fifth channel inlet (588). In some of these variations, the second interconnection (591) may comprise a first bi-directional channel. For example, the first bi-directional channel may extend from the first cylinder port (526) to the second interconnection (591). The third interconnection (592) may comprise a second bi-directional channel. For example, the second bidirectional channel may extend from the third interconnection (592) to the first sump port (556). The fourth interconnection (593) may comprise a third bi-directional channel. For example, the third bi-directional channel may extend from the fourth interconnection (593) to the second cylinder port (528).

In some variations, the first channel inlet (580) may be connected between the second channel valve (542) and the fifth channel valve (548). The first cylinder port (526) may be connected between the second channel valve (542) and the third channel valve (544). A sump port (556) may be connected between the third channel valve (544) and the fourth channel valve (546). The second cylinder port (528) may be connected between the fourth channel valve (546) and the fifth channel valve (548). The second channel valve (542) and fifth channel valve (548) may be connected in series. The third channel valve (544) and fourth channel valve 546) may be connected in series. The second channel valve (542) and the third channel valve (544) may be connected in parallel. The fourth channel valve (546) and the fifth channel valve (548) may be connected in parallel. A first channel inlet (580) of the first hydraulic fluid channel (531) may be connected between the second and fifth fluid channels (532, 535). A first channel outlet (581) of the first hydraulic fluid channel (531) may be connected between the third and fourth fluid channels (533, 534).

The first valve (540) may be configured to set a resistance to flow of hydraulic fluid through the first hydraulic fluid channel (531). The fluid circuit (530) may be configured such that hydraulic fluid flows into the first hydraulic fluid channel (531) in the same direction for both extension and compression of the piston (510). Therefore, the first valve (540) may comprise a unidirectional control valve rather than a bi-directional valve. The first valve (540) may be a control valve such as a proportional directional control valve. In some variations, the first valve (540) may comprise one or more of a voice coil valve, solenoid valve, and DC motor. The first valve (540) may have a rotary or linear geometry. In some variations, resistance of the first valve (540) may be determined based upon input from one or more of the sensors (e.g., mechanical sensor) as described in more detail herein. In some variations, the second through fifth valves (542, 544, 546, 548) may be check valves configured to permit hydraulic fluid flow in a single direction.

In some variations, an actuator (538) may be coupled to the first valve (540). The actuator (538) may be configured to bi-directionally drive the first valve (540) to reciprocally and selectively position the first valve (540) to control fluid flow based on the polarity of the current applied to the actuator (538). Thus, the first valve (540) may be bi-directionally driven by the actuator (538).

The first valve (540) may include a sleeve having an orifice and a spool movable within the sleeve. The actuator (538) may be coupled to the first valve (540) to move the spool with respect to the orifice of the sleeve to vary a resistance to fluid flow through the valve (540). In some variations, the actuator (538) may move a spool with respect to the orifice. Thus, the first valve (540) may be configured to set the resistance of fluid through the fluid circuit (530). As described in more detail herein, the check valves may be configured such that fluid is permitted or resistant to flow through different fluid channels in response to compression and extension of the piston (510).

The fluid circuit (530) may be connected to a fluid sump (550). In some variations, the fluid sump (550) may comprise a second piston (552) and a spring (554). The fluid sump (550) may comprise a cavity that serves as a reservoir for hydraulic fluid displaced by movement of the piston (510) in the cylinder (520). The spring (554) may be configured to generate a spring force that acts on the second piston (552) as the volume of the cavity increases with increased fluid volume, thereby creating an internal pressure that acts equally on both sides of the second piston (552). Since the pressure area is not equal on both sides of the second piston (552), the net force acting on the second piston (552) is non-zero and may tend to push the piston shaft (51.2) out of the cylinder (520) resulting in a linear cylinder spring rate. The cylinder spring rate may correspond to swing extension assistance that may assist extension of the knee.

The actuator (538) and first valve (540) may be coupled to a controller, such as controller (420) described herein. The controller may be configured to control actuator (538) and first valve (540), to thereby control a resistance of fluid flow through the hydraulic assembly (500), and thus the resistance to rotation of the prosthesis. For example, resistance of the first valve (540) may be determined based upon input from one or more of the sensors as described in more detail herein. Accordingly, compression and extension of the hydraulic assembly (500) may be modified during the gait cycle of a prosthetic knee, and thus control of the compression (flexion) and extension of a prosthetic joint during gait.

Figure 5B:
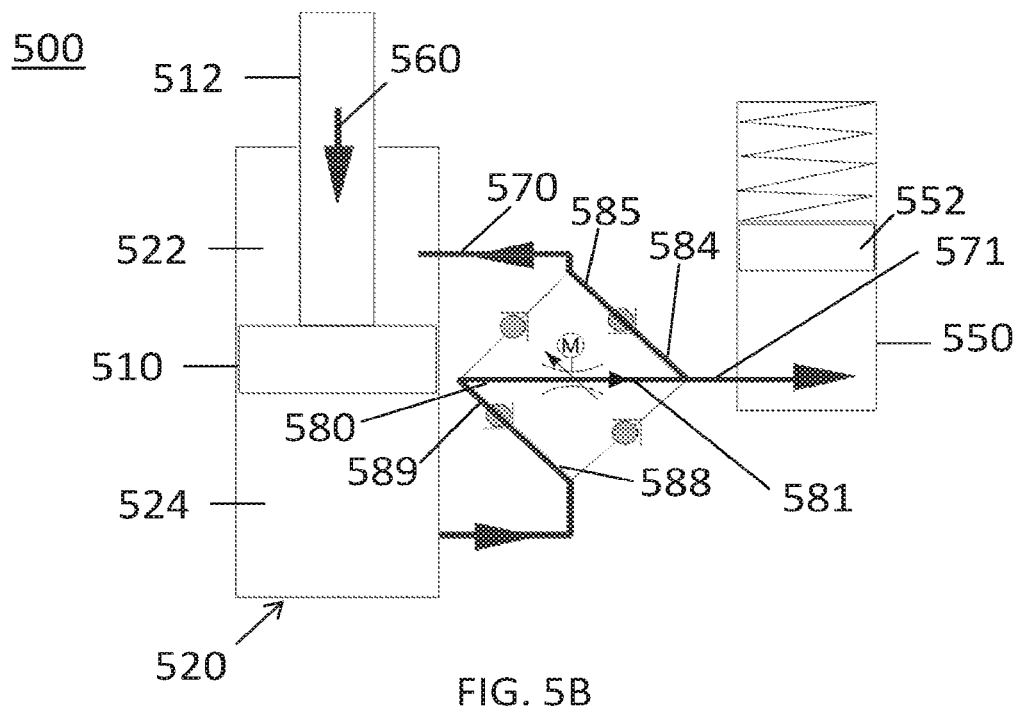

FIG. 5B illustrates hydraulic fluid flow through the hydraulic assembly (500) in response to compression (560) of the piston (510) such as in response to a first state of a prosthetic knee (e.g., flexion state). For example, as the piston (510) reduces a volume of the second chamber (524) of the cylinder (520), hydraulic fluid may be permitted to enter the fluid circuit (530) through the second cylinder port (528) and exit out of the first cylinder port (526). As illustrated in FIG. 513, the fluid circuit (530) may be configured to permit hydraulic fluid flow along a first fluid path (570) sequentially through the second cylinder port (528), the fifth channel valve (548), the first valve (540) (e.g., variable-resistance valve), the third channel valve (544), and into the first cylinder port (526). In some variations, the flexion state may be configured to permit fluid flow along a second fluid path (571) from the first valve (540) into the sump port (556). In this manner, fluid may flow into and be held in the fluid sump (550) so as to displace the second piston (552). In some of these variations, the flexion state may be configured to permit fluid flow simultaneously in the first and second fluid paths (570, 571).

In some variations, the flexion state may be configured to resist fluid flow through the second channel valve (542) and the fourth channel valve (546). For example, the second and fourth channel valves (542, 546) may be check valves configured to resist flow received from a channel outlet (589) of the fifth check valve (548) and the second cylinder port (528), respectively. Conversely, the fifth check valve, first control valve, and third check valves (548, 540, 544) may be configured to allow fluid flow from the second cylinder port (528), a channel outlet (589) of the fifth check valve (548), and a channel outlet (581) of the first valve (540), respectively. Thus, hydraulic fluid flow may be configured to flow from the second chamber (524) through the hydraulic circuit (530) and fluid sump (550) and into the first chamber (522).

Figure 5C:
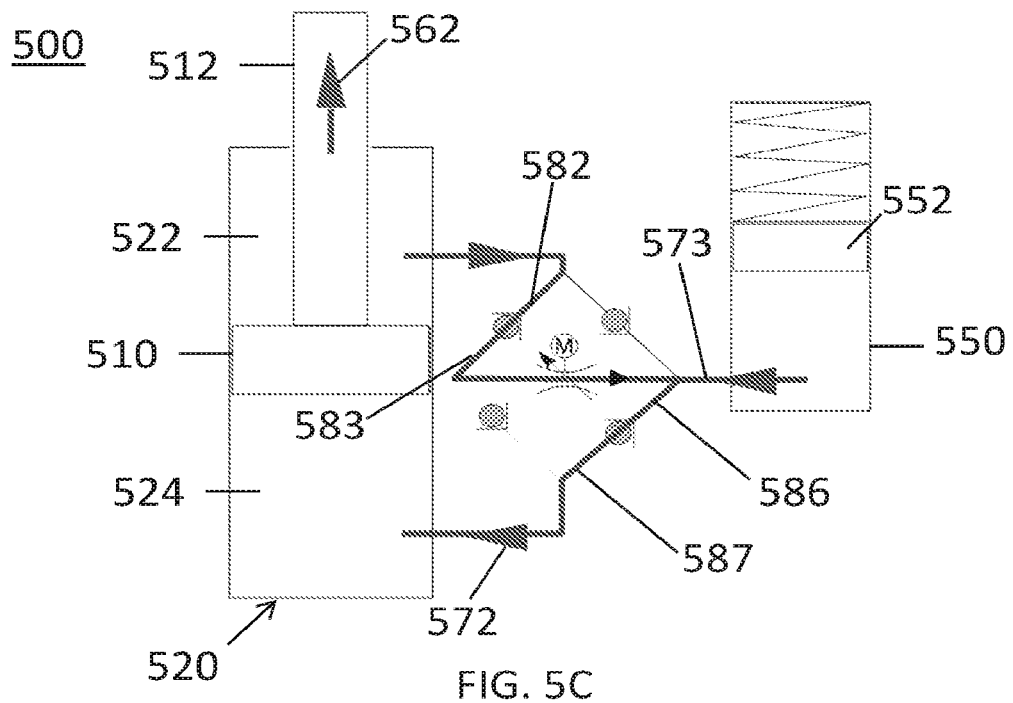

FIG. 5C illustrates hydraulic fluid flow through the hydraulic assembly (500) in response to extension of the piston (510) such as in response to a second state of a prosthetic knee (e.g., extension state). For example, as the piston (510) reduces a volume of the first chamber (522) of the cylinder (520), hydraulic fluid may enter the fluid circuit (530) through the first cylinder port (526) and exit out of the second cylinder port (528). As illustrated in FIG. 5C, the fluid circuit (530) may be configured to permit hydraulic fluid flow along a third fluid path (572) sequentially through the first cylinder port (526), the second channel valve (542), the first valve (540) (e.g., variable-resistance valve), the fourth channel valve (546), and into the second cylinder port (528). In some variations, the extension state may be configured to permit fluid flow along a fourth fluid path (573) sequentially from the sump port (556) to the fourth channel valve (546). In this manner, fluid may flow out of the fluid sump (550) so as to displace the second piston (552). In some of these variations, the extension state may be configured to permit fluid flow simultaneously in the third and fourth fluid paths (572, 573).

In some variations, the extension state may be configured to resist fluid flow through the third channel valve (544) and the fifth channel valve (548). The third and fifth channel valves (544, 548) may be check valves configured to resist flow received from the first cylinder port (526) and a channel outlet (583) of the second check valve (542), respectively. Conversely, the second check valve, first control valve, and fourth check valves (542, 540, 546) may be configured to allow fluid flow from the first cylinder port (526), a channel outlet (583) of the second check valve (542), and an outlet of the first valve (540), respectively. Thus, hydraulic fluid flow may be configured to flow from the first chamber (522) through the hydraulic circuit (530) and fluid sump (550) and into the second chamber (524).

C. Control Valve

The hydraulic systems described herein may include a control valve configured to set a rate of fluid flow through a fluid circuit or hydraulic assembly by variably setting an area of an opening through which fluid flows. In some variations, a valve may comprise a sleeve having one or more orifices through which fluid may flow and a spool that slidably moves within the sleeve to further set the area of fluid flow through the orifice. The control valves described herein may be provided for use with a hydraulic assembly, limb prosthesis, orthotic, assistive device, or robotic linkage. FIG. 6A is a cross-sectional side view of a valve (600) comprising a sleeve (610) and a spool (620). The valves disclosed herein may be driven by a valve actuator. The spool (620) may be slidable within a first lumen (612) of the sleeve (610) and may be driven by an actuator (not shown) such as a voice coil actuator, solenoid actuator, or other actuator (e.g., DC brushless motor). The sleeve (610) may have an inner diameter D. The spool (620) may define a second lumen (622). The sidewalls of the sleeve (610) may define an orifice (614) having length L. As the spool (620) slides through the sleeve (610), portions of the spool (620) may overlap portions of the orifice (614) such that an open length of the orifice (614) may be defined as $L_o$. FIG. 6B is a side view of the sleeve (610) illustrating the orifice (614) depicted in FIG. 6A as having a width W. The orifice (614) may have an oblong shape (e.g., obround) as shown in FIG. 6B. However, the shape of the orifice (614) is not particularly limited. In some variations, the orifice (614) may have a length L and $L_o$ between about 0.5 mm and about 10.0 mm, an inner diameter D between about 2 mm and about 10 mm, and a width W of between about 0.025 mm and about 0.5 mm. For example, the length L and $L_o$ may be between about 2 mm and about 5 mm, the inner diameter D may be between about 2 mm and about 5 mm, and the width W may be between about 0.05 mm and about 0.2 mm.

Figure 6F:
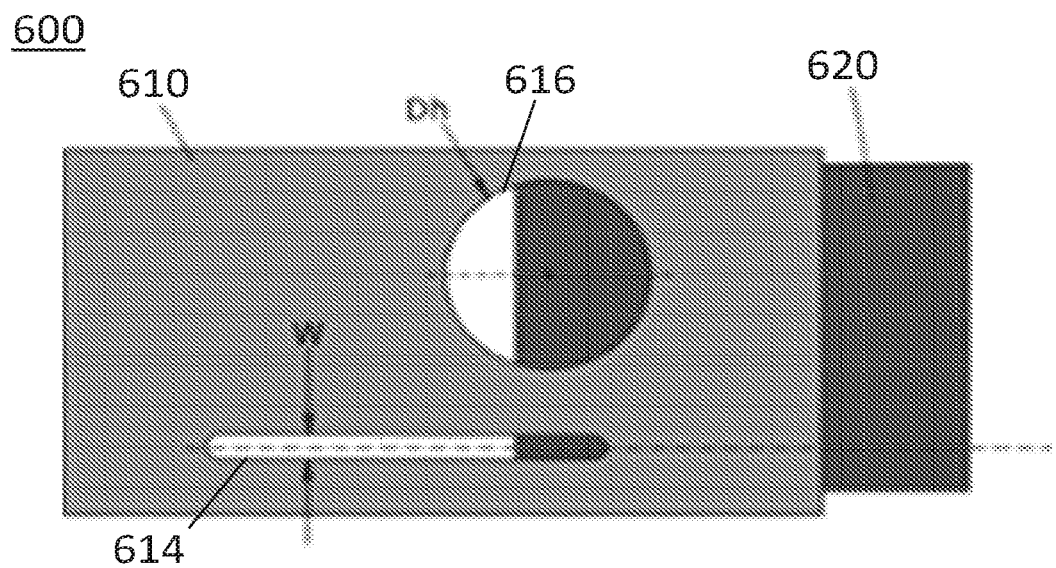

As shown in FIG. 6F, a plurality of orifices (614, 616) (e.g., slits, holes) of varying shapes and sizes may be disposed radially about a circumference of the sleeve (610). In some variations, the number of orifices may be between 1 and 12. For example, the sleeve (610) may comprise 4 orifices. A second orifice (616) may comprise a diameter Dh of between about 0.5 mm and about 6 mm. For example, the diameter Dh may be between about 1.0 mm and about 3 mm. In some variations, the area of an orifice may be between about 5 $mm^2$ and about 20 $mm^2$. For example, the area of an orifice may be between about 10 $mm^2$ and about 15 $mm^2$.

The valve (600) depicted in FIG. 6A may be configured to linearly slide the spool (620) within the sleeve (610). The orifice area of the valve (600) may be a function of a linear position of the spool (620) as controlled by a valve actuator. In other variations, the spool (620) may move within the sleeve (610) in a rotary manner. In these variations, the orifice area of the valve (600) may be a function of an angular rotation of spool (620) relative to the orifice (614) as controlled by a valve actuator. Different actuation mechanisms exhibit varying performance characteristics including response rate, power consumption, size, cost, complexity, and the like. In some variations, a voice coil actuator may be coupled either directly or through one or more flexible elements to a linear spool valve. Power to a voice coil actuator may be required to maintain a specific valve position. In some variations using a voice coil actuator, the valve may comprise a spring to set a power OFF valve position when the actuator is in a power OFF state.

In some variations, the voice coil actuator may include a permanent magnet and a coil movable with respect to each other. The permanent magnet may generate a magnetic field in which the coil moves when a current is applied to the coil. In other variations, the coil may remain stationary as the magnet moves when a current is applied. The amount of current applied may correspond to a position of the coil with respect to the magnet. The polarity of the current may correspond to a direction of travel of the coil with respect to the magnet. For a voice coil actuator, the force produced may be proportional and substantially linear to the current applied such that the velocity of the coil may be proportional to the voltage applied. Thus, the voice coil actuator may have a substantially linear time and force response. A direction of movement of the coil may correspond to a polarity of the current. In some variations, a voice coil actuator, and thus the voice coil control valve, may have a rapid response rate (i.e. greater than 100 cycles per second), and a low power consumption (i.e. less than 1.8 Watts, or 150 mAmps at 12V). Such an actuator and/or valve may be referred to herein as a voice coil or voice coil valve.

In some variations, a solenoid valve may comprise a stationary iron core with a coil and a movable iron armature. The armature may be configured to move when current is applied to the coil. A solenoid actuator may further comprise a spring configured for return movement when current is removed from the coil. A solenoid actuator may operate unidirectionally and against a return spring. Due to the spring return, the response time of the valve in the return direction may be proportional to the spring rate. Therefore, a stiff spring may be provided to achieve fast response times. An armature force must overcome this spring force to stay at any given valve position. Therefore, the amount of power required to hold a valve position may increase proportionally to decreasing response times of the valve. Solenoid valves may therefore provide ON/OFF operation and may be non-linear (e.g., generate force proportional to the square of the current).

In some variations, a valve actuator may comprise a brushless DC motor. The motor may be coupled to a linear valve using a screw or a rotary valve either directly or indirectly through a transmission system. The hydraulic assemblies disclosed herein may use any suitable valve actuator. Fluid flow through a valve (600) will be described with respect to the cross-sectional side views depicted in FIGS. 6C-6E. In FIG. 6C, the spool (620) is at a first spool position (650) within the sleeve (610). At the first spool position (650), fluid flows at a first volumetric flow rate Qi from an area having a higher first pressure $P_1$ through a first lumen (612) to an area having a lower second pressure $P_2$. The spool (620) overlaps only a small portion of the orifice (614) such that there is a relatively low level of resistance to fluid flow such that an amputee may experience a corresponding low level of resistance to joint rotation.

In FIG. 6D, the spool (620) is at a second spool position (650) within the sleeve (610). At the second spool position (652), fluid flows at a second volumetric flow rate $Q_2$ from an area having a higher first pressure $P_1$ through a first lumen (612) to an area having a lower second pressure $P_2$. The second volumetric flow rate $Q_2$ is less than the first volumetric flow rate $Q_1$. The spool (620) overlaps a significant portion of the orifice (614) such that there is a relatively intermediate and/or high level of resistance to fluid flow such that an amputee may experience a corresponding intermediate and/or high level of resistance to joint rotation. In some variations, the first flow rate $Q_1$ may be up to about 40 ml/s and the second flow rate $Q_2$ may be up to about 40 ml/s.

In FIG. 6E, the spool (620) is at a third spool position (654) within the sleeve (610). At the third spool position (654), fluid does not flow through the valve (600). The orifice (614) is completely blocked by the spool (620). This condition may be referred to as lockout and corresponds to maximum resistance to fluid flow where the prosthetic joint may be fixed at a particular angle. In some variations, the first pressure $P_1$ may be up to about 4000 psi and the second pressure $P_2$ may be up to about 4000 psi.

D. Power OFF Resistance

For safety reasons, when a prosthesis such as a prosthetic knee is in a power OFF state, the prosthetic knee may be configured to have high resistance (e.g., stiff) in flexion while allowing for free or low resistance extension. In some variations, the power OFF flexion resistance may be configurable to accommodate different user preferences and weights. As described in more detail herein, power OFF resistance of a prosthetic knee may be implemented using a power OFF spool valve (e.g., ON/OFF spool valve) or a three-port valve (e.g., a proportional valve having an additional port).

1. Spool Valve

In some variations, the hydraulic circuit as described may comprise a primary control valve (e.g., voice coil valve) and a secondary ON/OFF spool valve including a bias spring and a user adjustable variable flow resistor. When the hydraulic assembly is powered (e.g., when a valve actuator is powered), a secondary power OFF valve may be configured to close and restrict flow through any of the secondary valve ports such that fluid flow bypasses the secondary power OFF valve. The primary control valve may be configured to be spring-biased to fully close the orifice under a power OFF state while the secondary valve may be configured to be spring-biased to filly open each of the secondary valve's ports, thereby allowing fluid flow through each of the ports. In a power OFF flexion state where the piston is compressed into the cylinder, fluid may be configured to flow through the user adjustable variable flow resistor. In a power OFF extension stale where the piston is extended from the cylinder, the variable flow resistor may be bypassed and the secondary valve may be configured to be fully open and allow unrestricted fluid flow. The spool valves described herein may be provided for use with a hydraulic assembly, limb prosthesis, orthotic, assistive device, or robotic linkage.

Figure 7A:
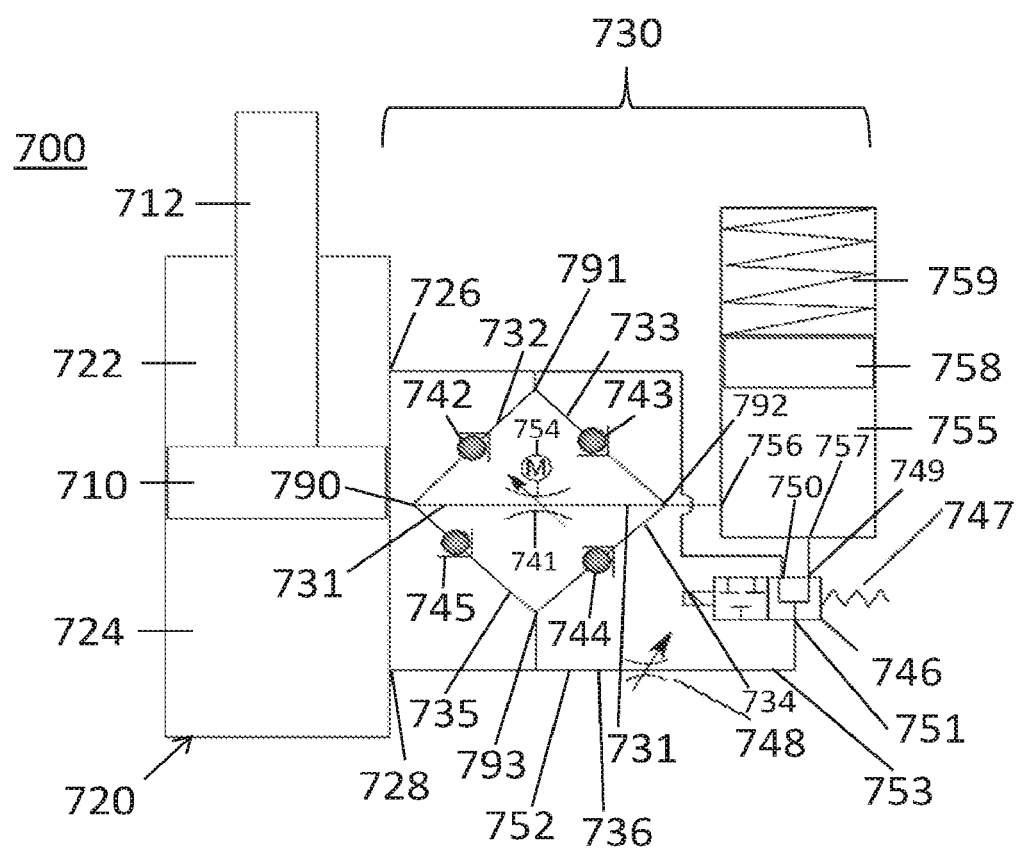
FIGS. 7A-7E are illustrative schematic diagrams of another variation of a hydraulic system.

FIG. 7A illustrates a hydraulic assembly (700) including a first piston (710) and hydraulic cylinder (720). The piston (710) may be slidable within the hydraulic cylinder (720). A piston shaft (712) coupled to the piston (710) may compress or extend the piston (710) into the cylinder (720). The piston (710) may structurally separate the cylinder (720) into a first chamber (722) and an opposing second chamber (724). The first chamber (722) may include a first cylinder port (726) and the second chamber (724) may include a second cylinder port (728). In some variations, the first and second cylinder ports (726, 728) may be located on a sidewall of the cylinder (720) on opposite sides of the piston (710). In some variations, the first cylinder port (726) may be located at a first end of the cylinder (720) while the second cylinder port (728) may be located at a second end of the cylinder (720) opposite the first end.

The fluid circuit (730) may be coupled to the hydraulic cylinder (720) through the first and second cylinder ports (726, 728) such that the fluid circuit (730) may be configured to control a resistance of hydraulic fluid through the hydraulic assembly (700). The fluid circuit (730) may include a plurality of hydraulic fluid channels configured to control hydraulic fluid flow between the first chamber (722), the second chamber (724), and a fluid sump (755). A first hydraulic fluid channel (731) may comprise a first channel inlet (780) (labeled in FIG. 7B), a first channel outlet (781), and a first channel valve (741) configured to set a variable resistance to flow through the first fluid channel (731). In some variations, the first channel valve (741) may be a unidirectional variable-resistance valve. A second fluid channel (732) may comprise a second channel inlet (782) (labeled in FIG. 7C), a second channel outlet (783), and a second channel valve (742). A third fluid channel (733) may comprise a third channel inlet (784) (labeled in FIG. 7B), a third channel outlet (785), and a third channel valve (743). A fourth fluid channel (734) may comprise a fourth channel inlet (786) (labeled in FIG. 7C), a fourth channel outlet (787), and a fourth channel valve (744). A fifth fluid channel (735) may comprise a fifth channel inlet (788) (labeled in FIG. 7B), a fifth channel outlet (789), and a fifth channel valve (745). A sixth fluid channel (736) may comprise a sixth channel inlet (752), a sixth channel outlet (753), and a first user-adjustable variable flow resistor (748).

In some variations, a first interconnection (790) (e.g., intersection) may comprise the first channel inlet (780), second channel outlet (783), and the fifth channel outlet (789). A second interconnection (791) may comprise the first cylinder port (726), the second channel inlet (782), and the third channel outlet (785). A third interconnection may comprise the sump port (756), the third channel inlet (784), and the fourth channel inlet (786). A fourth interconnection may comprise the second cylinder port (728), the fourth channel outlet (787), and the fifth channel inlet (788).

In some variations, the first channel inlet (780) may be connected between the second channel valve (742) and the fifth channel valve (745). The first cylinder port (726) may be connected between the second channel valve (742) and the third channel valve (743). A sump port (756) may be connected between the third channel valve (743) and the fourth channel valve (744). The second cylinder port (728) may be connected between the fourth channel valve (744) and the fifth channel valve (745). The second channel valve (743) and fifth channel valve (745) may be connected in series. The third channel valve (743) and fourth channel valve (744) may be connected in series. The second channel valve (742) and the third channel valve (743) may be connected in parallel. The fourth channel valve (744) and the fifth channel valve (745) may be connected in parallel. A first channel inlet (780) of the first hydraulic fluid channel (731) may be connected between the second and fifth fluid channels (732, 735). A first channel outlet (781) of the first hydraulic fluid channel (731) may be connected between the third and fourth fluid channels (733, 734).

In some variations, the first variable flow resistor (748) may be located between the third valve port (751) and the fourth interconnection (793) along a sixth fluid channel (736). The sixth fluid channel (736) may comprise a sixth channel inlet (752) at the fourth interconnection (793) and a sixth channel outlet (753) connected to the third valve port (751). In some variations, the first variable flow resistor (748) may comprise a unidirectional variable resistor configured to permit flow from the fourth interconnection (793) to the third valve port (751). The first variable flow resistor (748) may be configured to block fluid flow from the third valve port (751) to the fourth interconnection (793) regardless of whether the sixth valve (746) is open or closed.

The first valve (741) may be configured to set a resistance to flow of hydraulic fluid through the first hydraulic fluid channel (731). The fluid circuit (730) may be configured such that hydraulic fluid flows into the first hydraulic fluid channel (731) in the same direction for both extension and compression of the piston (710). Therefore, the first valve (741) may comprise a unidirectional control valve. The first valve (741) may be a control valve such as a proportional directional control valve. In some variations, the first valve (741) may comprise one or more of a voice coil valve, solenoid valve, and DC motor. The first valve (741) may have a rotary or linear geometry. In some variations, the second through fifth valves (742, 743, 744, 745) may be check valves configured to permit hydraulic fluid flow in a single direction.

In some variations, an actuator (754) may be coupled to the first valve (741). The actuator (754) may be configured to bi-directionally drive the first valve (741) to reciprocally and selectively position the first valve (741) based on the polarity of the current applied to the actuator (754). Thus, the first valve (741) may be bi-directionally driven by the actuator (754).

The first valve (74 I) may include a sleeve having an orifice and a spool movable within the sleeve. The actuator (754) may be coupled to the first valve (741) to move spool with respect to the orifice of the sleeve to vary a resistance to fluid flow through the first valve (741). In some variations, the actuator (754) may move a spool with respect to the orifice. Thus, the first valve (741) may be configured to set the resistance of fluid through the fluid circuit (730). As described in more detail herein, the check valves may be configured such that fluid flows through different fluid channels under compression and extension of the piston (710).

The fluid circuit (730) may be connected to a fluid sump (755). In some variations, the fluid sump (755) may comprise a second piston (758) and a second spring (759). The fluid sump (755) may comprise a cavity that serves as a reservoir for hydraulic fluid displaced by movement of the piston (710) in the cylinder (720). The fluid sump (755) may comprise a first sump port (756) and a second sump port (757). The second spring (759) may be configured to generate a spring force that acts on the second piston (758) as the volume of the cavity increases with increased fluid volume, thereby creating an internal pressure that acts equally on both sides of the second piston (758). Since the pressure area is not equal on both sides of the second piston (758), the net force acting on the second piston (758) is non-zero and may tend to push the piston shaft (712) out of the cylinder (720) resulting in a linear cylinder spring rate. The cylinder spring rate may correspond to swing extension assistance that may assist extension of the knee.

In some variations, the hydraulic circuit (730) may comprise a sixth valve (746) (e.g., power OFF spool valve) that may be a three-way or three-port valve that is normally open. In some variations, the sixth valve (746) may comprise a first spring (747), a first valve port (749), a second valve port (750), and a third valve port (751). The sixth valve (746) may be configured to permit fluid passage between the first, second, and third valve ports (749, 750, 751) when open, and block fluid passage between the first, second, and third valve ports (749, 750, 751) when closed. The first valve port (749) may be connected to the fluid sump (755) at the second sump port (757). The second valve port (750) may be connected to the second interconnection (791), and the third valve port (751) may be connected to the fourth interconnection (793).

The actuator (754) and first valve (741) may be coupled to a controller, such as controller (420) described herein. The controller may be configured to control actuator (754) and first valve (741), to thereby control a resistance of fluid flow through the hydraulic assembly (700), and thus the resistance to rotation of the prosthesis. Accordingly, compression and extension of the hydraulic assembly (700) may be modified during the gait cycle of a prosthetic knee, and thus control of the compression and extension of a prosthetic joint during gait.

Figure 7B:
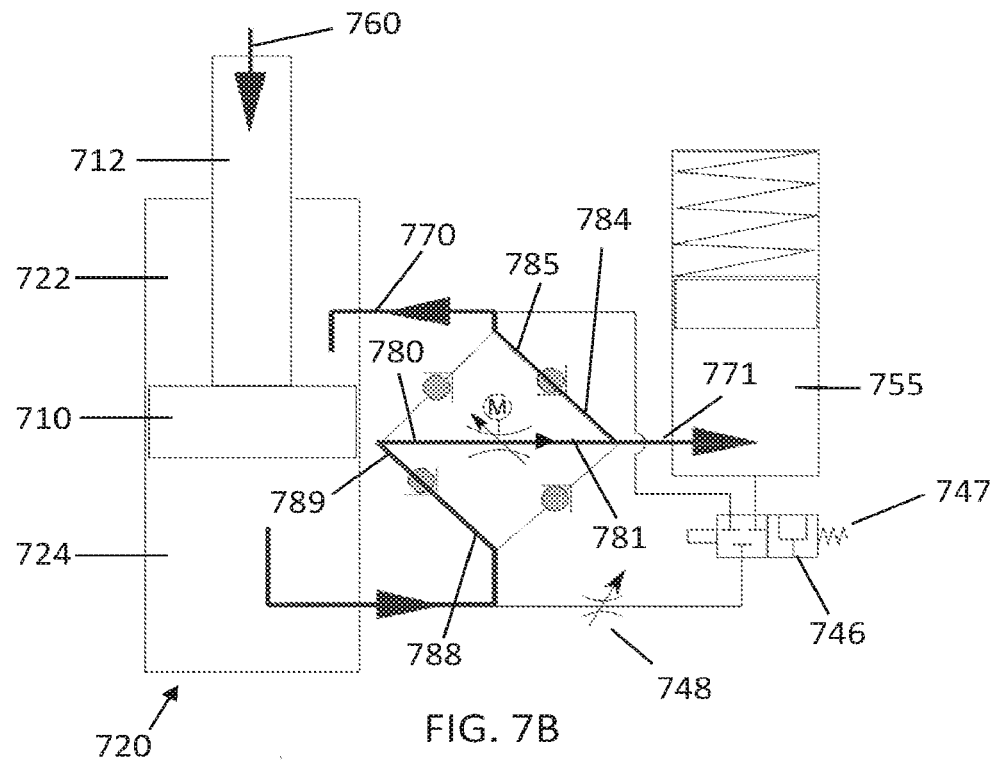

FIG. 7B illustrates hydraulic fluid flow through the hydraulic assembly (700) in response to compression (760) of the piston (710) such as in response to a power ON flexion state of a prosthetic knee. For example, as the piston (710) reduces a volume of the second chamber (724) of the cylinder (720), hydraulic fluid may enter the fluid circuit (730) through the second cylinder port (728) and exit out of the first cylinder port (726). As illustrated in FIG. 7B, the fluid circuit (730) may be configured to permit hydraulic fluid flow along a first path (770) sequentially through the second cylinder port (728), the fifth channel valve (745), the first valve (741) (e.g., variable-resistance valve), the third channel valve (743), and into the first cylinder port (726). In some variations, the flexion state may be configured to permit fluid flow along a second path (771) sequentially through the second cylinder port (728), the fifth channel valve (745), the first valve (741), and into the sump port (756). In some of these variations, the flexion state may be configured to permit fluid flow simultaneously in the first and second paths (770, 771).

In some variations, the flexion state may be configured to resist fluid flow through the second channel valve (742) and the fourth channel valve (744). The second and fourth channel valves (742, 744) may be check valves configured to resist flow received from an outlet of the fifth check valve (745) and the second cylinder port (728), respectively. Conversely, the fifth check valve, first control valve, and third check valves (745, 741, 743) may be configured to permit fluid flow from the second cylinder port (728), a channel outlet (789) of the fifth check valve (745), and a channel outlet (781) of the first valve (741), respectively. Thus, hydraulic fluid flow may be configured to permit flow from the second chamber (724) through the hydraulic circuit (730) and fluid sump (755) and into the first chamber (722).

Figure 7C:
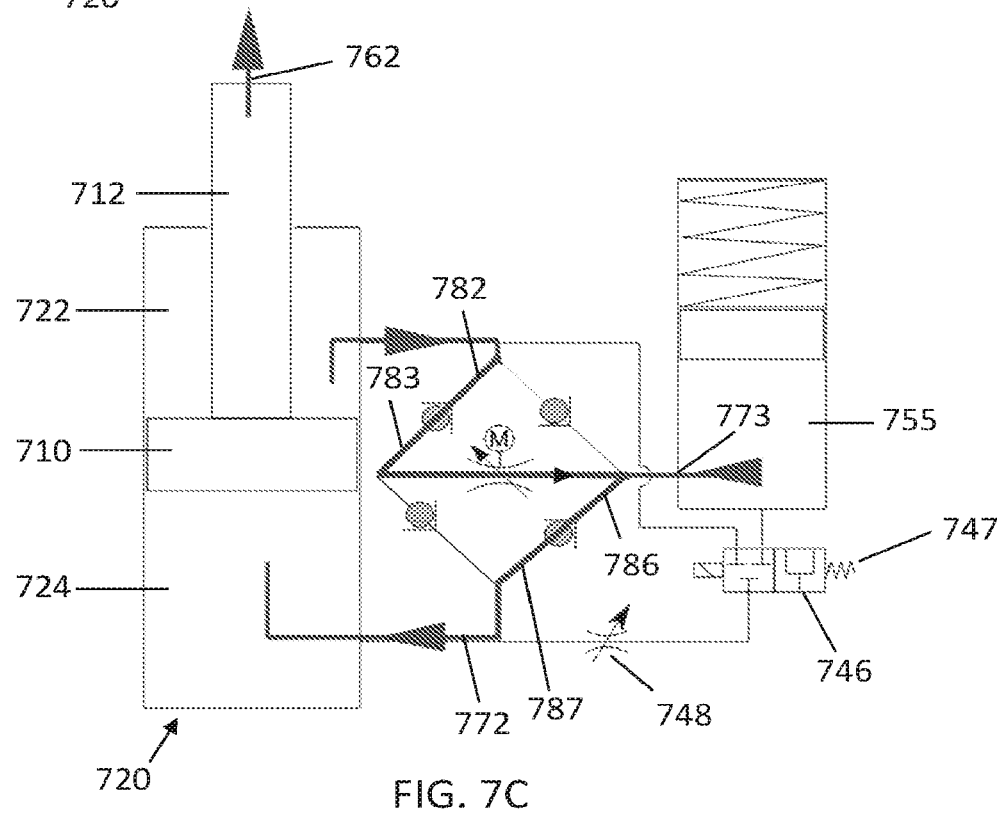

FIG. 7C illustrates hydraulic fluid flow through the hydraulic assembly (700) in response to extension of the piston (710) such as due to power ON extension of a prosthetic knee. For example, as the piston (710) reduces a volume of the first chamber (726) of the cylinder (720), hydraulic fluid may enter the fluid circuit (730) through the first cylinder port (726) and exit out of the second cylinder port (728). As illustrated in FIG. 7C, the fluid circuit (730) may be configured to permit hydraulic fluid flow along a third fluid path (772) sequentially through the first cylinder port (726), the second channel valve (742), the first valve (741) (e.g., variable-resistance valve), the fourth channel valve (744), and into the second cylinder port (728). In some variations, the extension state may be configured to permit fluid flow along a fourth fluid path (773) sequentially from the sump port (756) to the fourth channel valve (744). In some of these variations, the extension state may be configured to permit fluid flow simultaneously in the third and fourth paths (772, 773).

In some variations, the extension state may be configured to resist fluid flow through the third channel valve (743) and the fifth channel valve (745). For example, the third and fifth channel valves (743, 745) may be check valves configured to resist flow received from the first cylinder port (726) and a channel outlet (783) of the second check valve (742), respectively. Conversely, the second check valve, first control valve, and fourth check valves (742, 740, 744) may be configured to permit fluid flow from the first cylinder port (726), a channel outlet (783) of the second check valve (742), and a channel outlet (781) of the first valve (741), respectively. Thus, hydraulic fluid flow may be configured to permit flow from the first chamber (722) through the hydraulic circuit (730) and fluid sump (755) and into the second chamber (724).

Figure 7D:
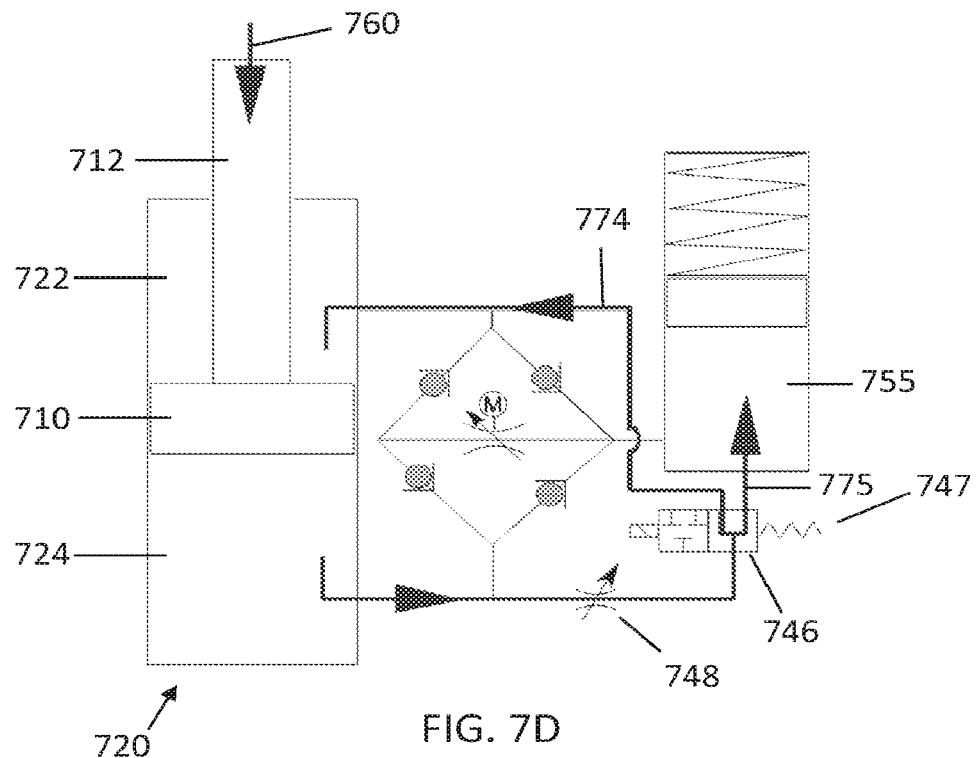

FIG. 7D illustrates hydraulic fluid flow through the hydraulic assembly (700) in response to a power OFF flexion state of a prosthetic knee. For example, as the piston (710) reduces a volume of the second chamber (724) of the cylinder (720), hydraulic fluid may enter the fluid circuit (730) through the second cylinder port (728) and exit out of the first cylinder port (726). As illustrated in FIG. 7D, the fluid circuit (730) may be configured to permit hydraulic fluid flow along a fifth fluid path (774) sequentially through the second cylinder port (728), the first variable flow resistor (748), the third valve port (751), the second valve port (750), and into the first cylinder port (726). The hydraulic circuit (730) may be further configured to permit fluid flow along a sixth fluid path (775) from the first valve port (749) to the fluid sump (755).

Figure 7E:
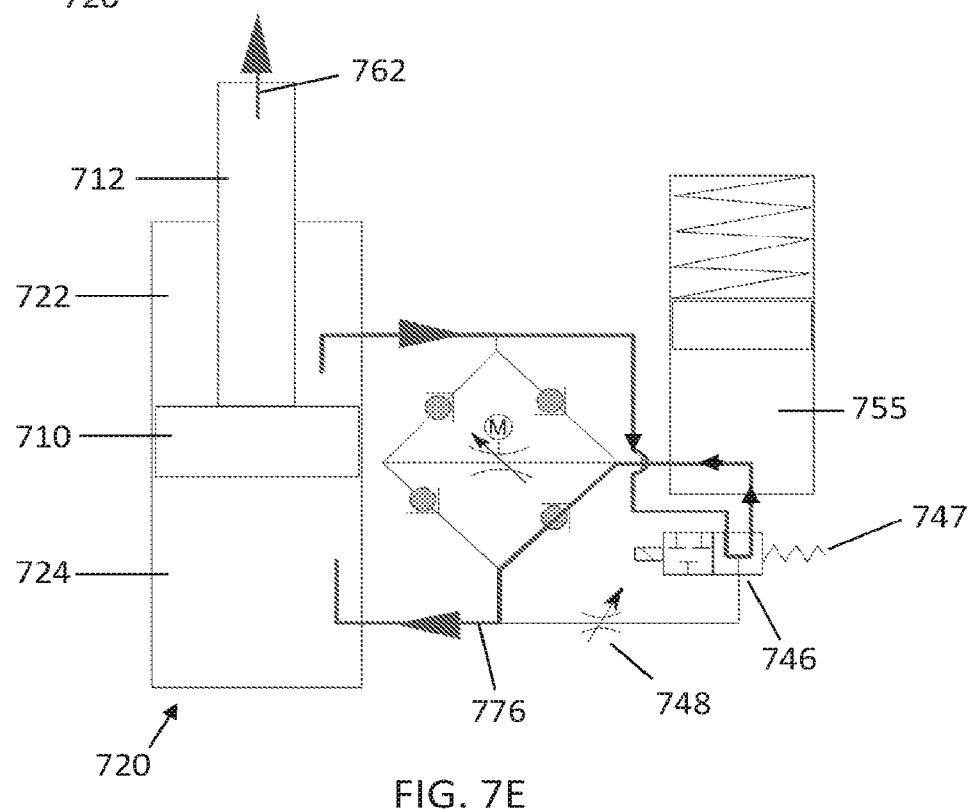

FIG. 7E illustrates hydraulic fluid flow through the hydraulic assembly (700) in response to extension of the piston (710) such as due to power OFF extension state of a prosthetic knee. For example, as the piston (710) reduces a volume of the first chamber (722) of the cylinder (720), hydraulic fluid may enter the fluid circuit (730) through the first cylinder port (726) and exit out of the second cylinder port (728). As illustrated in FIG. 7E, the fluid circuit (730) may be configured to permit hydraulic fluid flow along a seventh fluid path (776) sequentially through the first cylinder port (526), the second valve port (750), the first valve port (749), the second sump port (757), the first sump port (756), the fourth fluid channel (734), and into the second cylinder port (528).

Figure 8A:
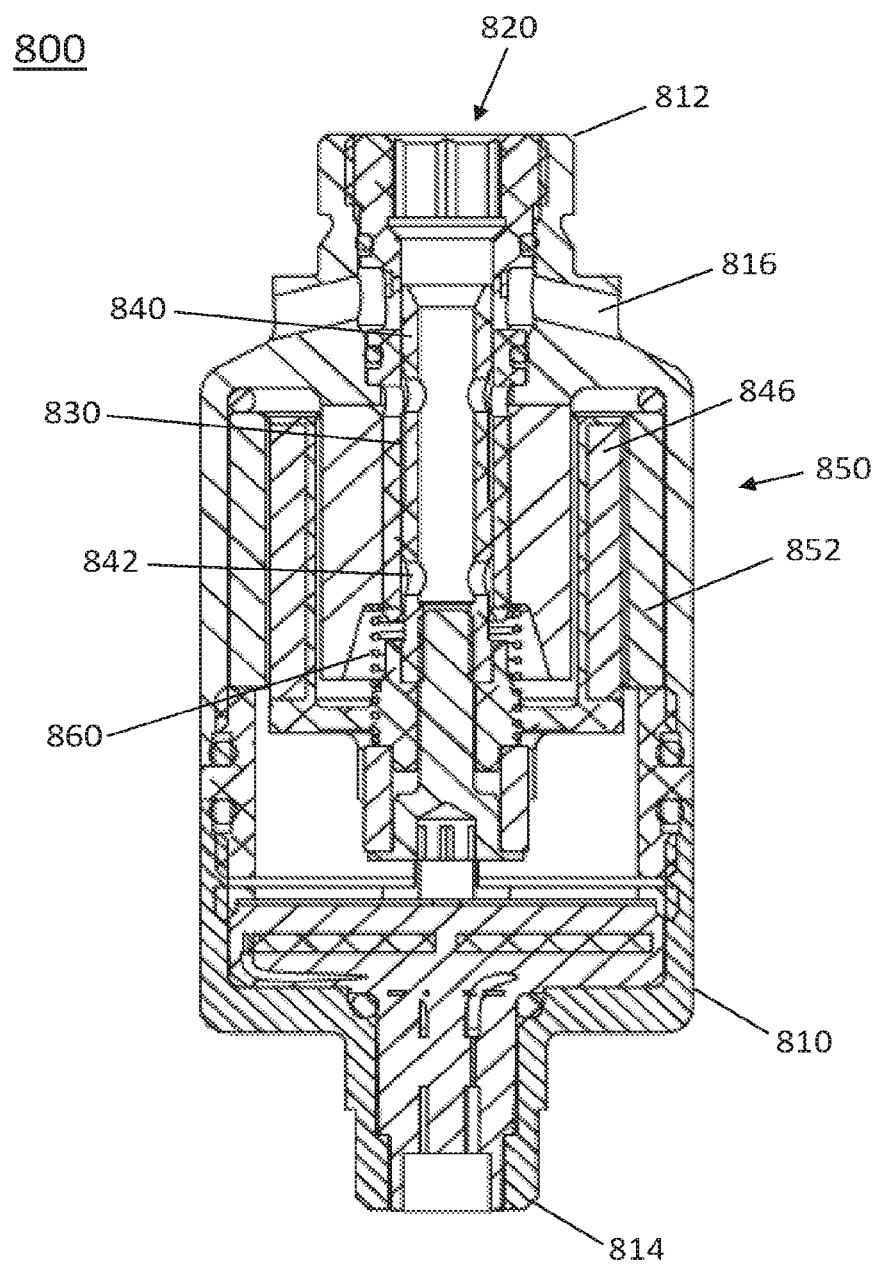
FIGS. 8A-8E are cross-sectional side views of an exemplary variation of a control valve.
Figure 8B:
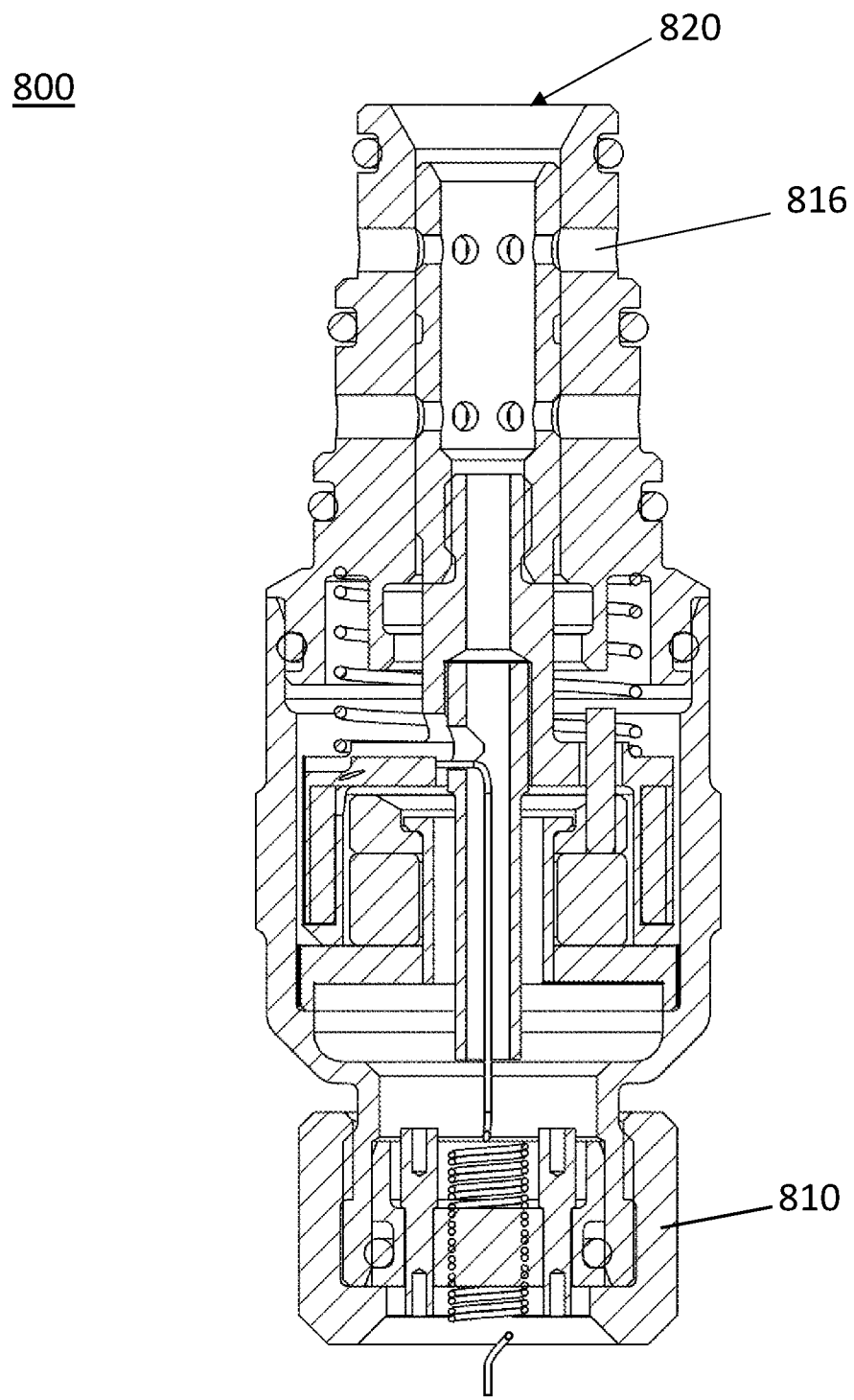
Figure 8C:
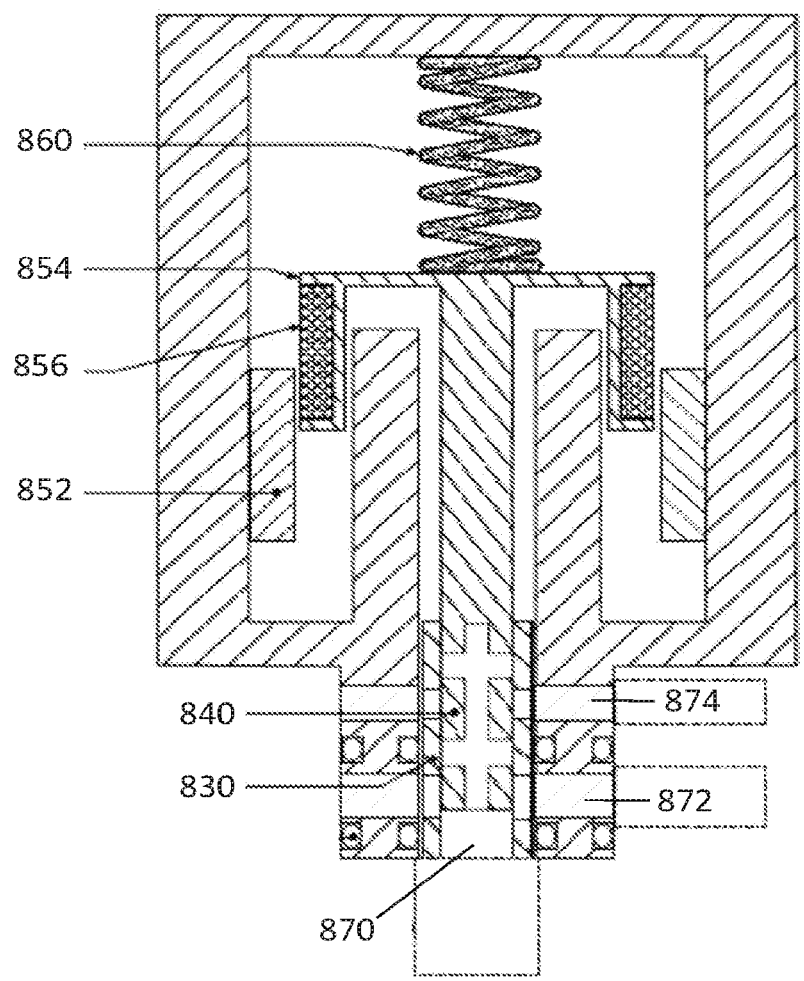
Figure 8D:
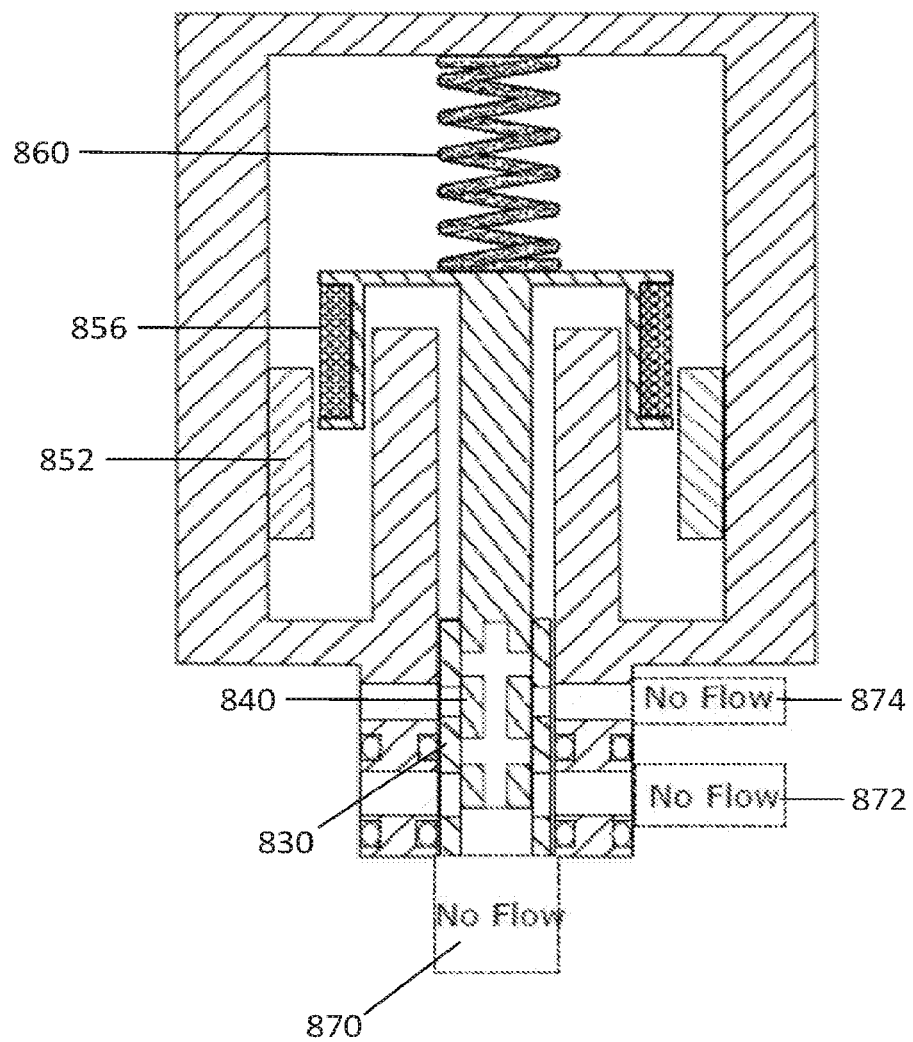
Figure 8E:
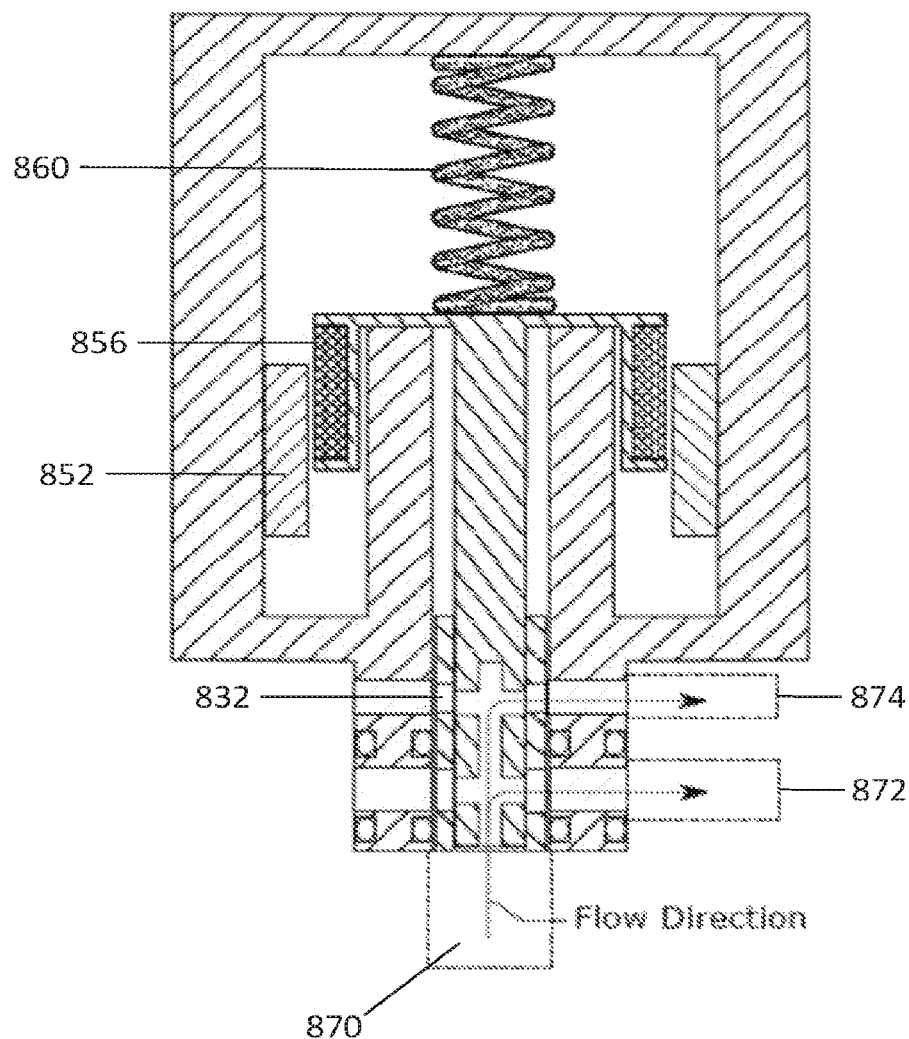

FIGS. 8A-8D are cross-sectional side views of an exemplary variation of a control valve. FIG. 8A illustrates a cross-sectional side view of a normally open proportional spool valve (800), FIG. 8B illustrates a cross-sectional side view of a power OFF valve (802), and FIG. 8C illustrates a schematic diagram of the valve (800). A control valve (800) may comprise a housing (810) having a first end (812), a second end (814), and one or more lateral openings (816). The control valve (800) may comprise a hydraulic valve (820) comprising a sleeve (830), a spool (840) defining one or more apertures (842), and a bias spring (860). The control valve (800) may further comprise an actuator (850) configured to drive the hydraulic valve (820). The actuator (850) may comprise a magnet (852), a coil bobbin (854), and a coil (846). In some variations, the magnet (852) may comprise an inner diameter of between about 2 mm and about 60, an outer diameter of between about 2.5 mm and about 70 mm, and a length of between about 1.5 mm and about 50 mm. For example, the magnet may comprise an inner diameter of between about 15 mm and about 25 mm, an outer diameter of between about 20 mm and about 30 mm, and a length of between about 15 mm and about 20 mm. In some variations, the magnet (852) may comprise neodymium although any suitable magnetic composition may be used. FIG. 8C further illustrates a first valve port (870), a second valve port (872), and a third valve port (874). FIG. 8D illustrates a schematic diagram of the valve for power OFF flexion. The spool (840) may be positioned with respect to the sleeve (830) such that fluid flow is blocked for each of the first, second, and third valve ports (870, 872, 874). FIG. 8E illustrates a schematic diagram of the valve for power OFF extension. The spool (840) may be aligned with an orifice (832) of the sleeve (830) such that fluid may flow from a first valve port (870) into the second and third valve ports (872, 874). The first, second, and third valve ports (870, 872, 874) may each comprise an area of between about 0.5 mm$^2$ and about 30 mm$^2$, and be separated from an adjacent port by between about 0.25 mm and about 30 mm. In some variations, the number of lateral openings (816) may be between about 1 and about 15. For example, the control valve (800) may comprise about 4 lateral openings (816). In some variations, the lateral opening (816) may have a diameter of between about 1 mm and about 6 mm. For example, the diameter of the lateral opening (816) may be between about 2 mm and about 4 mm.

2. Three-Port Valve

The three-port design adds an additional port to the main proportional spool valve. When the power is on, the spool may act to continually vary the orifice area depending on the desired resistance. Accordingly, a resistance to fluid flow may be controlled using the spool valve and may be varied between a fully locked position and a fully open position by varying the orifice area. When the power is off, the spool may spring biased such that a third port in the valve is opened, thereby permitting flow to a different section of the hydraulic circuit. In some variations, the three-port valve may be voice-coil actuated and servo controlled with a magnetic sensor for position feedback. The three-port valves described herein may be provided for use with a hydraulic assembly, limb prosthesis, orthotic, assistive device, or robotic linkage.

In some variations, a hydraulic assembly or system may comprise a single-ended cylinder coupled to a fluid circuit having a unidirectional three-port valve. This unidirectional control valve may set resistance to hydraulic fluid flow in both flexion (e.g., cylinder compressing) and extension (e.g., cylinder extending). The control valve may be unidirectional in that the fluid circuit ensures fluid flow in a single direction into the control valve for both compression and extension. In a power OFF state, the valve may move to the power OFF position where fluid may flow through a user-adjustable variable flow resistor to control power OFF flexion resistance. For example, extension resistance in a power OFF position may correspond to an open area of the fluid flow passages in the valve, as described in more detail herein.

Figure 9A:
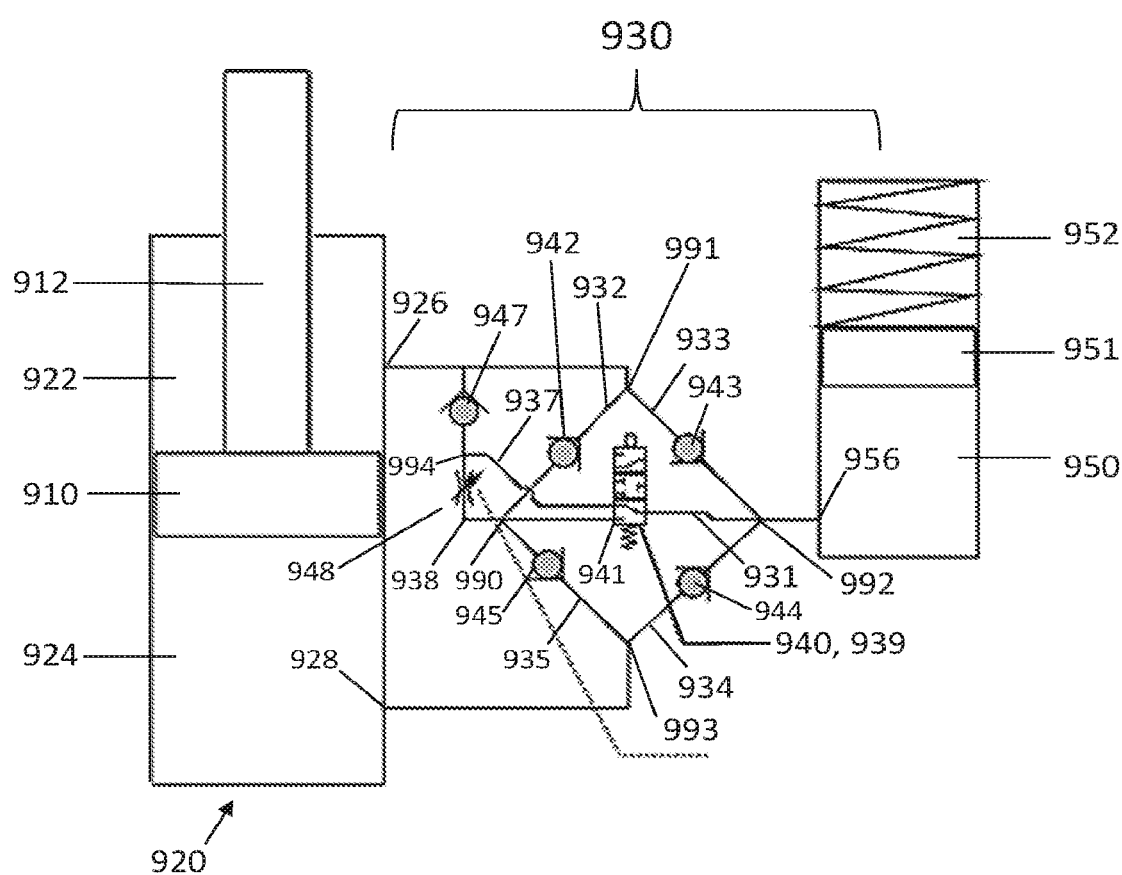
FIGS. 9A-9E are illustrative schematic diagrams of yet another variation of a hydraulic system.

FIG. 9A illustrates a hydraulic assembly (900) including a first piston (910), hydraulic cylinder (920), and a hydraulic fluid flow circuit (930). The piston (910) may be slidable within a hydraulic cylinder (920). A piston shaft (912) coupled to the piston (910) may compress or extend the piston (910) into the cylinder (920). The piston (910) may structurally separate the cylinder (920) into a first chamber (922) and an opposing second chamber (924). The first chamber (922) may include a first cylinder port (926) and the second chamber (924) may include a second cylinder port (928). In some variations, the first and second cylinder ports (926, 928) may be located on a sidewall of the cylinder (920) on opposite sides of the piston (910). In some variations, the first cylinder port (926) may be located at a first end of the cylinder (920) while the second cylinder port (928) may be located at a second end of the cylinder (920) opposite the first end.

The fluid circuit (930) may be coupled to the hydraulic cylinder (920) through the first and second cylinder ports (926, 928) such that the fluid circuit (930) may be configured to control a resistance of hydraulic fluid through the hydraulic assembly (900). The fluid circuit (930) may include a plurality of hydraulic fluid channels configured to control hydraulic fluid flow between the first chamber (922), the second chamber (924), and a fluid sump (950). A first hydraulic fluid channel (931) may comprise a first channel inlet (980) (labeled in FIG. 9B), a first channel outlet (981), and a first channel valve (940) configured to set a variable resistance to flow through the first fluid channel (931). In some variations, the first channel valve (940) may comprise a three-way spool valve and a secondary channel inlet (941). In some variations, the first channel valve (940) may comprise a spring and may be configured to normally permit fluid communication between the secondary channel inlet (941) and the first channel outlet (981) when the first channel valve (940) is an unpowered three-way spool valve. A second fluid channel (932) may comprise a second channel inlet (982) (labeled in FIG. 9C), a second channel outlet (983), and a second channel valve (942). A third fluid channel (933) may comprise a third channel inlet (984) (labeled in FIG. 9B), a third channel outlet (985), and a third channel valve A fourth fluid channel (934) may comprise a fourth channel inlet (986) (labeled in FIG. 9E), a fourth channel outlet (987), and a fourth channel valve (944). A fifth fluid channel (935) may comprise a fifth channel inlet (988) (labeled in FIG. 9B), a fifth channel outlet (989), and a fifth channel valve (945). A seventh fluid channel (937) may comprise a seventh channel inlet (961) (labeled in FIG. 9E), a seventh channel outlet (962), and a seventh channel valve (947). The seventh channel inlet (961) may be connected to the first cylinder port (926) or a second interconnection (991) (e.g., intersection). In some variations, the seventh channel valve (947) may comprise a check valve. An eighth fluid channel (938) may comprise an eighth channel inlet (963) (labeled in FIG. 9E), and eighth channel outlet (964), and a second variable flow resistor (948).

In some variations, a first interconnection (990) (e.g., intersection) may comprise the first channel inlet (980), second channel outlet (983), and the fifth channel outlet (989). In some variations, the first interconnection (990) may further comprise the eighth channel inlet (963) (labeled in FIG. 9E). A second interconnection (991) may comprise the first cylinder port (926), the second channel inlet (982), and the third channel outlet (985). A third interconnection (992) may comprise the sump port (956), the third channel inlet (984), and the fourth channel inlet (986). A fourth interconnection (993) may comprise the second cylinder port (928), the fourth channel outlet (987), and the fifth channel inlet (988). A fifth interconnection (994) may comprise the seventh fluid channel outlet (962), the eighth channel inlet (963), the eighth channel outlet (964), and the secondary channel inlet (941) of the first valve (940).

In some variations, the first channel inlet (980) may be connected between the second channel valve (942) and the fifth channel valve (945). The first cylinder port (926) may be connected between the second channel valve (942) and the third channel valve (943). A. sump port (956) may be connected between the third channel valve (943) and the fourth channel valve The second cylinder port (928) may be connected between the fourth channel valve (944) and the fifth channel valve (945). The second channel valve (942) and fifth channel valve (945) may be connected in series. The third channel valve (943) and fourth channel valve (943) may be connected in series. The second channel valve (942) and the third channel valve (943) may be connected in parallel. The fourth channel valve (944) and the fifth channel valve (945) may be connected in parallel. A first channel inlet (980) of the first hydraulic fluid channel (931) may be connected between the second and fifth fluid channels (932, 935). A first channel outlet (981) of the first hydraulic fluid channel (931) may be connected between the third and fourth fluid channels (933, 934).

The first valve (940) may be configured to set a resistance to flow of hydraulic fluid through the first hydraulic fluid channel (931). The fluid circuit (930) may be configured such that hydraulic fluid flows into the first hydraulic fluid channel (931) in the same direction for both extension and compression of the piston (910). Therefore, the first valve (940) may comprise a unidirectional control valve rather than a bi-directional valve. The first valve (940) may be a control valve such as a proportional directional control valve. In some variations, the first valve (940) may comprise one or more of a voice coil valve, solenoid valve, and DC motor. The first valve (940) may have a rotary or linear geometry. In some variations, the second through fifth valves (942, 943, 944, 945) may be check valves configured to permit hydraulic fluid flow in a single direction.

In some variations, an actuator (939) may be coupled to the first valve (940). The actuator (939) may be configured to bi-directionally drive the first valve (940) to reciprocally and selectively position the first valve (940) based on the polarity of the current applied to the actuator (939). Thus, the first valve (940) may be bi-directionally driven by the actuator (939).

The first valve (940) may include a sleeve having an orifice and a spool movable with respect to the sleeve. The actuator (939) may be coupled to the first valve (940) to move the spool with respect to orifice to vary a resistance to fluid flow through the first valve (940). In some variations, the actuator (939) may move a spool with respect to the orifice. Thus, the first valve (940) may be configured to set the resistance of fluid through the fluid circuit (930). As described in more detail herein, the check valves may be configured such that fluid flows through different fluid channels under compression and extension of the piston (910).

The fluid circuit (930) may be connected to a fluid sump (950). In some variations, the fluid sump (950) may comprise a spring-biased second piston (951) and a spring (952). The fluid sump (950) may comprise a cavity that serves as a reservoir for hydraulic fluid displaced by movement of the piston (910) in the cylinder (920). The spring (952) may be configured to generate a spring force that acts on the second piston (951) as the volume of the cavity increases with increased fluid volume, thereby creating an internal pressure that acts equally on both sides of the second piston (951). Since the pressure area is not equal on both sides of the second piston (951), the net force acting on the second piston (951) is non-zero and may tend to push the piston shaft (912) out of the cylinder (920) resulting in a linear cylinder spring rate. The cylinder spring rate may correspond to swing extension assistance that may assist extension of the knee.

The actuator (939) and first valve (940) may be coupled to a controller, such as controller (420) described herein. The controller may be configured to control actuator (939) and first valve (940), to thereby control a resistance of fluid flow through the hydraulic assembly (900), and thus the resistance to rotation of the prosthesis. Accordingly, compression and extension of the hydraulic assembly (900) may be modified during the gait cycle of a prosthetic knee, and thus control of the compression and extension of a prosthetic joint during gait.

Figure 9B:
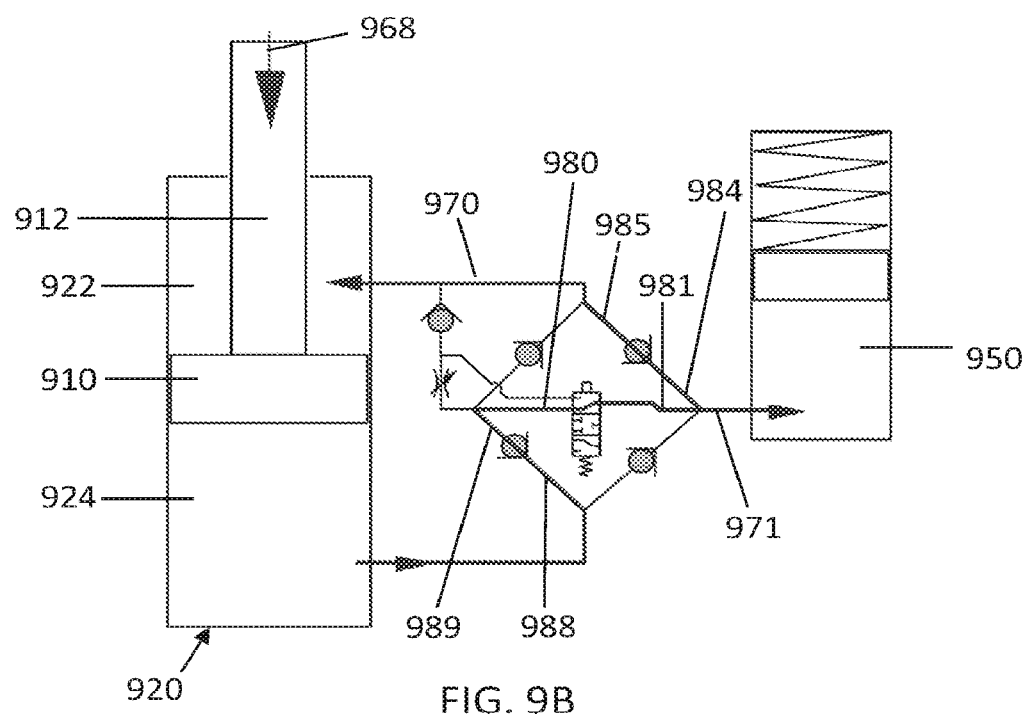

FIG. 9B illustrates hydraulic fluid flow through the hydraulic assembly (900) in response to compression (968) of the piston (910) such as in response to a power ON flexion state of a prosthetic knee. For example, as the piston (910) reduces a volume of the second chamber (924) of the cylinder (920), hydraulic fluid may be permitted to enter the fluid circuit (930) through the second cylinder port (928) and exit out of the first cylinder port (926). As illustrated in FIG. 9B, the fluid circuit (930) may be configured to permit hydraulic fluid flow along a first fluid path (970) sequentially through the second cylinder port (928), the fifth channel valve (945), the eight fluid channel (980), the first valve (940) (e.g., variable-resistance three-port valve), the third channel valve (943), and into the first cylinder port (926). In some variations, the flexion state may be configured to permit fluid flow along a second fluid path (971) from the first valve (940) into the sump port (956). In some of these variations, the flexion state may be configured to permit fluid flow simultaneously in the first and second fluid paths (970, 971).

In some variations, the flexion state may be configured to resist fluid flow through the second channel valve (942) and the fourth channel valve (944). The second and fourth channel valves (942, 944) may be check valves configured to resist flow received from an outlet of the fifth check valve (945) and the second cylinder port (928), respectively. Conversely, the fifth check valve, first control valve, and third check valves (945, 940, 943) may be configured to allow fluid flow from the second cylinder port (928), an outlet of the fifth check valve (948), eighth channel inlet (963), and a secondary channel inlet (941), respectively. Thus, hydraulic fluid flow may be configured to flow from the second chamber (924) through the hydraulic circuit (930) and fluid sump (950) and into the first chamber (922).

Figure 9C:
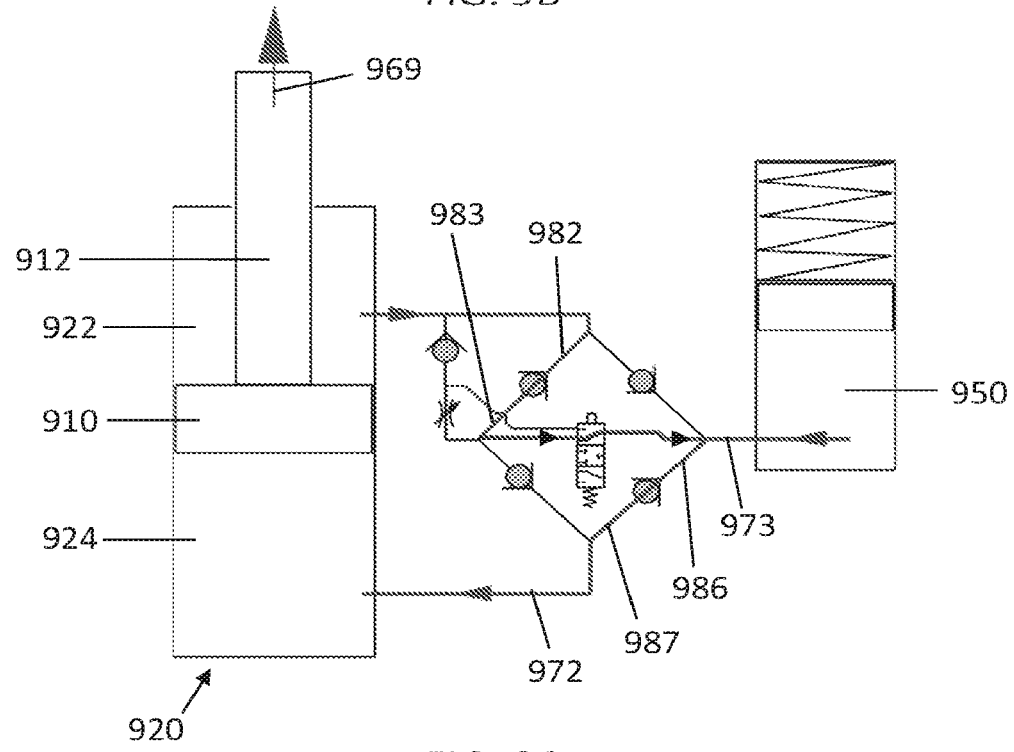

FIG. 9C illustrates hydraulic fluid flow through the hydraulic assembly (900) in response to extension (969) of the piston (910) such as due to power ON extension of a prosthetic knee. For example, as the piston (910) reduces a volume of the first chamber (926) of the cylinder (920), hydraulic fluid may enter the fluid circuit (930) through the first cylinder port (922) and exit out of the second cylinder port (928). As illustrated in FIG. 9C, the fluid circuit (930) may be configured to permit hydraulic fluid flow along a third fluid path (972) sequentially through the first cylinder port (926), the second channel valve (942), the seventh fluid channel (937), the secondary channel inlet (941), the first valve (940) (e.g., three-way valve), the fourth channel valve (944), and into the second cylinder port (928). In some variations, the extension state may be configured to permit fluid flow along a fourth fluid path (973) sequentially from the sump port (956) to the fourth channel valve (944). In some of these variations, the extension state may be configured to permit fluid flow simultaneously in the third and fourth fluid paths (972, 973).

In some variations, the extension state may be configured to resist fluid flow through the third channel valve (943) and the fifth channel valve (945). The third and fifth channel valves (943, 945) may be check valves configured to resist flow received from the first cylinder port (926) and a channel outlet (983) of the second check valve (942), respectively.

Conversely, the second check valve, first control valve, and fourth check valves (942, 940, 944) may be configured to allow fluid flow from the first cylinder port (926), a channel outlet (983) of the second check valve (942), and a channel outlet (981) of the first valve (940), respectively. Thus, hydraulic fluid flow may be configured to flow from the first chamber (922) through the hydraulic circuit (930) and fluid sump (950) and into the second chamber (924).

Figure 9D:
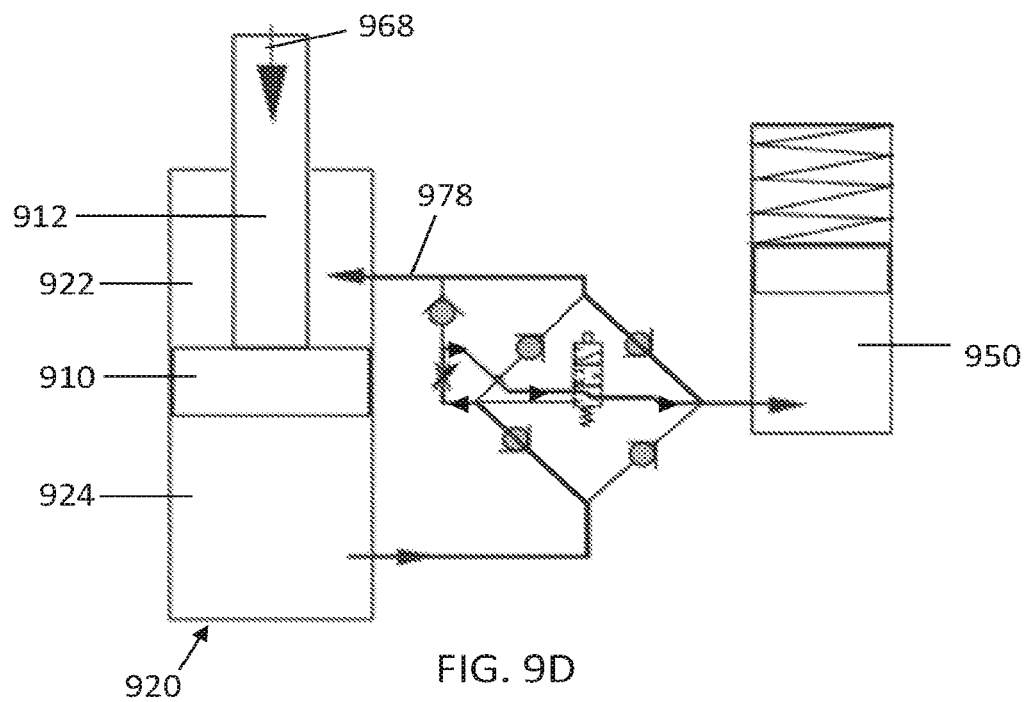

FIG. 9D illustrates hydraulic fluid flow through the hydraulic assembly (900) in response to compression (968) of the piston (910) such as in response to a power OFF flexion state of a prosthetic knee. For example, as the piston (910) reduces a volume of the second chamber (924) of the cylinder (920), hydraulic fluid may be permitted to enter the fluid circuit (930) through the second cylinder port (928) and exit out of the first cylinder port (926). As illustrated in FIG. 9D, the fluid circuit (930) may be configured to permit hydraulic fluid flow along an eighth fluid path (978) sequentially through the second cylinder port (928), the fifth fluid channel (935), the eighth fluid channel (938), the secondary channel inlet (941) of the first valve (940), the third fluid channel (933), and into the first cylinder port (926). In some variations, the flexion state may be configured to permit fluid flow along a second fluid path (971) from the first valve (940) into the sump port (956). In some of these variations, the flexion state may be configured to permit fluid flow simultaneously in the first and second fluid paths (970, 971). In some of these variations, fluid may flow from the first channel outlet (981) to the fluid sump (950).

Figure 9E:
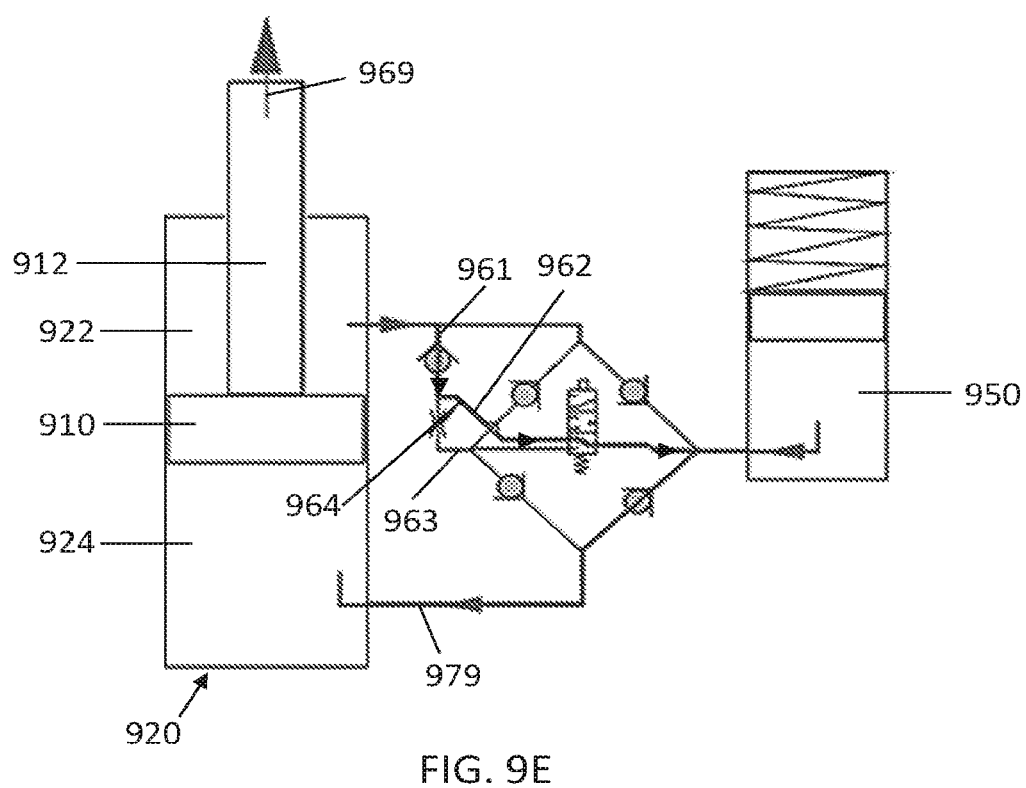

FIG. 9E illustrates hydraulic fluid flow through the hydraulic assembly (900) in response to extension of the piston (910) such as due to power OFF extension state of a prosthetic knee. For example, as the piston (910) reduces a volume of the first chamber (922) of the cylinder (920), hydraulic fluid may enter the fluid circuit (930) through the first cylinder port (926) and exit out of the second cylinder port (928). As illustrated in FIG. 9E, the fluid circuit (930) may be configured to permit hydraulic fluid flow along a ninth fluid path (979) sequentially through the first cylinder port (926), the seventh fluid channel (937), the secondary channel inlet (941), the fourth fluid channel (934), into the second cylinder port (928). In some of these variations, fluid flow may be provided from the fluid sump (950) to the fourth fluid channel (934).

Figures 10A, 10B:
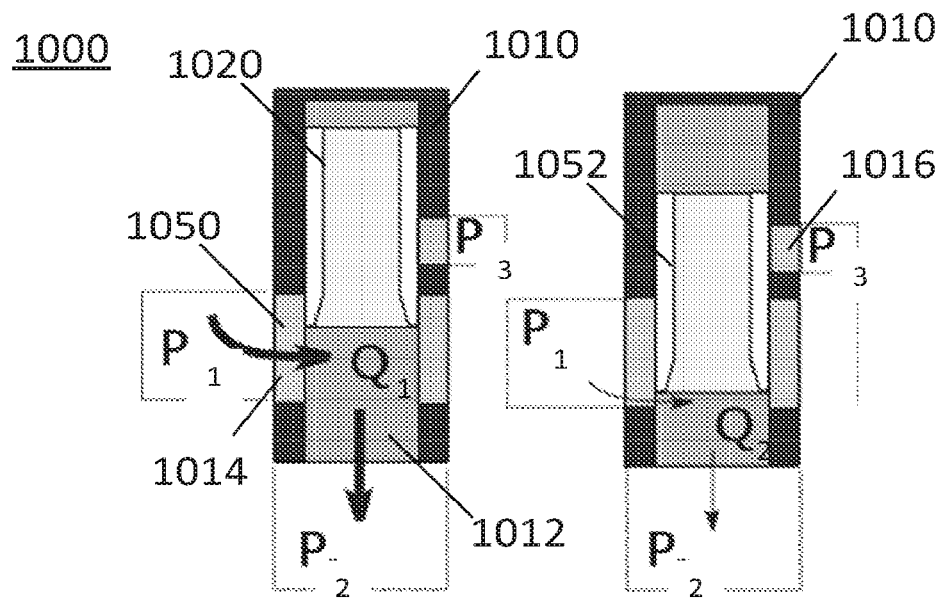
FIGS. 10A-10D are illustrative schematic views of fluid flow using another variation of a control valve.

Fluid flow through a valve (1000) will be described with respect to the cross-sectional side views depicted in FIGS. 10A-10D. In FIG. 10A, the spool (1020) is at a first spool position (1050) within the sleeve (1010). At the first spool position (1050), fluid flows at a first volumetric flow rate Qi from an area having a higher first pressure PI through a first lumen (:1012) to an area having a lower second pressure P2. The spool (1020) overlaps only a small portion of the first orifice (1014) such that there is a relatively low level of resistance to fluid flow such that an amputee may experience a low level of resistance to joint rotation range. The second orifice (1016) is completely blocked by the spool (1020).

In FIG. 10B, the spool (1020) is at a second spool position (1052) within the sleeve (1010). At the second spool position (1052), fluid flows at a second volumetric flow rate $Q_2$ from an area having a higher first pressure $P_1$ through a first lumen (1012) to an area having a lower second pressure $P_2$. The second volumetric flow rate $Q_2$ is less than the first volumetric flow rate $Q_1$. The spool (1020) overlaps a significant portion of the first orifice (1014) such that there is a relatively intermediate and/or high level of resistance to fluid flow such that an amputee may experience an intermediate and/or high level of resistance to joint rotation. The second orifice (1016) is completely blocked by the spool (1020).

Figures 10C, 10D:
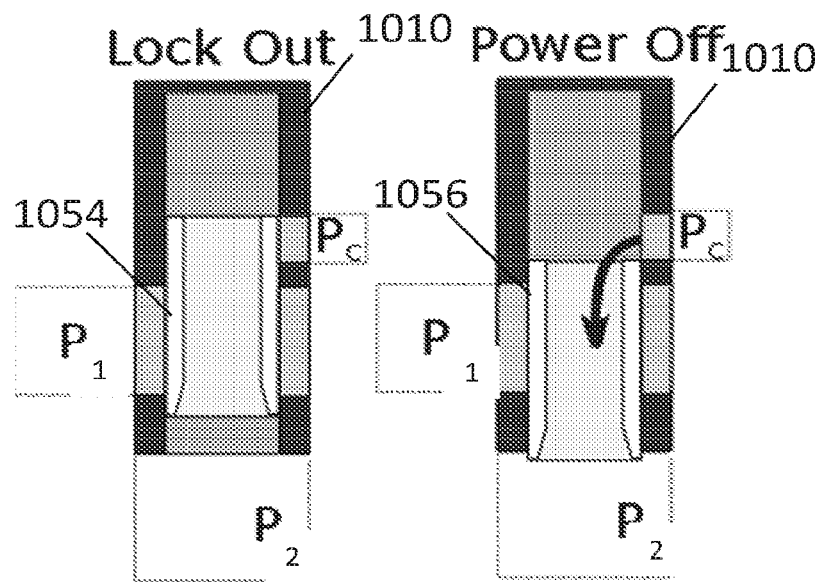

In FIG. 10C, the spool (1020) is at a third spool position (1054) within the sleeve (:1010). At the third spool position (1054), fluid does not flow through the valve (1000) (e.g., lockout). The first orifice (1014) and second orifice (1016) are completely blocked by the spool (1020). In this configuration, the valve (1000) provides maximum resistance to fluid flow such that the prosthetic joint may be fixed at a particular angle.

In FIG. 10D, the spool (1020) is at a fourth spool position (1056) within the sleeve (1010). At the fourth spool position (1056), the first orifice (1014) is completely blocked by the spool (1020). However, the second orifice (1016) becomes unblocked such that fluid may flow from an area having a higher third pressure $P_3$ through a second lumen (1022) to an area having a lower second pressure $P_2$. In some variations, the first pressure $P_1$ may be up to about 4000 psi, the second pressure $P_2$ may be up to about 4000 psi, and the third pressure $P_3$ may be up to about 4000 psi.

Figure 11A:
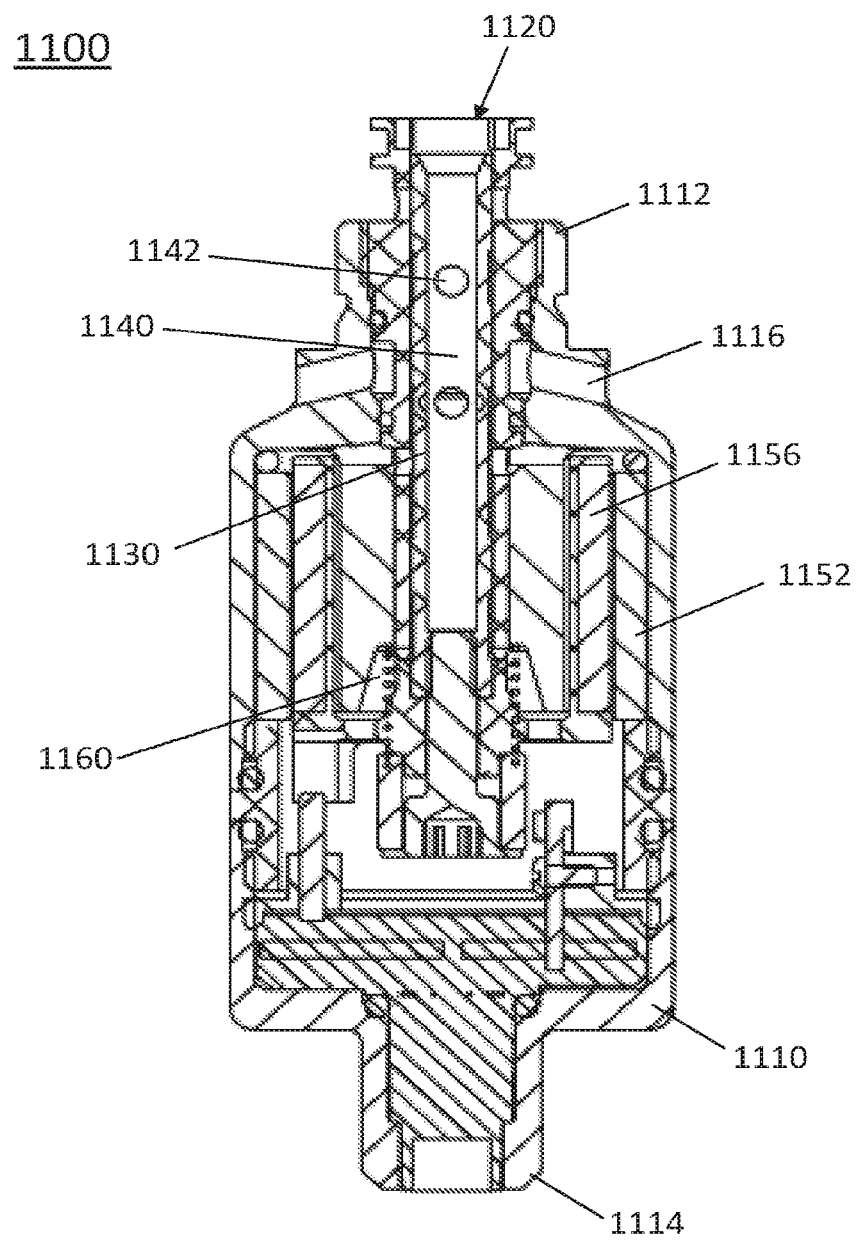
FIGS. 11A-11E are cross-sectional side views of another exemplary variation of a control valve.
Figure 11B:
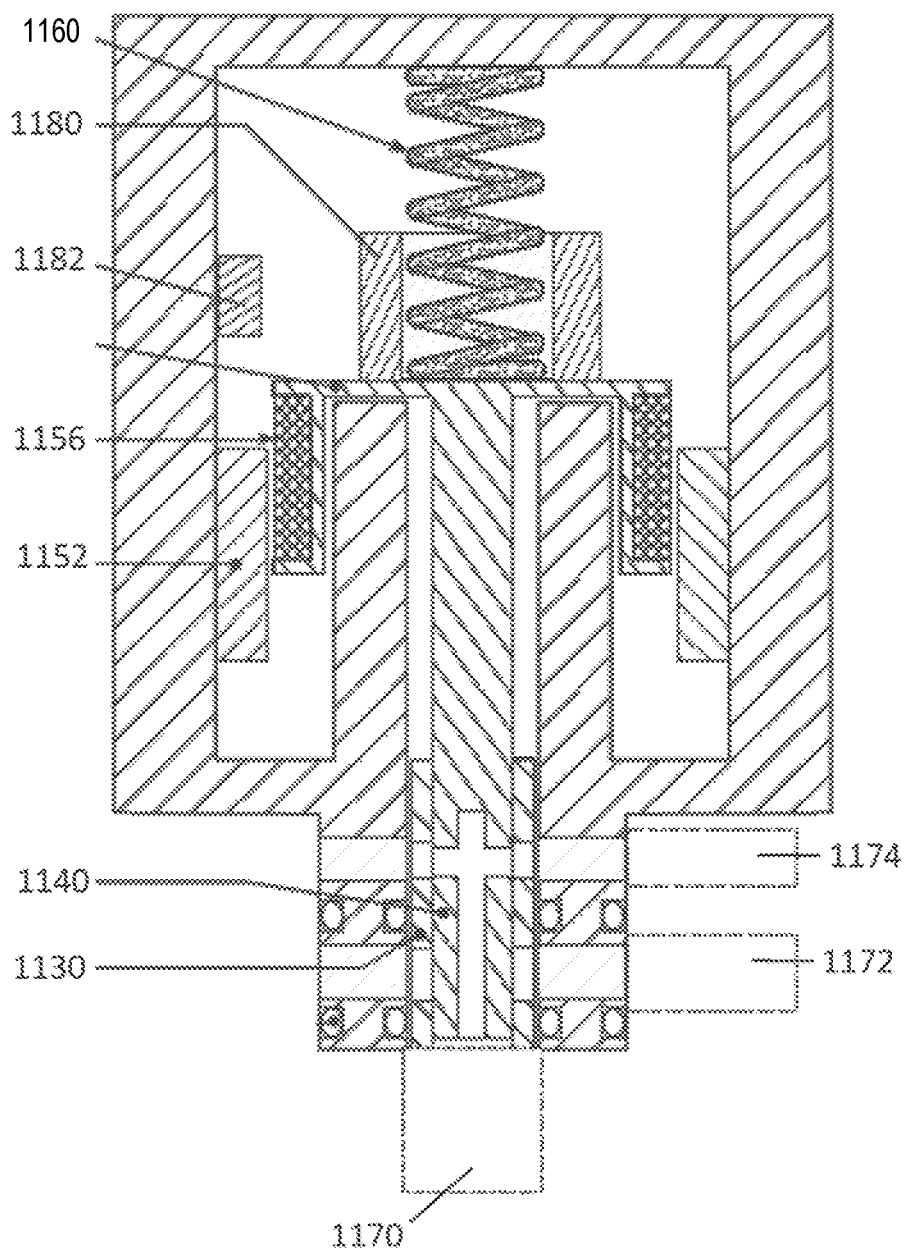
Figure 11C:
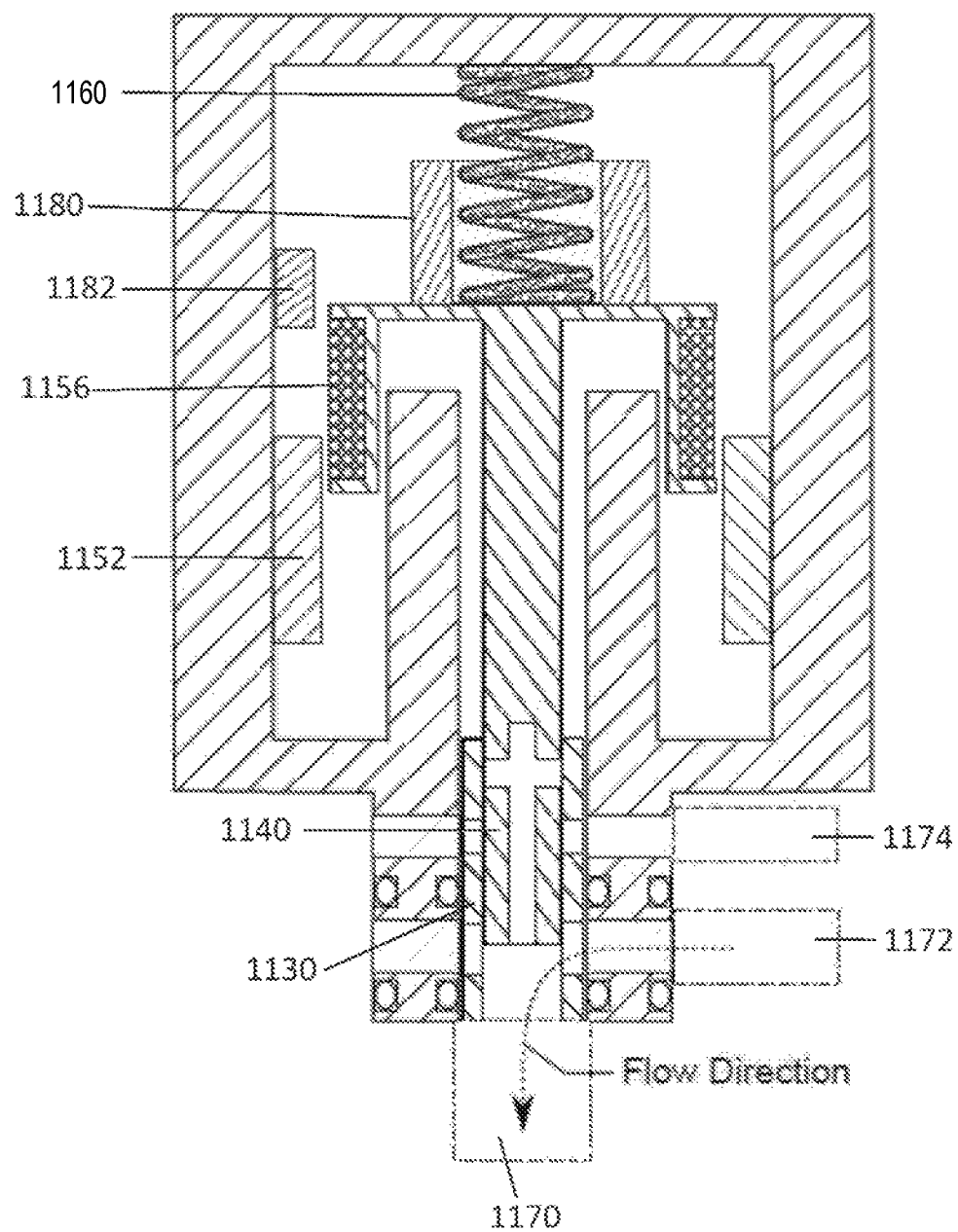
Figure 11D:
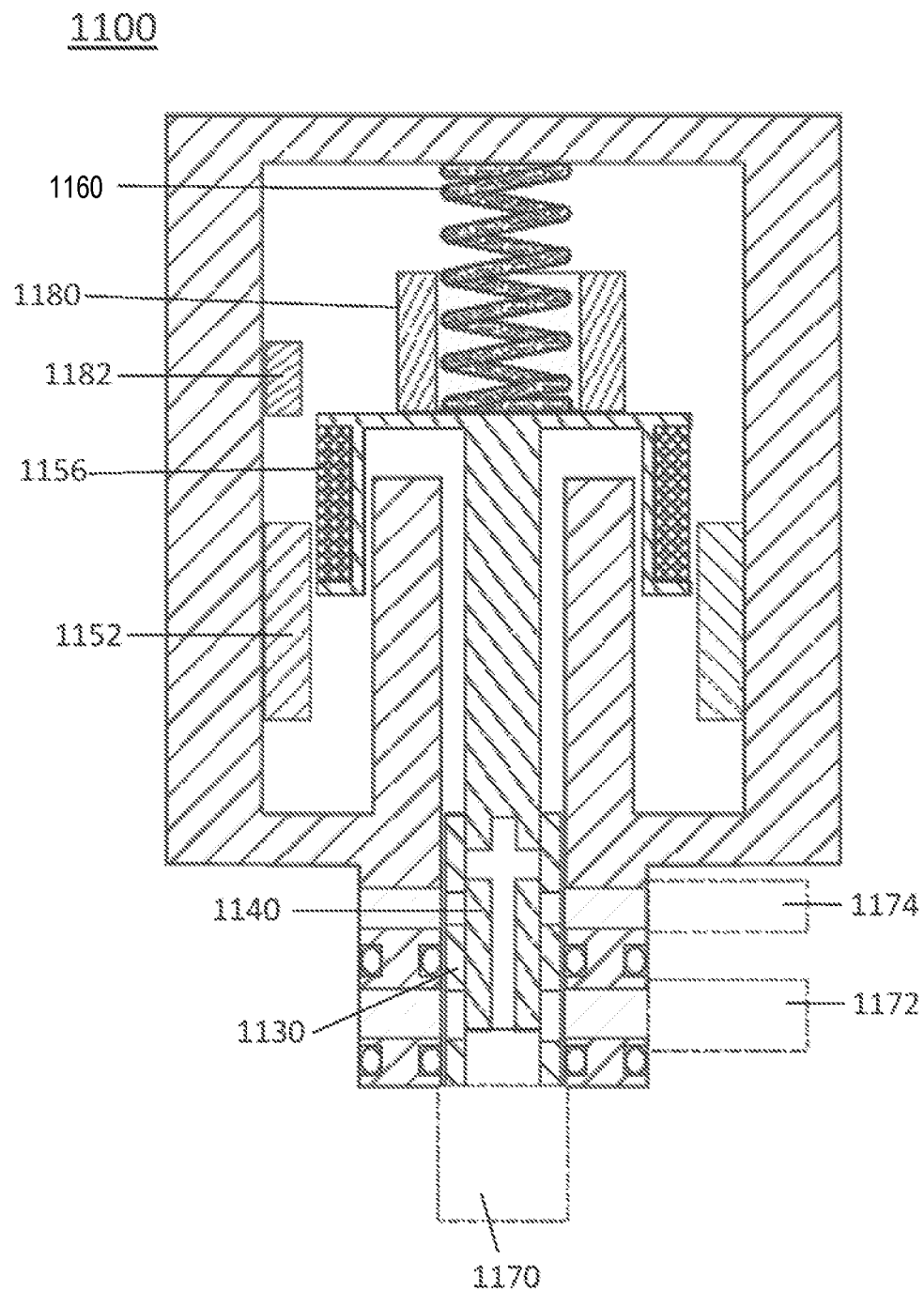
Figure 11E:
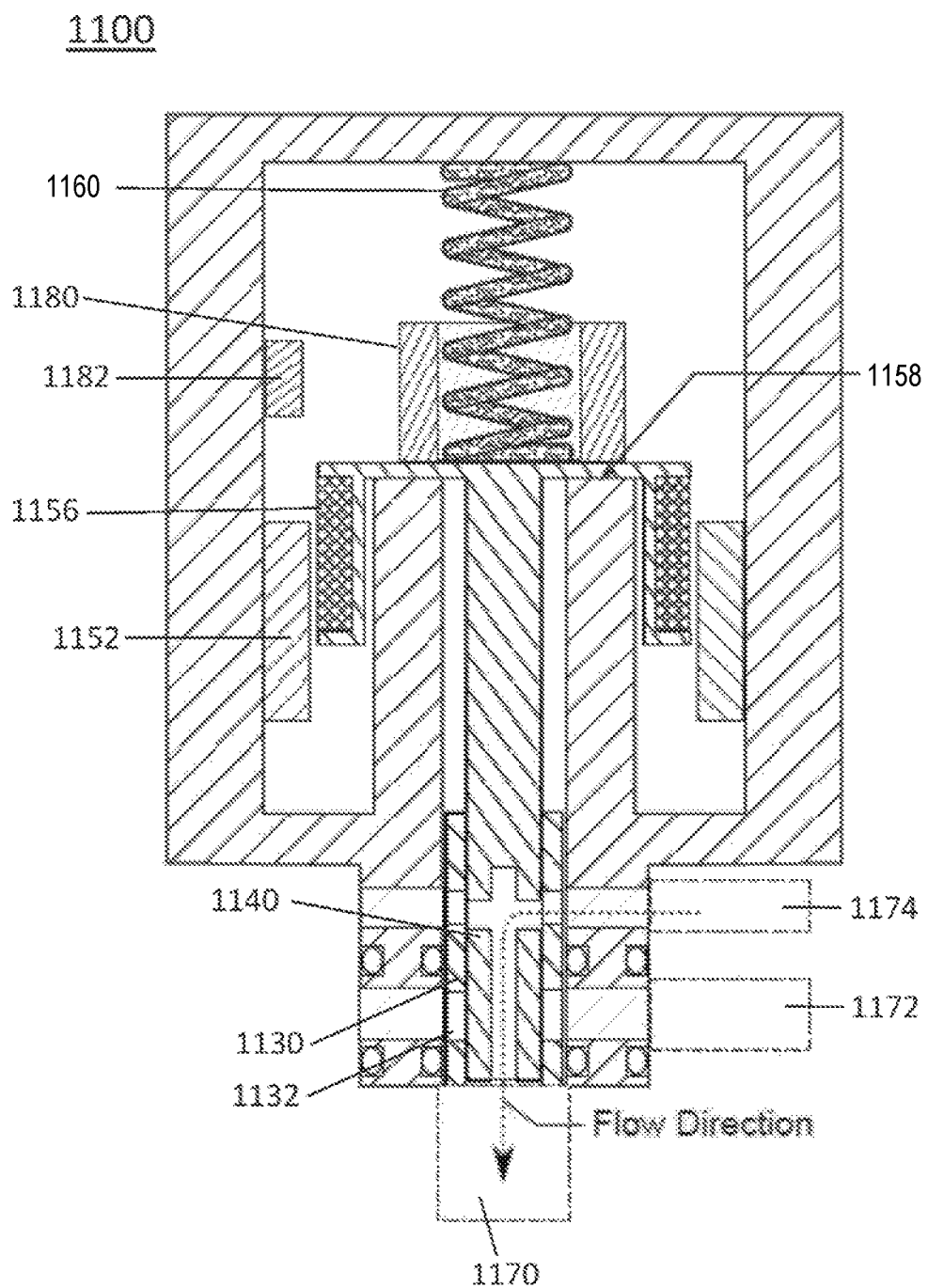

FIGS. 11A-11E are cross-sectional side views of an exemplary variation of a control valve. FIG. 11A illustrates a cross-sectional side view of a normally closed proportional three-port spool valve (1100). FIGS. 11B and 11D illustrate schematic diagrams of the valve (1100). A control valve (1100) may comprise a housing (1110) having a first end (1112), a second end (1114), and one or more lateral openings (1116). The control valve (1100) may comprise a hydraulic valve (1120) comprising a sleeve (1130) defining an orifice (1132), a spool (1140) defining one or more apertures (1142), and a bias spring (1160). The control valve (1100) may further comprise an actuator (1150) configured to drive the hydraulic valve (1120). The actuator (1150) may comprise a magnet (1152) (e.g., voice coil magnet), a coil bobbin (1154), and a coil (1146) (e.g., voice coils). FIGS. 11B and 11D further illustrate a first valve port (1170), a second valve port (1172), and a third valve port (1174). FIG. 11D illustrates a schematic diagram of the valve for power OFF flexion. The spool (1140) may be positioned with respect to the sleeve (1130) such that fluid flow is blocked for the third valve port (1174) and permitted for fluid to flow from the second valve port (1172) into the first valve port (1170). FIG. 11E illustrates a schematic diagram of the valve for power OFF extension. The spool (1140) may be aligned with the orifice (1132) of the sleeve (1130) such that fluid may flow enter a third valve port (1174) into the first valve port (1170).

Knee torque calculations may be used to control systems and devices described herein. In some variations, torque estimation may be achieved by placing a load cell in line with the hydraulic cylinder. By knowing the angle of the knee, the moment arm of the cylinder may be calculated. Combining the moment arm with the load on the cylinder allows for calculation of the torque about the knee joint. The load cell may be placed in the distal cylinder mount, the piston shaft, or the cylinder. In some variations, pressure gauges internal to the cylinder may be used to measure the differential pressure and may also be used to calculate the load on the cylinder.

Figure 13A:
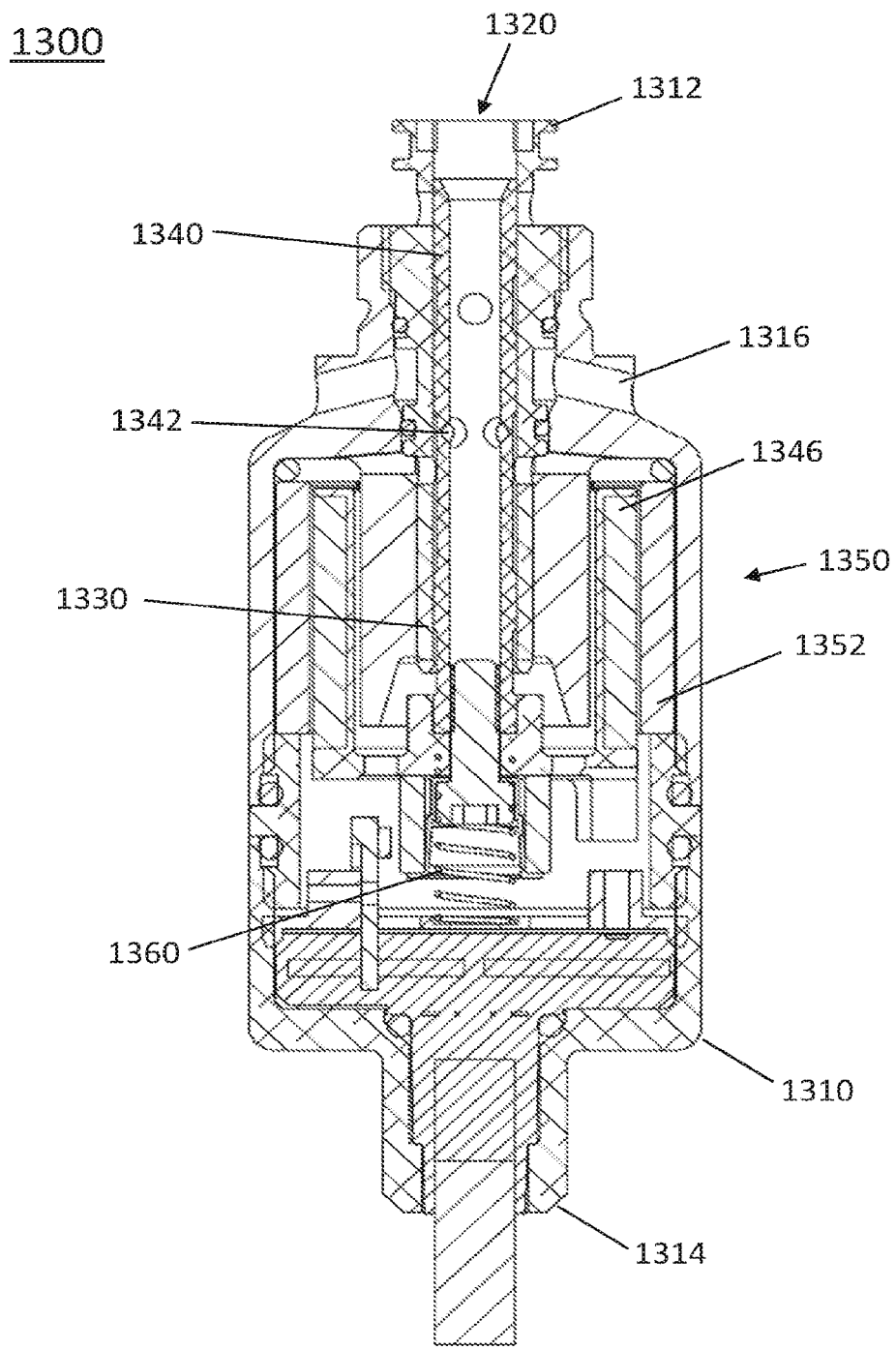
FIG. 13A is cross-sectional side view of another variation of a control valve.

FIG. 13A is a cross-sectional side view of another exemplary variation of a control valve (1300). A control valve (1300) may comprise a housing (1310) having a first end (1312), a second end (1314), and one or more lateral openings (1316). The control valve (1300) may comprise a hydraulic valve (1320) comprising a sleeve (1310), a spool (1320) defining one or more apertures (1342), and a spring (1360). The control valve (1300) may further comprise an actuator (1350) configured to drive the hydraulic valve (1320). The actuator (1350) may comprise a magnet (1352) and a coil (1346). In some variations, the magnet (1352) may comprise an inner diameter of between about 2 mm and about 60, an outer diameter of between about 2.5 mm and about 70 mm, and a length of between about 1.5 mm and about 50 mm. For example, the magnet (1352) may comprise an inner diameter of between about 15 mm and about 25 mm, an outer diameter of between about 20 mm and about 30 mm, and a length of between about 15 mm and about 20 mm. In some variations, the magnet (1352) may comprise neodymium although any suitable magnetic composition may be used.

Figures 13B, 13C, 13D, 13E:
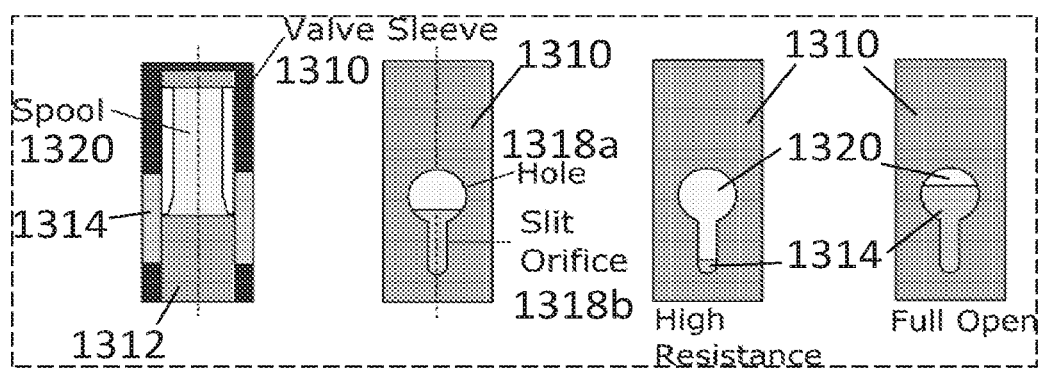
FIGS. 13B-13E are illustrative schematic views of a variation of the control valve depicted in FIG. 13A.

FIGS. 13B-13E are illustrative schematic views of a variation of a control valve. FIG. 13B is a cross-sectional side view of a sleeve and spool, and FIGS. 13C-13E are side views of the sleeve, spool, and orifice in different resistance states. FIG. 13B is a cross-sectional side view of a valve (1300) comprising a sleeve (1310) and a spool (1320). The spool (1320) may be slidable within a first lumen (1312) of the sleeve (1310) and may be driven by an actuator (not shown) such as a voice coil actuator, solenoid actuator, or other actuator (e.g., DC brushless motor). The sidewalls of the sleeve (1310) may define one or more orifices (1314). As the spool (1320) slides through the sleeve (1310), portions of the spool (1320) may overlap portions of the orifice (1314). FIG. 13C is a side view of the sleeve (1310) illustrating the orifice (1314) depicted in FIG. 13B as having a hole (1318a) and a slit (1318b). As shown in FIGS. 13C-13F, the orifice (1314) may have a keyhole-like shape. However, the shape of the orifice (1314) is not particularly limited. FIG. 13D illustrates the valve (1300) in a high resistance state where the hole (1318a) and a large portion of slit (1318b) are blocked by the spool (1320), thereby limiting fluid flow. FIG. 13E illustrates the valve (1300) in an open state where the spool (1320) blocks little, if any, portion of the orifice (1314).

The valve (1300) depicted in FIGS. 13A-13E may be configured to linearly slide the spool (1320) within the sleeve (1310). The orifice area of the valve (1300) may be a function of a linear position of the spool (1320) as controlled by a valve actuator. In other variations, the spool (1320) may move within the sleeve (1310) in a rotary manner. In these variations, the orifice area of the valve (1300) may be a function of an angular rotation of spool (1320) relative to the orifice (1314) as controlled by a valve actuator. Different actuation mechanisms exhibit varying performance characteristics including response rate, power consumption, size, cost, complexity, and the like. In some variations, a voice coil actuator may be coupled either directly or through one or more flexible elements to a linear spool valve. Power to a voice coil actuator may be required to maintain a specific valve position. In some variations using a voice coil actuator, the valve may comprise a spring to set a power OFF valve position when the actuator is in a power OFF state.

In some variations, the voice coil actuator may include a permanent magnet and a coil movable with respect to each other. The permanent magnet may generate a magnetic field in which the coil moves when a current is applied to the coil. In other variations, the coil may remain stationary as the magnet moves when a current is applied. The amount of current applied may correspond to a position of the coil with respect to the magnet. The polarity of the current may correspond to a direction of travel of the coil with respect to the magnet. For a voice coil actuator, the force produced may be proportional and substantially linear to the current applied such that the velocity of the coil may be proportional to the voltage applied. Thus, the voice coil actuator may have a substantially linear time and force response. A direction of movement of the coil may correspond to a polarity of the current. In some variations, a voice coil actuator, and thus the voice coil control valve, may have a rapid response rate (i.e. greater than 100 cycles per second), and a low power consumption (i.e. less than 1.8 Watts, or 150 mAmps at 12V). Such an actuator and/or valve may be referred to herein as a voice coil or voice coil valve.

In some variations, a solenoid valve may comprise a stationary iron core with a coil and a movable iron armature. The armature may be configured to move when current is applied to the coil. A solenoid actuator may further comprise a spring configured for return movement when current is removed from the coil. A solenoid actuator may operate unidirectionally and against a return spring. Due to the spring return, the response time of the valve in the return direction may be proportional to the spring rate. Therefore, a stiff spring may be provided to achieve fast response times. An armature force must overcome this spring force to stay at any given valve position. Therefore, the amount of power required to hold a valve position may increase proportionally to decreasing response times of the valve. Solenoid valves may therefore provide ON/OFF operation and may be non-linear (e.g., generate force proportional to the square of the current). In some variations, a valve actuator may comprise a brushless DC motor. The motor may be coupled to a linear valve using a screw or a rotary valve either directly or indirectly through a transmission system. The hydraulic assemblies disclosed herein may use any suitable valve actuator.

FIGS. 13F-13I depict fluid flow through a valve (1300) and in particular illustrate schematic diagrams of the valve in a fully open state (FIG. 13F), high resistance state (FIG. 13G), lock out state (FIG. 13H), and power OFF state (FIG. 13T). For the sake of clarity, the same elements in FIG. 13F are not labeled in FIGS. 13G-13I.

In FIG. 13F, the spool (1320) is at a first spool position within the sleeve (1310). At the first spool position, fluid flows from the second port (1372) through the first port (1370) with flow blocked from the third port (1374). In the first spool position, there is a relatively low level of resistance to fluid flow such that an amputee may experience a corresponding low level of resistance to joint rotation.

In FIG. 13G, the spool (1320) is at a second spool position within the sleeve (1310). At the second spool position, fluid flow through the second port (1372) and the first port (1370) is relatively lower than in the first spool position. For example, the spool (1320) overlaps a significant portion of the orifice (1314) such that there is a relatively intermediate and/or high level of resistance to fluid flow such that an amputee may experience a corresponding intermediate and/or high level of resistance to joint rotation.

In FIG. 13H, the spool (1320) is at a third spool position within the sleeve (1310).

At the third spool position, fluid does not flow through the valve (1300). All of the orifices (1314) are completely blocked by the spool (1320). This condition may be referred to as lock out and corresponds to maximum resistance to fluid flow where the prosthetic joint may be fixed at a particular angle.

As shown in FIG. 13I, when power is shut OFF, the spring (1360) may bias the coil bobbin (1354) to a hard stop position and thereby permits fluid flow between the third port (1374) and first port (1370). The spool (1.320) in FIG.

131 is at a fourth spool position within the sleeve (1310). At the fourth spool position, fluid flows through the third port (1374) and the first port (1370) with fluid flow blocked with respect to the second port (1372).

II. Methods

Also described here are methods for controlling rotational resistance of a prosthesis using the systems and devices described herein. In some variations, the process may begin by transmitting hydraulic fluid in the fluid circuit as described herein during the flexion state during prosthesis flexion and when the prosthesis variable resistance valve is powered. Hydraulic fluid may be transmitted in the fluid circuit as described herein during the extension state during prosthesis extension and when the prosthesis variable resistance valve is powered.

In some variations, the process may begin by transmitting hydraulic fluid in the fluid circuit as described herein during the flexion state during prosthesis flexion and when the prosthesis variable resistance valve is powered. Hydraulic fluid may be transmitted in the fluid circuit as described herein during the extension state during prosthesis extension and when the prosthesis variable resistance valve is powered. Hydraulic fluid may be transmitted in the fluid circuit as indicated during the power OFF flexion state during prosthesis flexion and when the prosthesis variable resistance valve is not powered In some variations, the process may begin by transmitting hydraulic fluid in the fluid circuit as described herein during the flexion state during prosthesis flexion and when the prosthesis variable resistance valve is powered. Hydraulic fluid may be transmitted in the fluid circuit as described herein during the extension state during prosthesis extension and when the prosthesis variable resistance valve is powered. Hydraulic fluid may be transmitted in the fluid circuit as described herein during the power OFF flexion state during prosthesis flexion and when the prosthesis variable resistance valve is not powered. Hydraulic fluid may be transmitted in the fluid circuit as described herein during the power OFF extension state during prosthesis extension and when the prosthesis variable resistance valve is not powered.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcon troller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

In some variations, the systems and methods may be in communication with other computing devices (not shown) via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), wireless personal area network (PAN) (e.g., Bluetooth, Bluetooth Low Energy), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some variations, the systems, devices, and methods described herein may include a radiofrequency receiver, transmitter, and/or optical (e.g., infrared) receiver and transmitter to communicate with one or more devices and/or networks.

The specific examples and descriptions herein are exemplary in nature and variations may be developed by those skilled in the art based on the material taught herein without departing from the scope of the present invention, which is limited only by the attached claims.

The invention claimed is:
1. A prosthesis, comprising:
   a first cylinder comprising a first cylinder port and a second cylinder port;
   a first piston slidable within the first cylinder;
   a fluid sump comprising a sump port, and
   a fluid circuit, comprising:
      a first fluid channel comprising a first channel inlet, a first channel outlet, and a unidirectional variable-resistance valve configured to set a variable resistance to fluid flow through the first fluid channel;
      a second fluid channel comprising a second channel inlet, a second channel outlet, and a second channel check valve;
      a third fluid channel comprising a third channel inlet, a third channel outlet, and a third channel check valve;
      a fourth fluid channel comprising a fourth channel inlet, a fourth channel outlet, and a fourth channel check valve;
      a fifth fluid channel comprising a fifth channel inlet, a fifth channel outlet, and a fifth channel check valve;
      a first intersection comprising the first channel inlet, the second channel outlet, and the fifth channel outlet;
      a second intersection comprising the first cylinder port, the second channel inlet, and the third channel outlet;
      a third intersection comprising the sump port, the third channel inlet, and the fourth channel inlet; and
      a fourth intersection comprising the second cylinder port, the fourth channel outlet, and the fifth channel inlet.

2. The prosthesis of claim 1, further comprising an extension state during cylinder extension wherein the fluid circuit is configured to permit fluid flow along a third fluid path sequentially through the first cylinder port, the second channel check valve, the variable-resistance valve, the fourth channel check valve, and to the second cylinder port.

3. The prosthesis of claim 2, wherein the extension state is further configured to:
   permit fluid flow along a fourth fluid path sequentially from the sump port to the fourth channel check valve; and
   resist fluid flow through the third channel check valve and the fifth channel check valve: and
   permit fluid flow simultaneously in the third and fourth fluid paths.

4. The prosthesis of claim 1, further comprising a mechanical sensor, wherein a resistance of the variable-resistance valve is determined based upon input from the mechanical sensor.

5. The prosthesis of claim 1, wherein the fluid circuit further comprises a three-way valve comprising a first valve port connected to the fluid sump at a second sump port, a second valve port connected to the second intersection, and a third valve port connected to the fourth intersection.

6. The prosthesis of claim 5, further comprising a variable resistor located between the third valve port and the fourth intersection along a sixth fluid channel, the sixth fluid channel comprising a sixth channel inlet at the fourth intersection and a sixth channel outlet connected to the third valve port.

7. The prosthesis of claim 6, wherein the variable resistor comprises a unidirectional variable resistor configured to permit flow from the fourth intersection to the third valve port.

8. The prosthesis of claim 5, wherein the three-way valve is a normally open three-way valve and wherein the three-way valve is configured to permit fluid passage between the first, second, and third valve ports when open, and blocks fluid passage between the first, second, and third valve ports when closed.

9. The prosthesis of claim 7, wherein the variable resistor blocks fluid flow from the third valve port to the fourth intersection regardless of whether the three-way valve is open or closed.

10. The prosthesis of claim 9, further comprising a power-off flexion state during cylinder compression wherein the fluid circuit is configured to permit fluid flow along a fifth fluid path sequentially through the second cylinder port, the variable resistor, the third valve port, the second valve port, and to the first cylinder port and to permit fluid flow along a sixth fluid path from the first valve port to the fluid sump.

11. The prosthesis of claim 9, further comprising a power-off extension state wherein the fluid circuit is configured to permit fluid flow along a seventh fluid path sequentially through the first cylinder port, the second valve port, the first valve port, the first sump port, the fourth fluid channel, and to the second cylinder port.

12. The prosthesis of claim 1, wherein the variable resistance valve is a three-way spool valve and further comprises a secondary channel inlet.

13. The prosthesis of claim 12, wherein the fluid circuit further comprises:
   a seventh fluid channel comprising a seventh channel inlet, a seventh channel outlet, and a seventh channel check valve, wherein the seventh channel inlet is connected to the first cylinder port or the second intersection;
   an eighth fluid channel comprising an eighth channel inlet, an eighth channel outlet, and a variable resistor; and
   a fifth intersection comprising the seventh fluid channel outlet, the eighth channel outlet and the secondary channel inlet of the three-way spool valve; wherein the first intersection further comprises the eighth channel inlet.

14. The prosthesis of claim 13, further comprising a power-off flexion state during cylinder compression wherein the fluid circuit is configured to permit fluid flow along an eighth fluid path sequentially through the second cylinder port, the fifth fluid channel, the eighth fluid channel, the secondary channel inlet of the variable-resistance valve, the third fluid channel, and to the first cylinder port, and to permit fluid flow from the first channel outlet to the fluid sump.

15. The prosthesis of claim 13, further comprising a power-off extension state during cylinder extension wherein the fluid circuit is configured to permit fluid flow along a ninth fluid path sequentially through the first cylinder port, the seventh fluid channel, the first channel inlet, the variable-resistance valve, the fourth fluid channel, and to the second cylinder port, and to permit a fluid flow from the fluid sump to the fourth fluid channel.

16. The prosthesis of claim 12, wherein the three-way spool valve comprises a spring and is configured to normally permit fluid communication between the secondary channel inlet and the first channel outlet when the three-way spool valve is not powered.

17. The prosthesis of claim 1, wherein the fluid sump comprises a spring-biased piston or a pneumatic piston.

18. The prosthesis of claim 1, further comprising: an upper joint member coupled to the first piston; and a lower joint member coupled to the upper joint member and the first cylinder.

19. A fluid circuit, comprising:
a first fluid channel comprising a first channel inlet, a first channel outlet, and a unidirectional variable-resistance valve configured to set a variable resistance to flow through the first fluid channel;
a second fluid channel comprising a second channel inlet, a second channel outlet, and a second channel check valve;
a third fluid channel comprising a third channel inlet, a third channel outlet and a third channel check valve;
a fourth fluid channel comprising a fourth channel inlet, a fourth channel outlet, and a fourth channel check valve;
a fifth fluid channel comprising a fifth channel inlet, a fifth channel outlet and a fifth channel check valve;
a first intersection comprising the first channel inlet, the second channel outlet, and the fifth channel outlet;
a second intersection comprising a first bi-directional channel, the second channel inlet and the third channel outlet;
a third intersection comprising a second bi-directional channel, the third channel inlet and the fourth channel inlet; and
a fourth intersection comprising a third bi-directional channel, the fourth channel outlet and the fifth channel inlet.

20. The fluid circuit of claim 19, further comprising a first state wherein the fluid circuit is configured to permit fluid flow along a first fluid path sequentially through the third bi-directional channel, the fifth channel check valve, the variable-resistance valve, the third channel check valve, and to the first directional channel.

21. The fluid circuit of claim 20, wherein the first state is further configured to permit fluid flow along a second fluid path through the variable-resistance valve and to the second bi-directional channel.

22. The fluid circuit of claim 20, wherein the first state is further configured to resist fluid flow through the second channel check valve and the fourth channel check valve.

23. The fluid circuit of claim 20, wherein the first state is configured to permit fluid flow simultaneously in the first and second fluid paths.

24. The fluid circuit of claim 19, further comprising a second state wherein the fluid circuit is configured to permit fluid flow along a third fluid path sequentially through the first bi-directional channel, the second channel check valve, the variable-resistance valve, the fourth channel check valve, and to the third bi-directional channel.

25. The fluid circuit of claim 24, wherein the second state is further configured to permit fluid flow along a fourth fluid path sequentially through the second bi-directional channel and the fourth channel check valve.

26. The fluid circuit of claim 24, wherein the second state is further configured to resist fluid flow through the third channel check valve and the fifth channel check valve.

27. The fluid circuit of claim 24, wherein the second state is configured to permit fluid flow simultaneously along the third and fourth fluid paths.

28. The fluid circuit of claim 19, further comprising a mechanical sensor and wherein a resistance of the variable-resistance valve is determined based upon input from the mechanical sensor.

29. The fluid circuit of claim 19, wherein the variable-resistance valve is selected from the group consisting of a solenoid valve, a spool valve, and a voice coil valve.

30. The fluid circuit of claim 19, wherein the fluid circuit further comprises a three-way valve, comprising a first valve port connected to the second bi-directional channel, a second valve port connected to the second intersection, and a third valve port connected to the fourth intersection.

31. The fluid circuit of claim 30, further comprising a variable resistor located between the third valve port and the fourth intersection along a sixth fluid channel, the sixth fluid channel comprising a sixth channel inlet at the fourth intersection and a sixth channel outlet connected to the third valve port.

32. The fluid circuit of claim 31, wherein the variable resistor is a unidirectional variable resistor configured to permit flow from the fourth intersection to the third valve port.

33. The fluid circuit of claim 31, wherein the three-way valve is a normally open three-way valve.

34. The fluid circuit of claim 31, wherein the three-way valve permits fluid passage between the first, second, and third valve ports when open, and blocks fluid passage between the first, second, and third valve ports when closed.

35. The fluid circuit of claim 34, wherein the variable resistor blocks fluid flow from the third valve port to the fourth intersection regardless of whether the three-way valve is open or closed .

36. The fluid circuit of claim 35, further comprising a third state wherein the fluid circuit is configured to permit fluid flow along a fifth fluid path sequentially through the third bi-directional channel, the variable resistor, the third valve port, the second valve port, and to the first bi-directional channel.

37. The fluid circuit of claim 36, wherein the third state of the fluid circuit is further configured to permit a fluid flow along a sixth fluid path from the first valve port to the second bi-directional channel.

38. The fluid circuit of claim 35, further comprising a power-off extension state wherein the fluid circuit is configured to permit fluid flow along a seventh fluid path sequentially through the first cylinder port, the second valve port, the first valve port, the fourth fluid channel, and to the second cylinder port.

* * * * *